United States Patent
Sprinkle et al.

(10) Patent No.: US 12,396,786 B2
(45) Date of Patent: Aug. 26, 2025

(54) SYSTEMS FOR ABLATING TISSUE

(71) Applicant: Stryker Corporation, Kalamazoo, MI (US)

(72) Inventors: Thomas Bowen Sprinkle, Kalamazoo, MI (US); Sunil Udaya Simha Moda, Portage, MI (US); Brandon J. Morse, Vicksburg, MI (US); Andrew J. Kohtala, Galesburg, MI (US); Volker Sandow, Elzach (DE); John Coleman Horton, IV, Austin, TX (US); Christopher Scott Brockman, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 771 days.

(21) Appl. No.: 17/441,506

(22) PCT Filed: Mar. 23, 2020

(86) PCT No.: PCT/US2020/024235
§ 371 (c)(1),
(2) Date: Sep. 21, 2021

(87) PCT Pub. No.: WO2020/198150
PCT Pub. Date: Oct. 1, 2020

(65) Prior Publication Data
US 2022/0175444 A1  Jun. 9, 2022

Related U.S. Application Data

(60) Provisional application No. 62/822,558, filed on Mar. 22, 2019.

(51) Int. Cl.
*A61B 18/14* (2006.01)
*A61B 18/00* (2006.01)

(52) U.S. Cl.
CPC ...... *A61B 18/1482* (2013.01); *A61B 18/1492* (2013.01); *A61B 2018/00166* (2013.01);
(Continued)

(58) Field of Classification Search
CPC ............ A61B 18/1482; A61B 18/1492; A61B 2018/00166; A61B 2018/00339;
(Continued)

(56) References Cited

U.S. PATENT DOCUMENTS

| 5,334,193 A | 8/1994 | Nardella |
| 6,171,275 B1 | 1/2001 | Webster, Jr. |

(Continued)

FOREIGN PATENT DOCUMENTS

WO  2018200254 A2  11/2018

OTHER PUBLICATIONS

Amazon.com, "10ml Syringe with Luer Slip Tip—100 Sterile Syringes by Vare Touch—No Needle, Great for Dispensing Oral Medicine and Home Care", https://www.amazon.com/10ml-Syringe-Luer-Slip-Tip/dp/B01JJYDFHM/ref=sr_1_3?dchild=1&keywords=10ml+luer+slip+syringe&qid=1584447349&sr=8-3, 2020, 8 pages.
(Continued)

*Primary Examiner* — Linda C Dvorak
*Assistant Examiner* — Abigail Bock
(74) *Attorney, Agent, or Firm* — Howard & Howard Attorneys PLLC

(57) ABSTRACT

An irrigated electrode assembly has a proximal portion with a proximal end and a distal portion with a distal end. The assembly includes a first conduit defining an irrigation channel and a second conduit, both of which extend from the proximal portion to the distal portion of the irrigated electrode assembly. A proximal and a distal emitter is located on the distal portion of the assembly with the distal emitter being positioned distally relative to the proximal emitter. A (Continued)

fluid irrigation port is defined by the proximal or distal emitter and is in fluid communication with the first conduit. An insulative spacer extends between a distal end of the proximal emitter and a proximal end of the distal emitter. An insulative body houses the first and second conduits and extends from the proximal portion of the irrigated electrode assembly to a proximal end of the proximal emitter.

18 Claims, 24 Drawing Sheets

(52) U.S. Cl.
CPC ............. *A61B 2018/00339* (2013.01); *A61B 2018/00434* (2013.01); *A61B 2018/00511* (2013.01); *A61B 2018/00529* (2013.01); *A61B 2018/00541* (2013.01); *A61B 2018/00565* (2013.01); *A61B 2018/00577* (2013.01); *A61B 2018/00821* (2013.01); *A61B 2218/002* (2013.01)

(58) Field of Classification Search
CPC   A61B 2018/00434; A61B 2018/00511; A61B 2018/00529; A61B 2018/00541; A61B 2018/00577; A61B 2018/00821; A61B 2218/002
See application file for complete search history.

(56) References Cited

U.S. PATENT DOCUMENTS

| | | |
|---|---|---|
| 6,241,725 B1 | 6/2001 | Cosman |
| 6,402,742 B1 | 6/2002 | Blewett et al. |
| 6,497,705 B2 | 12/2002 | Comben |
| 6,575,969 B1 | 6/2003 | Rittman, III et al. |
| 6,632,221 B1 | 10/2003 | Edwards et al. |
| 6,702,810 B2 | 3/2004 | McClurken et al. |
| 6,706,039 B2 | 3/2004 | Mulier et al. |
| 6,736,810 B2 | 5/2004 | Hoey et al. |
| 6,764,487 B2 | 7/2004 | Mulier et al. |
| 6,887,237 B2 | 5/2005 | McGaffigan |
| 6,896,675 B2 | 5/2005 | Leung et al. |
| 6,989,004 B2 | 1/2006 | Hinchliffe et al. |
| 7,108,696 B2 | 9/2006 | Daniel et al. |
| 7,261,711 B2 | 8/2007 | Mulier et al. |
| 7,294,127 B2 | 11/2007 | Leung et al. |
| 7,306,596 B2 | 12/2007 | Hillier et al. |
| 7,344,533 B2 | 3/2008 | Pearson et al. |
| 7,416,552 B2 | 8/2008 | Paul et al. |
| 7,771,420 B2 | 8/2010 | Butty et al. |
| 7,862,563 B1 | 1/2011 | Cosman et al. |
| 7,998,140 B2 | 8/2011 | McClurken et al. |
| 8,187,268 B2 | 5/2012 | Godara et al. |
| 8,211,095 B2 | 7/2012 | Gowda et al. |
| 8,348,937 B2 | 1/2013 | Wang et al. |
| 8,518,036 B2 | 8/2013 | Leung et al. |
| 8,540,710 B2 | 9/2013 | Johnson et al. |
| 8,882,755 B2 | 11/2014 | Leung et al. |
| 8,974,453 B2 | 3/2015 | Wang |
| 9,173,700 B2 | 11/2015 | Godara et al. |
| 9,241,760 B2 | 1/2016 | Godara et al. |
| 9,474,573 B2 | 10/2016 | Leung et al. |
| 9,616,199 B2 | 4/2017 | Wang et al. |
| 9,675,408 B2 | 6/2017 | Godara et al. |
| 9,730,748 B2 | 8/2017 | Curley |
| 9,770,282 B2 | 9/2017 | Hoey et al. |
| 9,788,889 B2 | 10/2017 | Godara et al. |
| 10,105,175 B2 | 10/2018 | Godara et al. |
| 10,130,418 B2 | 11/2018 | Wang et al. |
| 10,136,943 B1 | 11/2018 | Cosman, Jr. et al. |
| 10,206,739 B2 | 2/2019 | Godara et al. |
| 10,499,985 B2 | 12/2019 | Wang et al. |
| 10,548,642 B2 | 2/2020 | Harper |
| 2006/0264831 A1 | 11/2006 | Skwarek et al. |
| 2007/0049923 A1 | 3/2007 | Jahns |
| 2008/0071267 A1 | 3/2008 | Wang et al. |
| 2008/0091193 A1 | 4/2008 | Kauphusman et al. |
| 2012/0010490 A1* | 1/2012 | Kauphusman ......... A61B 5/287 600/373 |
| 2012/0150165 A1 | 6/2012 | Conley et al. |
| 2017/0238993 A1* | 8/2017 | Curley ................. A61B 18/04 |
| 2019/0038343 A1 | 2/2019 | Sutton et al. |
| 2020/0129232 A1 | 4/2020 | Wang et al. |

OTHER PUBLICATIONS

Amazon.com, Care Touch Luer Lock Tip Syringes 5 mL 100 Disposable Syringes Without Needles—Great for Oral Medicine, Home Care, and Hobbies, https://www.amazon.com/5ml-Syringe-Only-Luer-Lock/dp/B01JJYYWH4/ref=sr_1_4?crid=2EU5SKJNMTPBS&dchild=1&keywords=5ml+luer+lock+syringe&qid=1584447489&sprefix=5+mL +luer+I%2Caps%2C156&sr=8-4, 2020, 7 pages.

International Search Report for Application No. PCT/US2020/024235 dated Ocrober 9, 2020, 4 pages.

Partial International Search Report for Application No. PCT/US2020/024235 dated Jul. 21, 2020, 3 pages.

\* cited by examiner

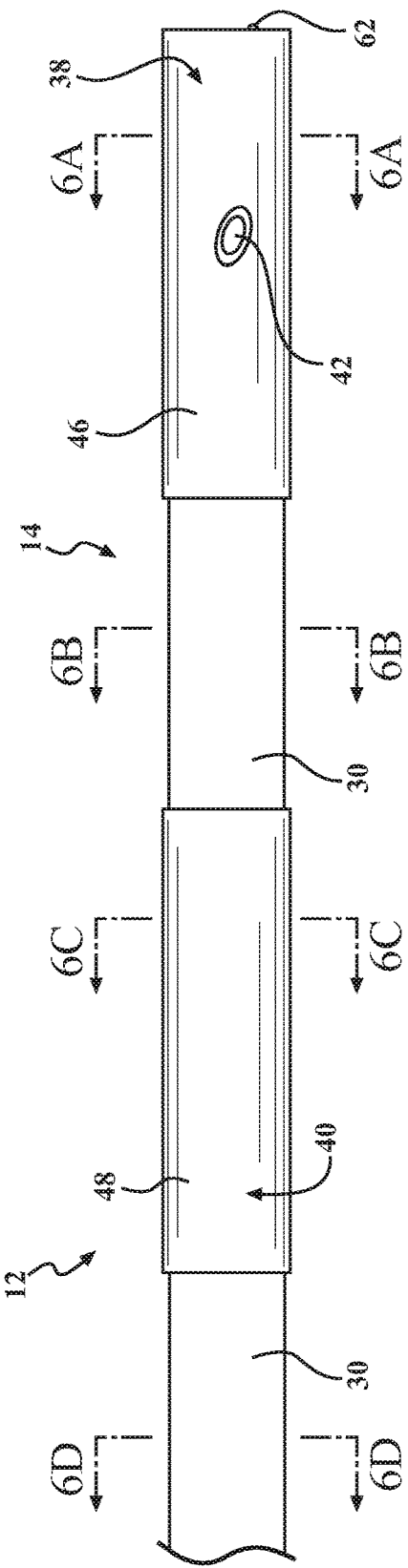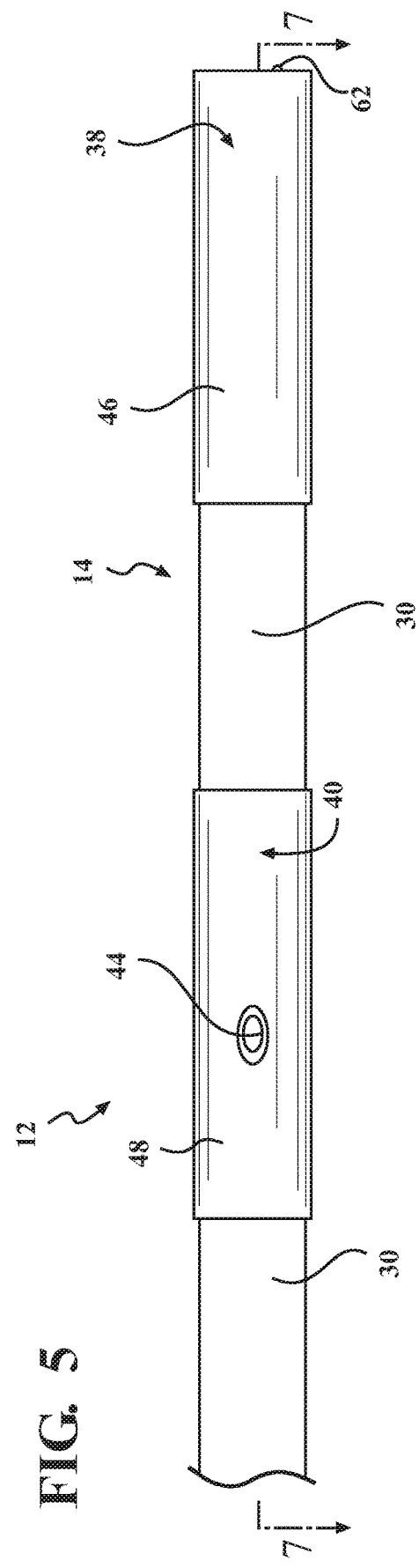

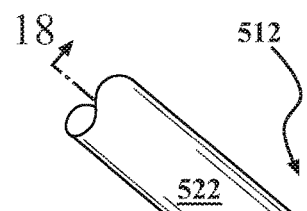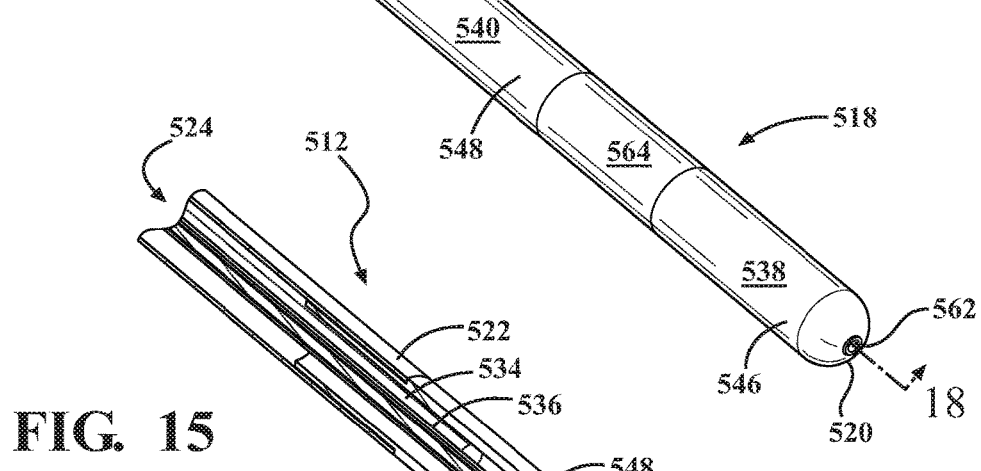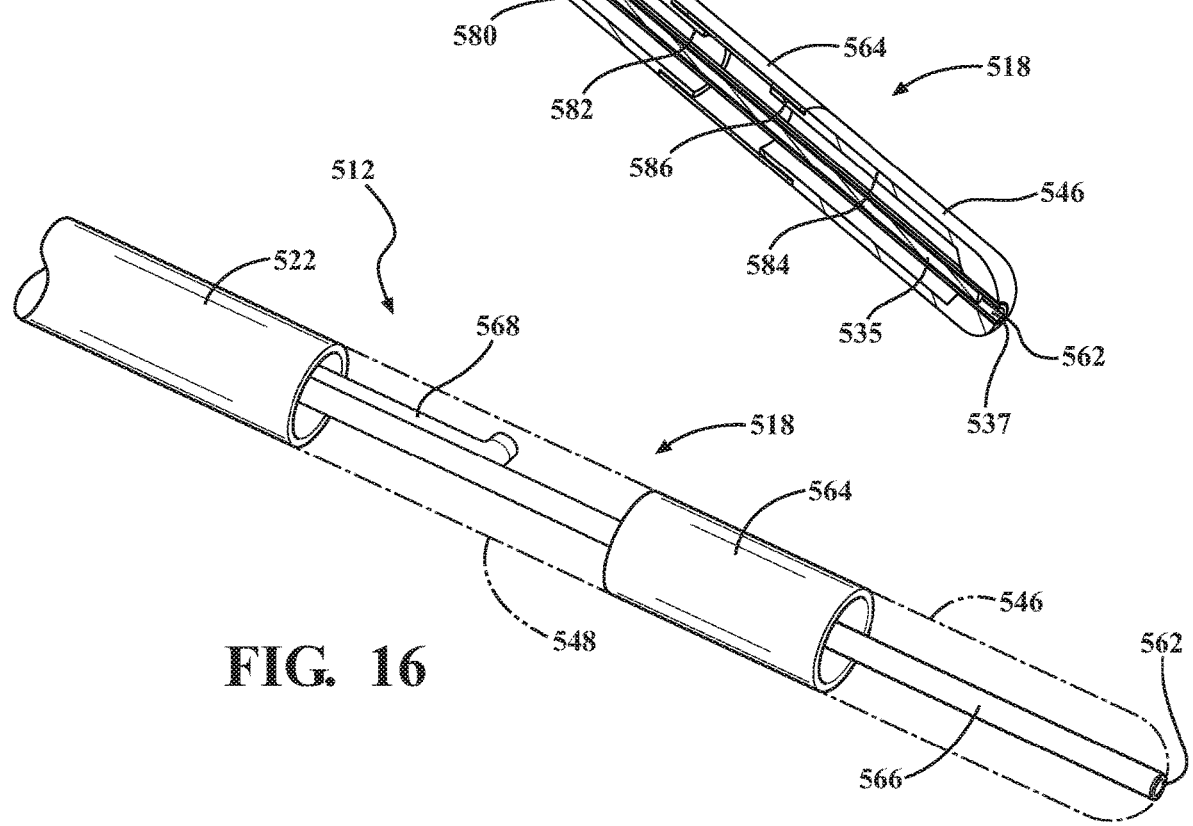

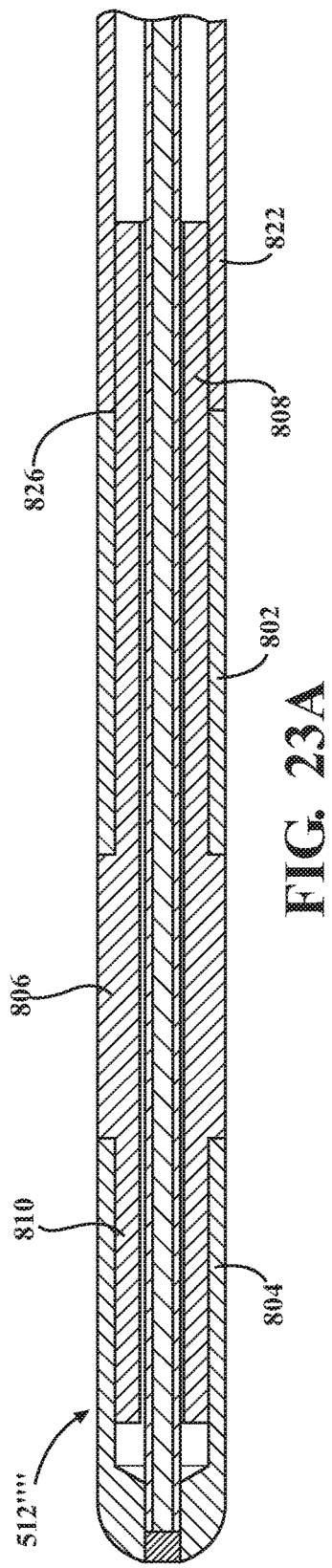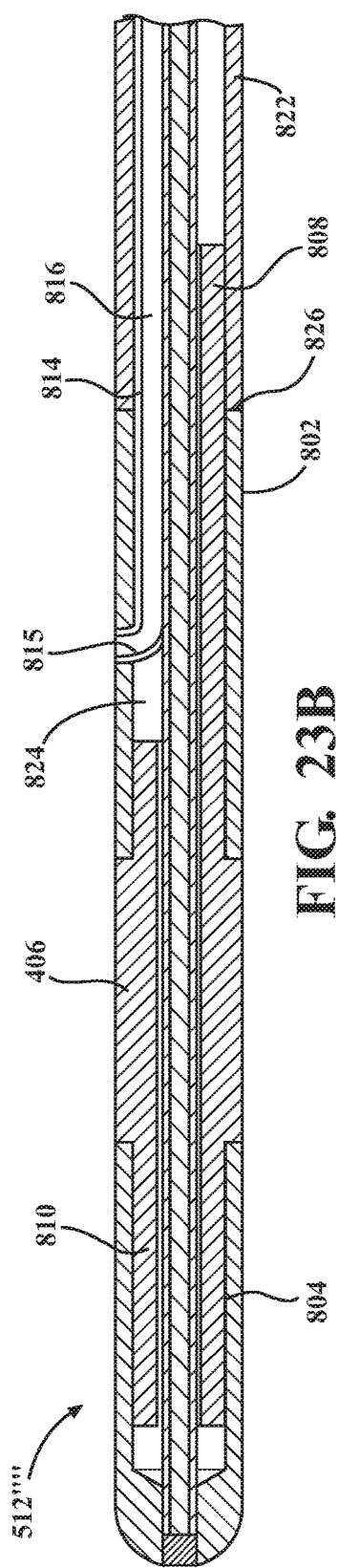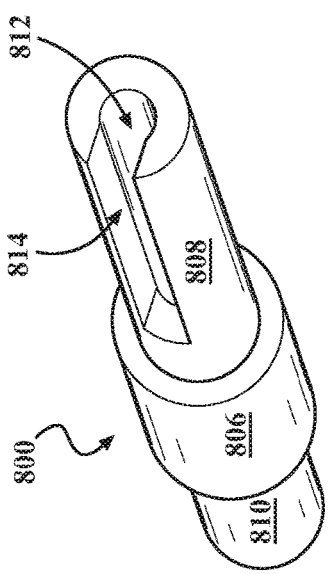
FIG. 23A
FIG. 23B
FIG. 23C

SYSTEMS FOR ABLATING TISSUE

CROSS-REFERENCE TO RELATED APPLICATION

The subject patent application is a national entry of International Application No. PCT/US2020/024235, filed Mar. 23, 2020, which claims priority to and all the benefits of U.S. Provisional Application No. 62/822,558, filed on Mar. 22, 2019, the entire contents of each are incorporated herein by reference.

BACKGROUND

An electrosurgical system, often referred to as an ablation system, is a set of components used to flow current through biological tissue to ablate at least some of the tissue through which the current is flowed to accomplish a desirable therapeutic effect.

For example, an ablation system is sometimes used to selectively destroy nerve tissue. This may be desirable if a set of the patient's nerves continually transmit signals to the brain that inaccurately indicate that a portion of the patient's body is in appreciable pain. If the receipt of these pain signals adversely affects the quality of life for the patient, the ablation system is employed to ablate the nerves responsible for the transmission of these signals. As a consequence of the tissue ablation process, necrosis occurs, and the nerve becomes a lesion. As a result of the nerve becoming a lesion, the nerve no longer transmits pain signals to the brain.

As another example, an ablation system is sometimes used to destroy tumors of the liver, kidney, lung, and bone. This may be desirable, for example, to stop the growth and spread of cancer. The ablation system is employed to ablate a targeted tumor. As a consequence of the tumor ablation, cellular necrosis occurs, the tumor is destroyed, and growth is curtailed or stopped.

Most ablation systems comprise an energy source and a device that delivers energy directly to the targeted biological tissue to cause cellular necrosis. Radiofrequency (RF), microwave (MW), laser, and high-intensity focused ultrasound (HIFU) systems apply energy to heat the tissue to at least 60° C. for maximum efficacy. Targeted biological tissue can be accessed percutaneously, laparoscopically, through a celiotomy incision, or endoscopically.

Further, some ablation systems comprise a fluid source and a device that delivers conductive fluid (e.g. saline) to the targeted biological tissue to control ablation temperature and volume.

Some ablation systems include an access cannula and an electrode/emitter assembly. The cannula is a needle like structure with sufficient strength to puncture or support lumen through the tissue and/or bone of the patient. The cannula is typically positioned adjacent to the biological tissue to be ablated. Once the access cannula is positioned, the electrode assembly can be inserted into the access cannula. The electrode assembly includes features for the delivery of energy and may also include features for the delivery of conductive fluid.

Despite advancements that have been made with such ablation systems, there is further need in the art for systems and methods that facilitate ablation in various locations within a patient, e.g. in bone. Further, such systems and method should improve the control of energy delivered to biological tissue, the temperature of the biological tissue during ablation, and the volume and thoroughness of tissue ablated.

SUMMARY

An ablation system is disclosed herein. In one example, an irrigated electrode assembly has a proximal portion with a proximal end and a distal portion with a distal end. The assembly includes a first conduit defining an irrigation channel and a second conduit, both of which extend from the proximal portion to the distal portion of the irrigated electrode assembly. A proximal emitter and a distal emitter are located on the distal portion of the irrigated electrode assembly with the distal emitter being positioned distally relative to the proximal emitter. A fluid irrigation port is located on the proximal emitter or the distal emitter of the irrigated electrode assembly and in fluid communication with the first conduit. An insulative spacer extends between a distal end of the proximal emitter and a proximal end of the distal emitter. An insulative body houses the first and second conduits and extends from the proximal portion of the irrigated electrode assembly to a proximal end of the proximal emitter.

In one example, an irrigated electrode assembly has a proximal portion with a proximal end, a distal portion with a distal end. The irrigated electrode assembly comprises a first conduit defining an irrigation channel extending from the proximal portion of the irrigated electrode assembly to the distal portion of the irrigated electrode assembly and a second conduit extending from the proximal portion of the irrigated electrode assembly to the distal portion of the irrigated electrode assembly. A proximal emitter is located on the distal portion of the irrigated electrode assembly and a distal emitter is located on the distal portion of the irrigated electrode assembly (and positioned distally relative to the proximal emitter). A fluid irrigation port is defined by the proximal emitter or the distal emitter of the irrigated electrode assembly and is in fluid communication with the first conduit. An insulative spacer extends between a distal end of the proximal emitter and a proximal end of the distal emitter. An insulative body extends from the proximal portion of the irrigated electrode assembly to a proximal end of the proximal emitter and defines a lumen that houses the first and second conduits. The proximal emitter has an outer diameter ($D_{PE}$) that is greater than an outer diameter ($D_{FC}$) of the first conduit and is greater than an outer diameter ($D_{SC}$) of the second conduit such that when the proximal end of the proximal emitter extends past a distal end of an access cannula, the proximal emitter is distinctly visible in tissue with electromagnetic imaging techniques.

In another example, the irrigated electrode assembly has a proximal portion with a proximal end and a distal portion with a distal end. The irrigated electrode assembly comprises an insulative body, a first conduit comprising an electrically conductive material and defining an irrigation channel extending from the proximal portion of the irrigated electrode assembly to the distal portion of the irrigated electrode assembly, and a second conduit comprising an electrically conductive material and defining a channel extending from the proximal portion of the irrigated electrode assembly to the distal portion of the irrigated electrode assembly. A thermocouple is housed within and insulated from the second conduit. A proximal emitter is located on the distal portion of the irrigated electrode assembly and defines a fluid irrigation port configured to discharge fluid into tissue. The first conduit is in electrical communication with the proximal emitter and the irrigation channel is in fluid communication with the fluid irrigation port. A distal emitter is located on the distal portion of the irrigated electrode assembly and positioned distally relative to the proximal emitter, wherein the second conduit is in electrical communication with said distal emitter.

An ablation system is also disclosed. The ablation system comprises an irrigated electrode assembly having a proximal portion with a proximal end, a distal portion with a distal end. The irrigated electrode assembly comprises an insulative body, a fluid intake port on the proximal portion of the irrigated electrode assembly, a first conduit comprising an electrically conductive material and defining an irrigation channel extending from the proximal portion of the irrigated electrode assembly to the distal portion of the irrigated electrode assembly, and a fluid irrigation port located on the distal portion. The system also includes a micro infusion module releasably coupled to the fluid intake port of the irrigated electrode assembly and sized to be held by a single hand. The micro infusion module comprises a potential energy accumulator which is configured to store and release potential energy and a fluid delivery actuator configured to cooperate with the potential energy accumulator. The fluid delivery actuator comprises a body defining a fluid reservoir and a piston moveably disposed in the fluid reservoir. The potential energy accumulator is configured to release the potential energy to actuate the piston of the fluid delivery actuator to discharge fluid from the fluid reservoir. Further, the fluid delivery actuator is in fluidic communication with the fluid intake port, the irrigation channel, and the fluid irrigation port. The potential energy accumulator and the fluid delivery actuator are configured to release the potential energy and actuate the piston to discharge fluid from the fluid reservoir into the irrigation channel and through the fluid irrigation port.

A method of ablating tissue with an ablation system comprising: an irrigated electrode assembly having a proximal portion with a proximal end and a distal portion with a distal end; and a micro infusion module sized to be held by a single hand is disclosed. The method comprises the steps of: positioning an access cannula into bone; inserting the irrigated electrode assembly at least partially into the access cannula; coupling the irrigated electrode assembly to an energy source, the energy source being positioned outside a sterile zone; filling a fluid reservoir of the micro infusion module with fluid; applying force to the micro infusion module to store potential energy therein; coupling the micro infusion module to the irrigated electrode assembly; positioning the micro infusion module within the sterile zone while the energy source remains outside the sterile zone; discharging fluid from the micro infusion module, through the irrigated electrode assembly, and into the tissue while the micro infusion module remains inside the sterile zone; and applying energy from the energy source to the tissue through the irrigated electrode assembly.

BRIEF DESCRIPTION OF THE DRAWINGS

Advantages of the present disclosure will be readily appreciated as the same becomes better understood by reference to the following detailed description when considered in connection with the accompanying drawings.

FIG. 4 is a close-up, side view of the distal portion of the irrigated electrode assembly of FIG. 1 which illustrates a distal emitter defining a distal fluid irrigation port on the distal portion of the irrigated electrode assembly;

FIG. 5 is a close-up side view of the distal portion of the irrigated electrode assembly of FIG. 1 (rotated 180° relative to the view of FIG. 4) which illustrates a proximal emitter defining a proximal fluid irrigation port on the distal portion of the irrigated electrode assembly and positioned proximally relative to the distal emitter;

FIG. 14 is a close-up view of the distal portion of the exemplary irrigated electrode assembly of FIG. 11;

FIG. 15 is a cross-sectional view of the distal portion of the irrigated electrode assembly of FIG. 14 along line 14-14;

FIG. 16 is a close-up view of the distal portion of the exemplary irrigated electrode assembly of FIG. 11 with a proximal and distal emitter made transparent;

FIG. 23A is a first cross-sectional a cross-sectional view of a distal portion of an exemplary irrigated electrode assembly;

FIG. 23B is a second cross-sectional view (rotated 180° relative to the view of FIG. 8A) of a distal portion of the exemplary irrigated electrode assembly of FIG. 23A;

FIG. 23C is an isolated view of an insulated spacer of the irrigated electrode assembly of FIG. 23A;

It should be appreciated that the drawings are illustrative in nature and are not necessarily drawn to scale.

DETAILED DESCRIPTION

Figure 1A:
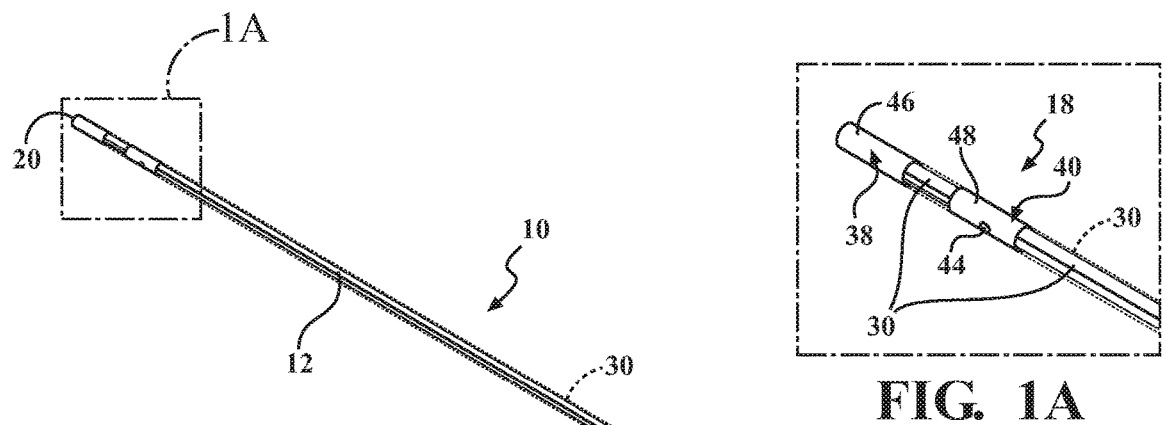
FIG. 1A is a close-up perspective view of a distal portion of the irrigated electrode assembly of FIG. 1.
Figure 1:
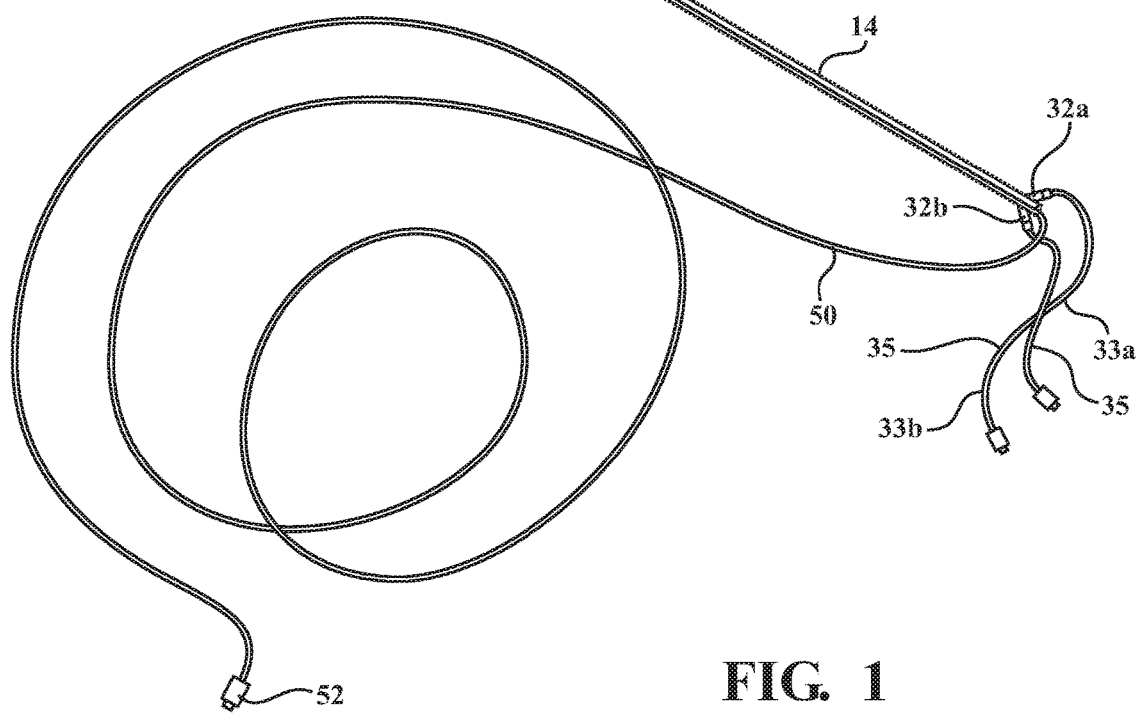
FIG. 1 is a perspective view of an ablation system including an exemplary irrigated electrode assembly which is used to ablate biological tissue.

With reference to the Figures, wherein like numerals indicate like parts throughout the several views, an ablation system 10 including an irrigated electrode assembly 12 is generally shown in FIG. 1.

Figure 2:
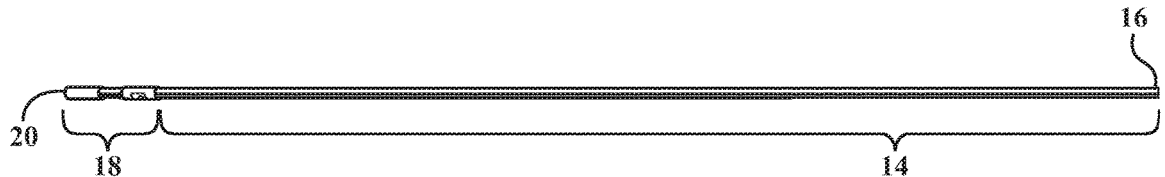
FIG. 2 is side view of the irrigated electrode assembly of FIG. 1.
Figure 3:
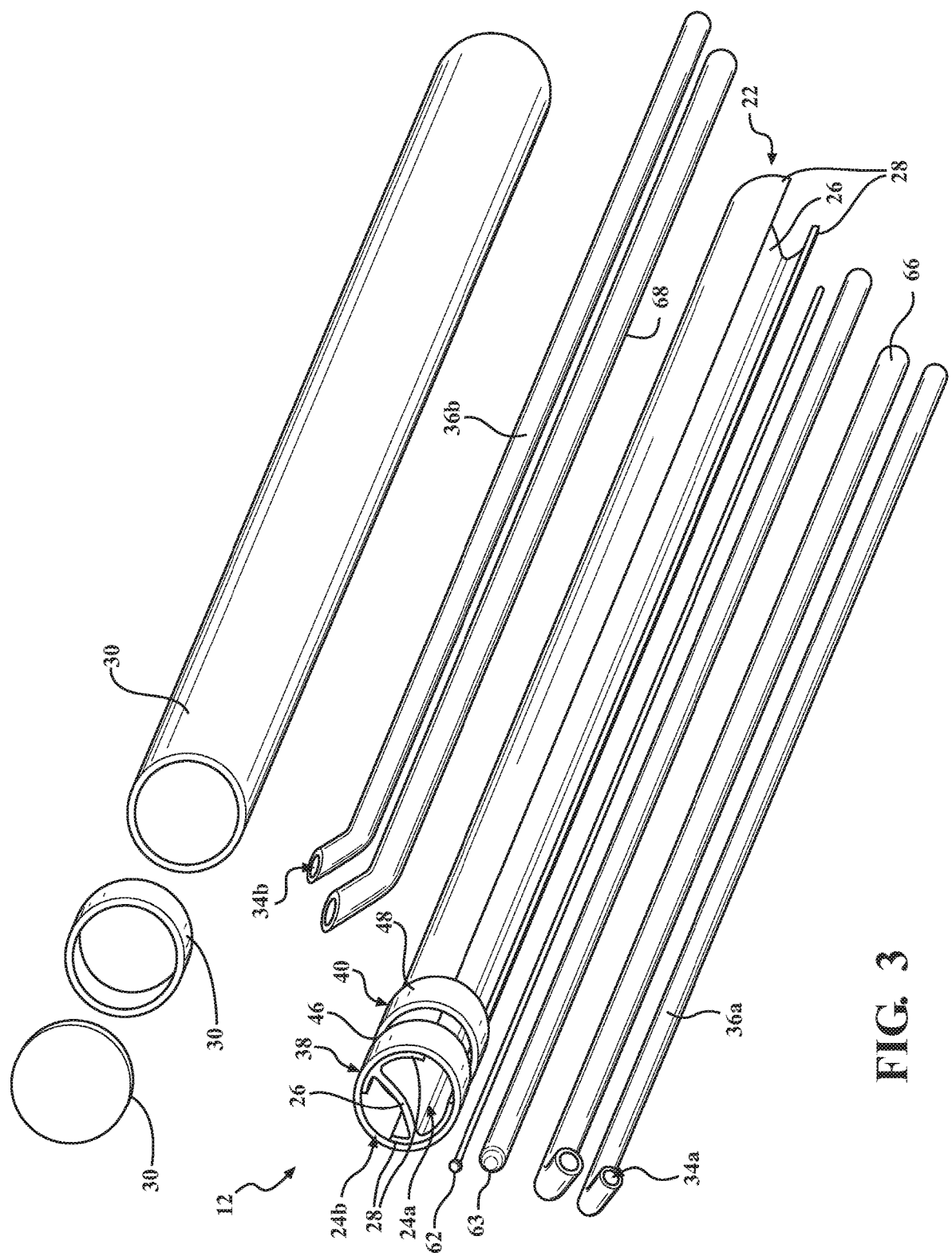
FIG. 3 is an exploded view of the of the irrigated electrode assembly of FIG. 1.

As is illustrated in the example ablation system of FIGS. 1-3, the irrigated electrode assembly 12 has a proximal portion 14 with a proximal end 16 and a distal portion 18 with a distal end 20. Further, FIGS. 4-7 provide various enlarged and cross-sectional views of the distal portion 18 of the irrigated electrode assembly 12.

Figure 6A:
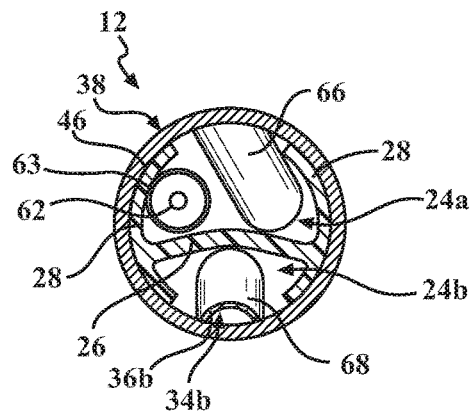
FIG. 6A is a cross-sectional view of the distal portion of the irrigated electrode assembly of FIG. 4 along line 6A-6A.
Figure 6B:
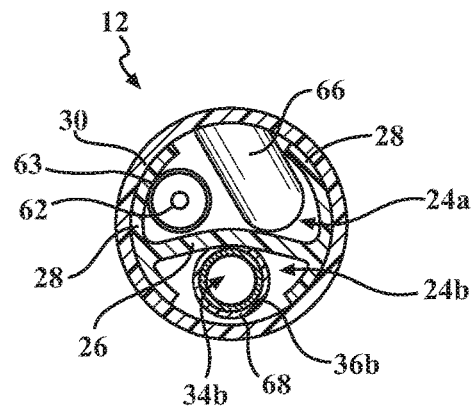
FIG. 6B is a cross-sectional view of the distal portion of the irrigated electrode assembly of FIG. 4 along line 6B-6B.
Figure 6C:
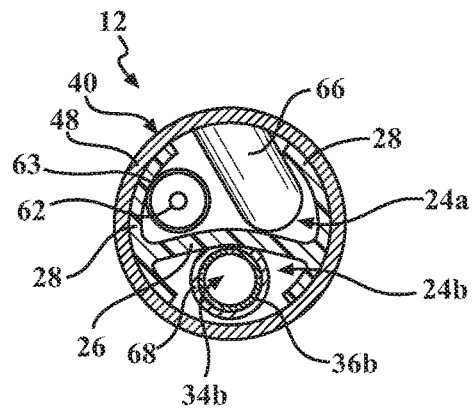
FIG. 6C is a cross-sectional view of the distal portion of the irrigated electrode assembly of FIG. 4 along line 6C-6C.
Figure 6D:
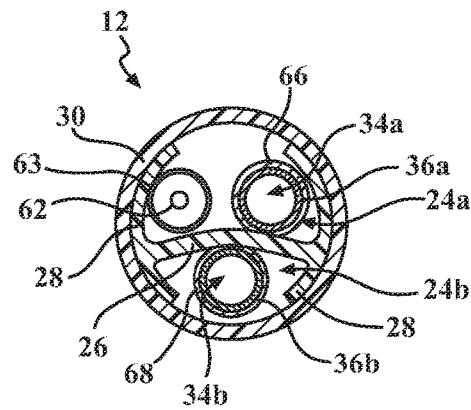
FIG. 6D is a cross-sectional view of a proximal portion of the irrigated electrode assembly of FIG. 4 along line 6D-6D.
Figure 7:
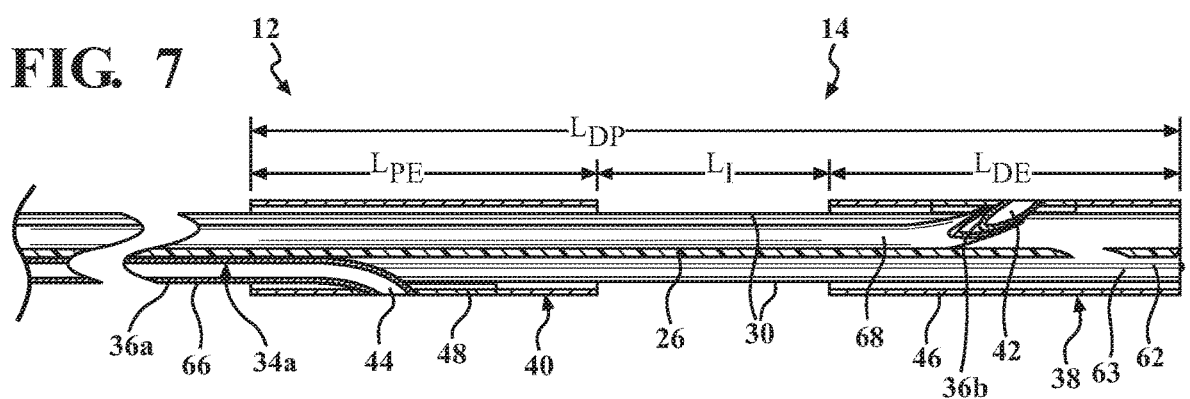
FIG. 7 is a cross-sectional view of the distal portion of the irrigated electrode assembly of FIG. 5 along line 7-7.

The irrigated electrode assembly 12 includes an insulative body 22 which can also be referred to as a support member. The insulative body 22 can be rigid or flexible. The insulative body 22 typically comprises a polymer, and may be formed, for example, via molding or extrusion processes known to those skilled in the art. In many non-limiting examples, the insulative body 22 comprises a thermoplastic elastomer. In some non-limiting examples, the insulative body 22 comprises polyether ether ketone ("PEEK"). In other non-limiting examples, the insulative body 22 comprises silicone. Further, the insulative body functions as an electrical insulator. The irrigated electrode assembly 12 includes one or more conduits 36, which in some instances may also be referred to as irrigation lines. In one example, the insulative body 22 extends at least a portion of the length of the irrigated electrode assembly 12 assembly to provide structure and electrically isolate a first conduit 36a defining a first irrigation channel 34a from a second conduit 36b within the irrigated electrode assembly 12. In the subject example, with particular reference to the exploded view of FIG. 3, the insulative body 22 extends at least a portion of the length of the irrigated electrode assembly 12. In one example, the insulative body 22 has a web 26, and one or more flanges 28 extending from each side of the web 26. FIGS. 6A-6D illustrate this example of the insulative body 22 comprising the web 26 and two flanges 28. As is also illustrated in FIGS. 6A-6D, the insulative body 22 cooperates with a spacer sheath 30, as well as with distal and proximal emitters 46, 48 to define two electrically isolated lumens 24a, 24b within the irrigated electrode assembly 12. The distal and proximal emitters 46, 48 comprise, in some examples, respective metallic sleeves, and can also be referred to as distal and proximal electrodes. The distal and proximal emitters 46, 48 are described in detail below. FIG. 6A illustrates cooperation of the insulative body 22 with the distal emitter 46 to partially define the two electrically isolated lumens 24a, 24b within the irrigated electrode assembly 12. FIG. 6B illustrates cooperation of the insulative body 22 with the spacer sheath 30 to partially define the two electrically isolated lumens 24a, 24b within the irrigated electrode assembly 12. FIG. 6C illustrates cooperation of the insulative body 22 with the proximal emitter 48 to partially define the two electrically isolated lumens 24a, 24b within the irrigated electrode assembly 12. FIG. 6D illustrates cooperation of the insulative body 22 with the spacer sheath 30 to partially define the two electrically isolated lumens 24a, 24b within the proximal portion 14 of the irrigated electrode assembly 12.

Figure 8:
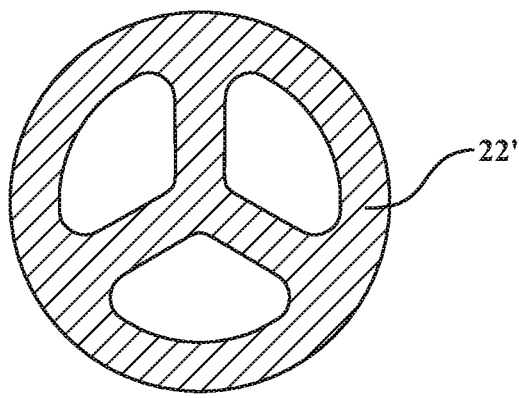
FIG. 8 is a cross-sectional view of an exemplary 3-lumen insulative body.
Figure 9:
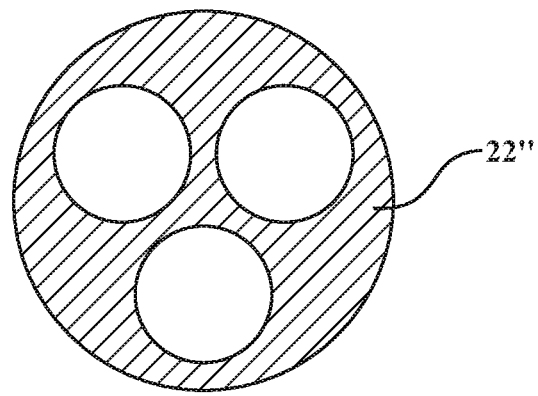
FIG. 9 is a cross-sectional view of another exemplary 3-lumen insulative body.
Figure 10:
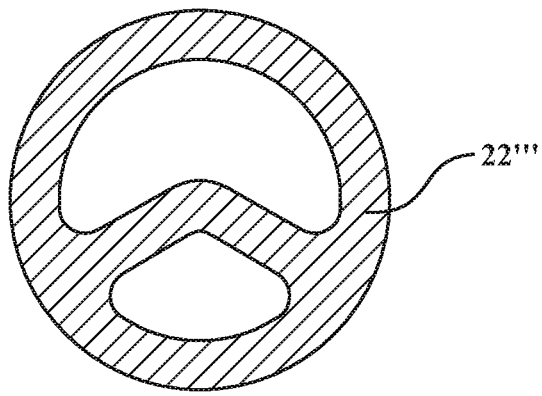
FIG. 10 is a cross-sectional view of an exemplary 2-lumen insulative body.

Referring to FIGS. 8-10, in another configuration, the irrigated electrode assembly 12 may include an insulative body 22', 22", 22'" having an alternative configuration. The insulative body 22', 22", 22'" can be rigid or flexible, and may comprise a polymer, and may be formed, for example, via molding or extrusion processes known to those skilled in the art. The insulative body 22', 22", 22'" may be symmetrical in cross section such that the insulative body 22', 22", 22'" provides for additional rigidity. Further, the insulative body 22', 22", 22'" functions as an electrical insulator. In one example, the insulative body 22', 22", 22'" extends at least a portion of the length of the irrigated electrode assembly 12 to provide structure and electrically isolate the first conduit 36a from the second conduit 36b within the irrigated electrode assembly 12. The insulative body 22', 22", 22'" may define two or three lumens along its length. Different from insulative body 22, insulative body 22', 22", 22'" may not need to be provided with the spacer sheath 30. The distal and proximal emitters 46, 48 may be coupled to proximal and distal locations of the insulative body 22', 22", 22''' using various attachment techniques, such as adhesive or metal deposition techniques. In embodiments where the insulative body 22', 22" defines three lumens, the first and second conduits 36a, 36b may each provided in a separate lumen 24, and the thermocouple 62 may be provided in still another separate lumen 24. Alternatively, in configurations where the insulative body 22''' is provided with only two lumens 24, the thermocouple 62 may share a lumen 24 with the first or second conduits 36a, 36b, or housed within one of the first and second conduits 36a, 36b.

It should be appreciated that the spacer sheath 30 can be discontinuous (e.g. cover the outer periphery of the irrigated electrode assembly 12 in certain portions but cover other portions, e.g. the transfer surfaces. The spacer sheath 30 can be used to fluidically and electrically isolate the proximal portion 14, the distal portion 18 between the distal and proximal emitters 46, 48, and the distal end 20 of the irrigated electrode assembly 12. The spacer sheath 30 typically comprises a polymer. In some examples, the polymer is an elastomer or a thermoplastic elastomer. In other examples, the polymer is a thermoplastic. In still other examples, the polymer is a thermoset. The spacer sheath 30 can be shrink applied via heat, applied as a pre shaped tubular segment(s), or even applied as a coating.

In some examples, the lumens 24 can be filled with a polymeric material (potting compound) such as epoxy that can act to structurally strengthen in the irrigated electrode assembly 12, glue the components of the irrigated electrode assembly 12 together, and also electrically isolate (or insulate) the individual components of the irrigated electrode assembly 12 from one another. The potting material can be rigid or flexible depending on the desired flexibility of the irrigated electrode assembly 12.

As its name implies, the irrigated electrode assembly 12 supplies fluid to targeted biological tissue, before, during, and/or after ablation. Irrigation of biological tissue with the micro infusion of fluid (e.g. saline or other conductive fluid) helps control temperature and prevents charring of biological tissue and thus generally helps control the irrigated electrode assembly 12 during use. To this end, the irrigated electrode assembly 12 includes one or more fluid intake ports 32 on the proximal portion 14 of the irrigated electrode assembly 12. The irrigated electrode assembly 12 may also include one or more flow restrictors 33a, 33b, which restrict the delivery of fluid into (and out of) the irrigated electrode assembly 12. Of course, the flow restrictors 33a, 33b may also be formed as part of a micro infusion module 100, which is described in detail below.

Referring back to FIG. 1, two fluid intake ports are illustrated 32a, 32b along with two flow restrictors (e.g. tubing with a predetermined restriction in cross-section to control the flow rate therethrough) 33a, 33b. In some examples, the flow restrictor 33 restricts fluid flow to a rate of from about 0.5 to about 15, or about 1 to about 12, mL/hour into the irrigated electrode assembly 12.

The irrigated electrode assembly 12 also includes one or more irrigation channels 34. Typically, the one or more irrigation channels 34 are defined by one or more conduits 36. In some examples, an insulating sheath is disposed about an outer peripheral surface of the one or more conduits 36. The insulating sheath typically comprises a polymer. In some examples, the polymer is an elastomer or a thermoplastic elastomer. In other examples, the polymer is a thermoplastic. In still other examples, the polymer is a thermoset. The insulating sheath can be shrink applied via heat, applied as a pre shaped tubular segment(s), or even applied as a coating.

As is best shown in the exploded view of FIG. 3, the irrigated electrode assembly 12 includes a first conduit 36a defining a first irrigation channel 34a and having a first insulative sheath 66 disposed thereon, and a second conduit 36b defining a second irrigation channel 34b and having a second insulative sheath 68 disposed thereon. The first and second conduits 36a, 36b extend from the proximal portion 14 (typically the proximal end 16) of the irrigated electrode assembly 12 to the distal portion 18 of the irrigated electrode assembly 12. The first and second conduits 36a, 36b are illustrated throughout FIGS. 1-7.

Further, the first and second conduits 36a, 36b comprise an electrically conductive material (e.g. metal). In many examples, both of the conduits 36a, can be used to carry energy to the biological tissue from an energy source 54 to the distal and proximal emitters 46, 48 and into the biological tissue. Not only does energy flow into the biological tissue from the distal and proximal emitters 46, 48, in some examples, energy flows between the distal and proximal emitters 46, 48 (through the biological tissue). In other examples, one of the conduits (either 36a or 36b) can be used to carry energy to the biological tissue from an energy source 54 and the other conduit (either 36a or 36b) can be used to carry energy from the biological tissue to the energy source 54. In other words, the first and second conduits 36a, 36b may have opposite polarity. The first and second conduits 36a, 36b are usually located on opposite sides of the flexible insulative body 22. As is best illustrated in FIGS. 6A-6D, the first and second conduits 36a, 36b may be electrically isolated from one another by the insulative body 22 comprising a web 26 and two flanges 28.

Referring back to FIG. 1, a conductor 50 and connector 52 are shown. The first and second conduits 36a, 36b carry energy provided by the energy source 54, e.g. an electrosurgical generator, in addition to carrying fluid to the surgical site. One suitable energy source 54 is a radiofrequency generator and control console sold under the tradenames MultiGen (MG1) and MultiGen 2 (MG2) by Stryker Corporation (Kalamazoo, Mich.), and those described in commonly-owned International Publication No. WO 2018/200254, published Nov. 1, 2018, the entire contents of which are hereby incorporated by reference in its entirety. More specifically, energy flows from the power source, to the connector 52, which plugs into the energy source 54, through the conductor 50. Energy then flows from the conductor to the first and second conduits 36a, 36b, the distal and proximal emitters 46, 48, and into biological tissue.

The energy source 54 is typically capable of sourcing a variable current to the irrigated electrode assembly 12. Typically, the current is AC current. A console may allow adjustment of frequency, current, and/or voltage levels of the sourced current for various time periods. The power source may be any one of a variety of power supplies intended for electrosurgical cutting, coagulation, and/or ablation. In some examples, such power supplies are generally capable of operating at radio frequencies of about 500 kHz and at power levels from 1 W to 300 W. The irrigated electrode assembly 12 includes a distal transfer surface 38 located on the distal portion 18 of the irrigated electrode assembly 12, and a proximal transfer surface 40 positioned proximally relative to the distal transfer surface 38 on the distal portion 18 of the irrigated electrode assembly 12. The proximal transfer surface 40 is defined by the proximal emitter 48, which can also be referred to as a proximal electrode. The proximal emitter 48 comprises a conductive material such as metal and, in many examples is annular in shape. Moreover, a proximal fluid irrigation port 44 is defined by the proximal emitter 48. The distal transfer surface 38 is defined by the distal emitter 46, which can also be referred to as a distal electrode. The distal emitter 46 comprises a conductive material such as metal and, in many examples is annular in shape. Moreover, a distal fluid irrigation port 42 is defined by the distal emitter 46. The proximal and distal fluid irrigation ports 44, 42 are in fluid communication with the first and second irrigation channels 34a, 34b and configured to discharge fluid adjacent the distal and proximal transfer surfaces 40, 38, respectively. In addition, first and second conduits 36a, 36b, which define the first and second irrigation channels 34a, 34b, are coupled electrically and mechanically to the proximal and distal emitters 48, 46. For example, the first and second conduits may be soldered to the proximal and distal emitters 48, 46.

FIG. 4 is a close-up, side view of the distal portion 18 of the irrigated electrode assembly 12, which illustrates the distal transfer surface 38 defining the distal fluid irrigation port 42. FIG. 5 is a close-up, side view of the distal portion of the irrigated electrode assembly of FIG. 4 rotated 180°, which illustrates the proximal transfer surface 40 defining the proximal fluid irrigation port 44.

As set forth above, the distal emitter 46 defines the distal transfer surface 38 and is mounted to the distal portion 18 of the irrigated electrode assembly 12, while the proximal emitter 48 defines the proximal transfer surface 40 and is mounted to the distal portion 18 of the irrigated electrode assembly 12 and positioned proximally relative to the distal emitter 46. The distal emitter 46 may be coupled to the insulative body 22 through the use of an adhesive. Similarly, the proximal emitter 48 may be coupled to the insulative body 22 with the use of an adhesive.

The distal emitter 46 and the proximal emitter 48 are spaced from one another axially. Additionally, the distal emitter 46 and the proximal emitter 48 are insulated from one another. This may be accomplished by positioning a portion of the spacer sheath 30 over the insulative body 22 between the proximal and distal emitters 48, 46.

In some examples, the irrigated electrode assembly 12 includes a thermocouple 62 to measure a temperature of biological tissue being ablated. The thermocouple can be sheathed with a protective layer 63 for insulative and/or durability purposes. Since, in many examples, the distal portion 18 is flexible, the protective layer 63 physically and electrically protects the thermocouple 62. The thermocouple 62 is exposed on a position on the distal portion 18 of the irrigated electrode assembly 12. In one example, the thermocouple 62 is exposed at the distal end 20 of the irrigated electrode assembly 12.

Figure 11:
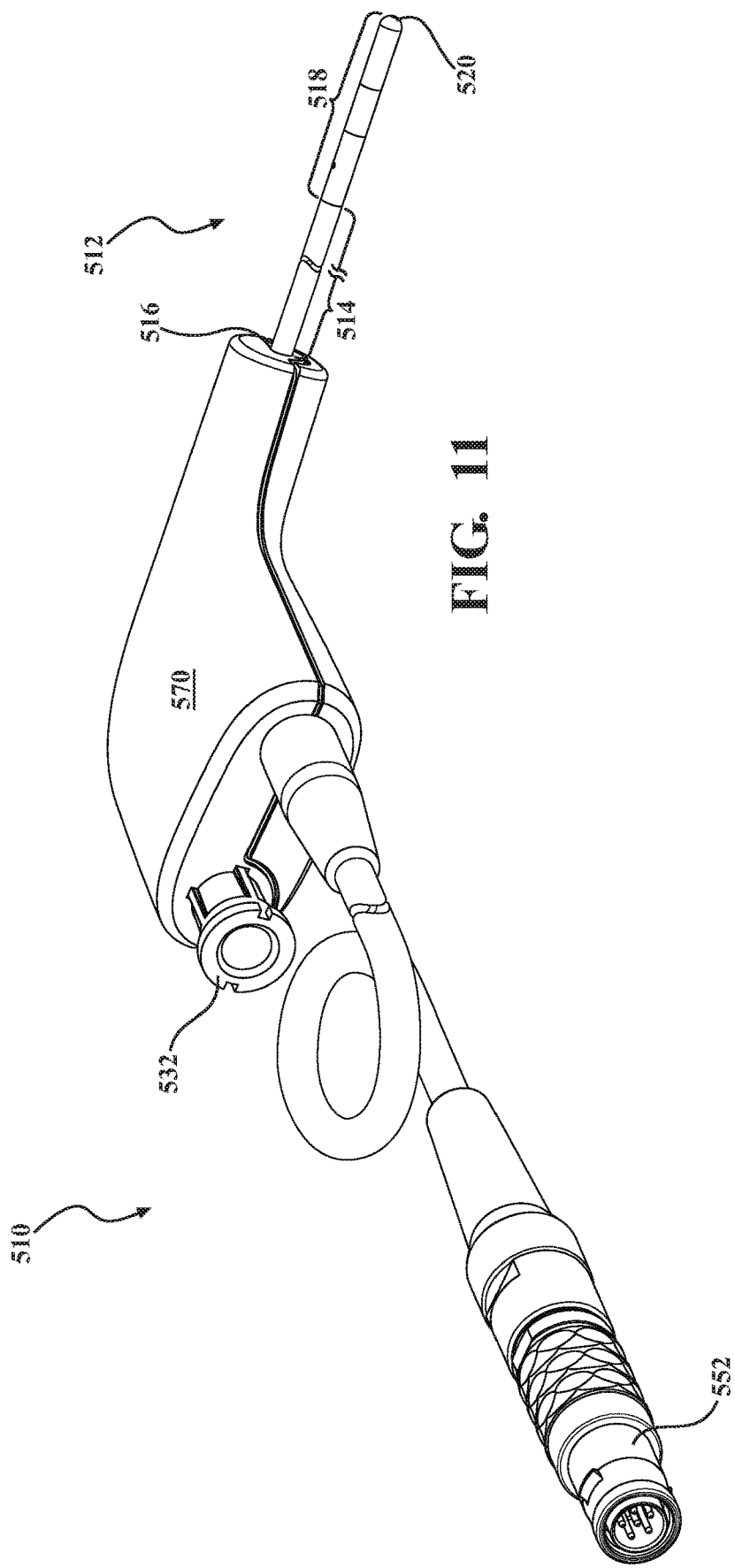
FIG. 11 is a perspective view of an exemplary irrigated electrode assembly that is used to ablate biological tissue.
Figure 12:
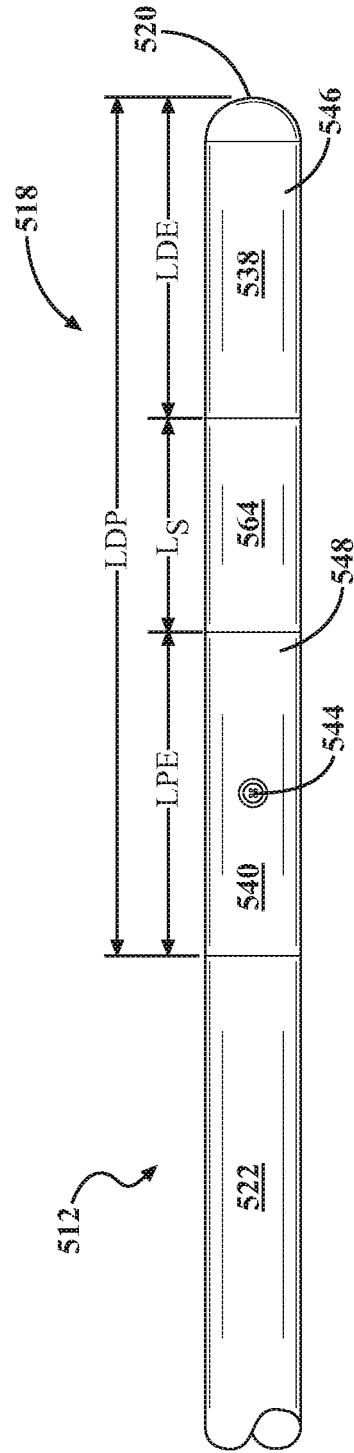
FIG. 12 is a perspective view of a distal portion of the exemplary irrigated electrode assembly of FIG. 11.

An irrigated electrode assembly 512 illustrated in FIGS. 11-17 is configured to supply energy and fluid to targeted biological tissue, before, during, and/or after ablation. The irrigated electrode assembly 512 is also configured to monitor tissue temperature before, during, and/or after ablation. An ablation system 510 including the irrigated electrode assembly 512 is generally shown in FIG. 11.

The irrigated electrode assembly 512 illustrated in FIGS. 11-17 has a proximal portion 514 with a proximal end 516 and a distal portion 518 with a distal end 520. The irrigated electrode assembly 512 includes a first conduit 536 defining an irrigation channel 534 and a second conduit 537 also defining a channel 535, both of which extend from the proximal portion 514 to the distal portion 518 of the irrigated electrode assembly 512. A proximal transfer surface 540 defined by a proximal emitter 548, and a distal transfer surface 538 defined by a distal emitter 546, are located on the distal portion 518 of the irrigated electrode assembly 512 with the distal transfer surface 538 being positioned distally relative to the proximal transfer surface 540. A fluid irrigation port 544 is located on the proximal transfer surface 540 or the distal transfer surface 538 of the irrigated electrode assembly 512 and in fluid communication with the first conduit 536.

The irrigated electrode assembly 512 may include an insulative spacer 564 extending between a distal end of the proximal transfer surface 540 and a proximal end of the distal transfer surface 538. The insulative spacer 564 can be rigid or flexible. The insulative spacer 564 typically comprises a polymer, and may be formed, for example, via molding or extrusion processes known to those skilled in the art. In many non-limiting examples, the insulative spacer 564 comprises a thermoplastic elastomer. In some non-limiting examples, the insulative spacer 564 comprises PEEK. In other non-limiting examples, the insulative spacer 564 comprises silicone. Of course, the insulative spacer 564 functions as an electrical insulator.

The example insulative spacer 564 illustrated in FIGS. 11-17 extends between a distal end of the proximal transfer surface 540 and a proximal end of the distal transfer surface 538, is annular in shape, and defines an intermediate channel. Further, the insulative spacer 564 illustrated in FIGS. 11-17 can be machined from a single piece of PEEK.

The example irrigated electrode assembly 512 illustrated in FIGS. 11-17 includes an insulative body 522 that houses the first and second conduits 536, 537 and extends from the proximal portion 514 of the irrigated electrode assembly 512 to a proximal end of the proximal transfer surface 540. The insulative body 522 of FIGS. 11-17 is in annular in shape and defines a lumen 524. The insulative body 522 can be rigid or flexible. The insulative body 522 typically comprises a polymer, and may be formed, for example, via molding or extrusion processes known to those skilled in the art. The insulative body 522 typically comprises a polymer, and may be formed, for example, via molding or extrusion processes known to those skilled in the art. In many non-limiting examples, the insulative body 522 comprises a thermoplastic elastomer. In some non-limiting examples, the insulative body 522 comprises PEEK. In other non-limiting examples, the insulative body 522 comprises silicone. Of course, the insulative body 522 functions as an electrical insulator.

In many examples, the first conduit 536 that defines the irrigation channel 534 and extends from the proximal portion 514 of the irrigated electrode assembly 512 to the distal portion 518 of the irrigated electrode assembly 512 and comprises an electrically conductive material such as, but not limited to, metal. In some such examples, the first conduit 536 comprises a first insulative sheath 566 disposed thereabout. Of course, the first conduit 536 defines the irrigation channel 534 that is in fluidic communication with a fluid source, e.g. the micro-infusion module, and the fluid irrigation port 544. In should be appreciated that the first conduit 536 can be in fluidic communication with one or more of the fluid irrigation port 544. For example, the first conduit 536 could supply fluid to 1, 2, 3, 4, 5, or more of the fluid irrigation port 544 located on the distal portion 518 of the irrigated electrode assembly 512 (not necessarily on the proximal emitter 548). Although not illustrated in the example of FIGS. 11-17, the second conduit 537 can also be used to house a thermocouple 562.

Figure 17:
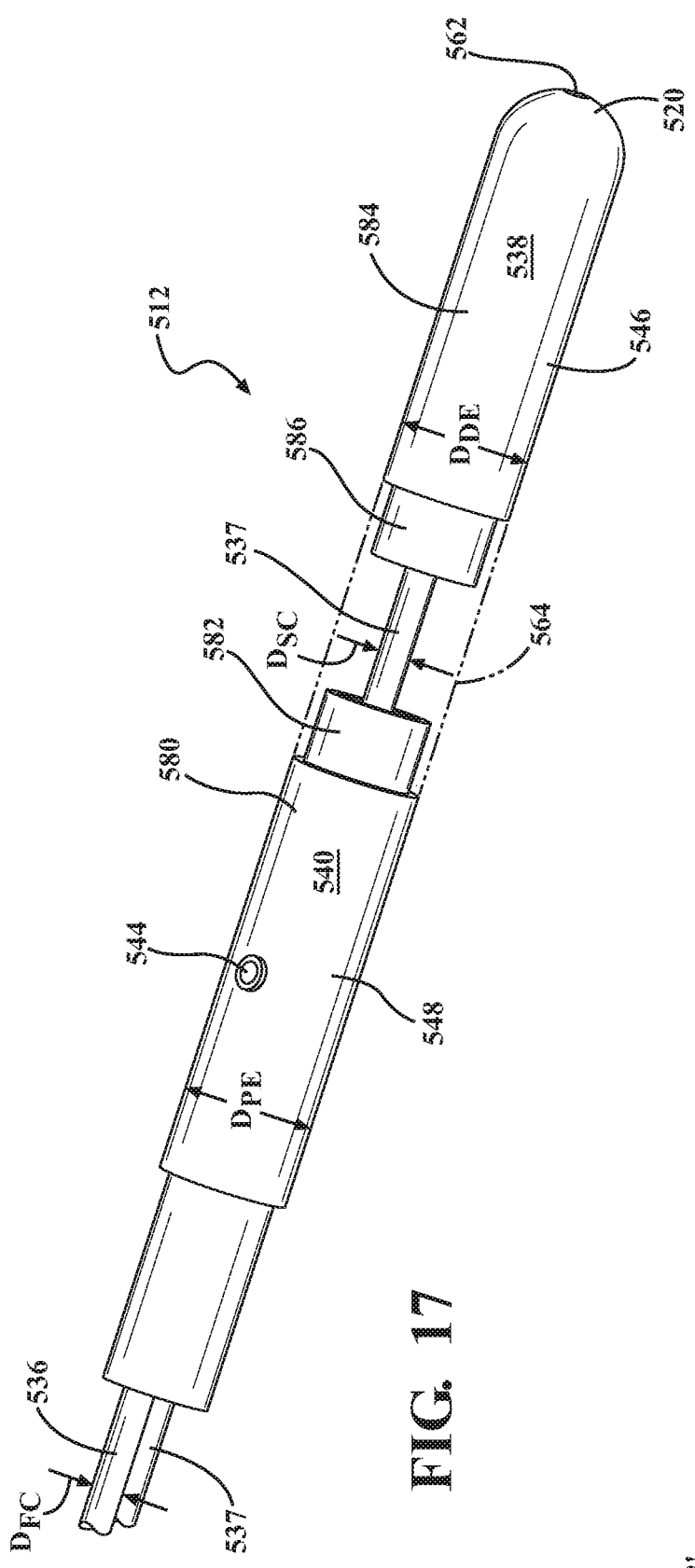
FIG. 17 is a close-up view of the distal portion of the exemplary irrigated electrode assembly of FIG. 11 with an insulative body, an insulative spacer, a first insulative sheath, and a second insulative sheath made transparent.

The irrigated electrode assembly 512 also includes the second conduit 537, which defines the channel 535. In some examples, the second conduit 537 comprises an electrically conductive material such as, but not limited to, metal. In some such examples, the second conduit 537 comprises a second insulative sheath 568 disposed thereabout. In the example of FIGS. 11-17, the thermocouple 562 is housed within and insulated from the second conduit 537. As is best illustrated in FIGS. 16 and 17, the distal transfer surface 538 houses the thermocouple 562 which is configured to measure a temperature of tissue at the distal end 520 of the irrigated electrode assembly 512. Although not shown in the example of FIGS. 11-17, the second conduit 537 can also be used to carry fluid.

The irrigated electrode assembly 512 can include one or more of the thermocouple 562. If included, the one or more of the thermocouple 562 need not be housed in a conduit. The one or more of the thermocouple 562 can be housed in a lumen collectively formed by the insulative body 522, the proximal and distal emitters 548, 546, and the insulative spacer 564. Of course, the thermocouple 562 can be configured to measure a temperature of tissue at the distal end 520, or at various locations on the distal portion 518 of the irrigated electrode assembly 512. For example, the thermocouple 562 can be configured to measure tissue temperature between the proximal transfer surface 540 and the distal transfer surface 538. As another example, the thermocouple 562 can be configured to measure tissue temperature at a location proximal to the proximal transfer surface 540. As is best illustrated in FIG. 17, the thermocouple 562 is insulated from and housed within the channel 535 and terminates at the distal end 20 of the irrigated electrode assembly 512. In this example, the thermocouple 562 is configured to measure a temperature of biological tissue proximal to the distal end 20 of the irrigated electrode assembly 512.

In the example of FIGS. 11-17, the fluid irrigation port 544 is located on the distal transfer surface 538 of the irrigated electrode assembly 512 and in fluid communication with the first conduit 536. The cross-sectional view of FIG. 15 best illustrates the fluid communication between the first conduit 536 and the fluid irrigation port 544 defined by the proximal emitter 548.

In the example of FIGS. 11-17, the irrigated electrode assembly 512 which includes one of the fluid irrigation port 544 defined by the proximal emitter 548 is illustrated. It should be appreciated that the irrigated electrode assembly 512 can include one or more of the fluid irrigation port 544, and that each of the fluid irrigation port 544 included can be located at various locations on the distal portion of the irrigated electrode assembly 512 (e.g. the proximal emitter 548, the distal emitter 546, the insulative spacer 564, the insulative body 522, etc.).

In many examples, the proximal transfer surface 540 is defined by a proximal emitter 548, is located on the distal portion 518 of the irrigated electrode assembly 512 with the distal transfer surface 538 being positioned distally relative to the proximal transfer surface 540. In many examples, the proximal emitter 548 has an outer diameter ($D_{PE}$) that is at least about 33, about 66, or about 100% greater than an outer diameter ($D_{FC}$) of the first conduit 536, and is at least about 33, about 66, or about 100% greater than an outer diameter ($D_{SC}$) of the second conduit 537. A proximal emitter 548 having an outer diameter ($D_{PE}$) that is at least 100% greater than an outer diameter ($D_{FC}$) of the first conduit 536 and an outer diameter ($D_{SC}$) of the second conduit 537 would be at least two times (or twice as big) as the respective conduit. As such, when the irrigated electrode assembly 512 is in use and the proximal end of the proximal transfer surface 540 extends past a distal end of an access cannula, the proximal transfer surface 540 is distinctly visible in tissue with electromagnetic imaging techniques. FIG. 17 is a close-up view of the distal portion of the exemplary irrigated electrode assembly 512 of FIG. 14 with the insulative body 522, an insulative spacer 564, a first insulative sheath 566, and a second insulative sheath 568 made transparent. The removal of these polymeric components helps provide a visualization as to how the distal portion 518 of the irrigated electrode assembly 512 is visible with electromagnetic imaging techniques once the proximal end of the proximal transfer surface 540 extends past the end of an access cannula comprising metal.

The first and second insulative sheaths 566, 568 typically comprise a polymer. In some examples, the polymer is an elastomer or a thermoplastic elastomer. In other examples, the polymer is a thermoplastic. In still other examples, the polymer is a thermoset. The first and second insulative sheaths 566, 568 can be applied to the first and second conduits 536, 537 as shrink wrap via heat, as a pre shaped tubular segments, or even as a coating (i.e. coated on).

The distal transfer surface 538 is typically defined by the distal emitter 546 and located on the distal portion 518 of the irrigated electrode assembly 512 with the distal transfer surface 538 being positioned distally relative to the proximal transfer surface 540. As is illustrated best in the example of FIGS. 13 and 15, the distal emitter 546 can be annular in shape and define a distal channel in communication with the lumen 524 of the insulative body 522, the proximal channel of the proximal emitter 548, and the intermediate channel of the insulative spacer 564. In many examples, the distal emitter 546 has an outer diameter ($D_{DE}$) that is greater than an outer diameter ($D_{FC}$) of the first conduit 536 and an outer diameter ($D_{SC}$) of the second conduit 537. In many examples, the distal emitter 546 has an outer diameter ($D_{DE}$) that is at least 33%, 66%, or 100% greater than an outer diameter ($D_{FC}$) of the first conduit 536 and at least 33%, 66%, or 100% greater than an outer diameter ($D_{SC}$) of the second conduit 537.

As set forth above, in many examples the first and second conduits 536, 537 comprise an electrically conductive material (e.g. metal) in electrical communication with the proximal or the distal transfer surface 540, 538. As such, the first and second conduits 536, 537 can be used to carry energy from an energy source 54 (as previously described) connected to the proximal end of the irrigated electrode assembly 512, to the proximal and distal emitters 548, 546 and through the proximal and distal transfer surfaces 540, 538 and into biological tissue. In the example irrigated electrode assembly 512 of FIGS. 11-17, the first conduit 536 comprises an electrically conductive material and is in electrical communication with the proximal emitter 548 and proximal transfer surface 540 while the second conduit 537 is in electrical communication with the distal emitter 546 and the distal transfer surface 538.

As is illustrated throughout the drawings herein, the proximal and distal transfer surfaces 540, 538 can be isolated by the insulative spacer 564, or even, in some examples, the insulative body 522. In the example of FIGS. 11-17, the proximal and distal transfer surfaces 540, 538 of the proximal and distal emitters 548, 546 are electrically isolated from one another by the insulative spacer 564. Further, in some examples, the first conduit 536 and/or the second conduit 537 may have the first or the second insulative sheath 566, 568 disposed thereabout, which electrically isolates the first and second conduits 536, 537 from one another.

As such, the first and second conduits 536, 537 can be multi-functional. In the example of FIGS. 11-17, the first conduit 536 is used to carry energy to and from an energy source to the proximal emitter 548 and also to carry fluid from a fluid source such as the micro-infusion module to the fluid irrigation port 544. In the example of FIGS. 11-17, the second conduit 537 is used to carry energy to and from an energy source to the distal emitter 546 and also to carry the thermocouple 562 to the distal end of the electrode assembly. Of course, various examples of the multi-functional conduits in addition to those specifically disclosed herein are contemplated. The irrigated electrode assembly 512 disclosed can include 1, 2, 3, 4, 5, or more conduits that carry energy transport, fluid, and/or the thermocouple 562 various locations on the distal portion of the irrigated electrode assembly 512. In other words, the irrigated electrode assembly 512 can include one or more conduits having at least one functionality selected from: fluid delivery; energy delivery; and temperature measurement. In one example, a tri-functional conduit may carry energy, fluid, and a thermocouple to the distal portion 518 of the irrigated electrode assembly 512.

The proximal portion of the irrigated electrode assembly 512 includes at least one of a fluid intake port 532 and at least one of an electrical connector 552. In the example of FIG. 11, the irrigated electrode assembly 512 includes a pistol grip 570 comprising the fluid intake port 532 and the electrical connector 552.

Referring back to FIG. 11, the electrical connector coupled to a flexible conductor (e.g. wire) is mounted to the pistol grip 570. The electrical connector is connected to the energy source 54, e.g. an electrosurgical generator. In the example irrigated electrode assembly 512 of FIGS. 11-17, energy supplied to the irrigated electrode assembly 512 by the energy source travels through the electrical connector, along the flexible conductor, further along the first and second conduits 536, 537, into the proximal and distal emitters 548, 546, and through the proximal and distal transfer surfaces 540, 538 and into biological tissue. To this end, the energy source, the electrical connector, the flexible conductor, the first conduit 536, and the proximal emitter 548 are in electrical communication with one another and the energy source, the electrical connector, the flexible conductor, the second conduit 537, and the distal emitter 546 are in electrical communication with one another. During ablation an electrical circuit is formed as energy moves through the flesh adjacent to and between the proximal and distal transfer surfaces 540, 538.

The electrical circuit through the biological tissue produces resistive heating within the tissues surrounding the irrigated electrode assembly 512. Because biological tissue is a poor conductor of electricity, current flowing through tissues leads to ionic agitation and production of frictional heat. The step of discharging (or the micro infusion) of fluid, e.g. saline, helps control the temperature of the biological tissue to ensure effective ablation of the biological tissue. During ablation, irrigation of biological tissue with the micro infusion of fluid (e.g. saline or other conductive fluid) increases conductivity of the biological tissue and helps control temperature of the biological tissue thereby preventing charring of biological tissue and thus generally helps control the area and quality of the ablation while using the irrigated electrode assembly 512.

In many examples, the irrigated electrode assembly 512 is flexible. For example, the insulative body 522 is configured to have sufficient flexibility as to be deployed through an access cannula having a curve of greater than 90 degrees. As such, the insulative body 522 is often formed from a flexible, insulative polymer such as, but not limited to, PEEK. Further, the distal portion 518 of the irrigated electrode assembly 512 is flexible. For example, the distal portion 518 is flexibly configured to be deployed into tissue at an angle of approach relative to the tissue. The flexibility of the irrigated electrode assembly 512 and the distal portion 518 thereof allows for better positioning and more effective use (location and ablation) of the irrigated electrode assembly 512.

Figure 13:
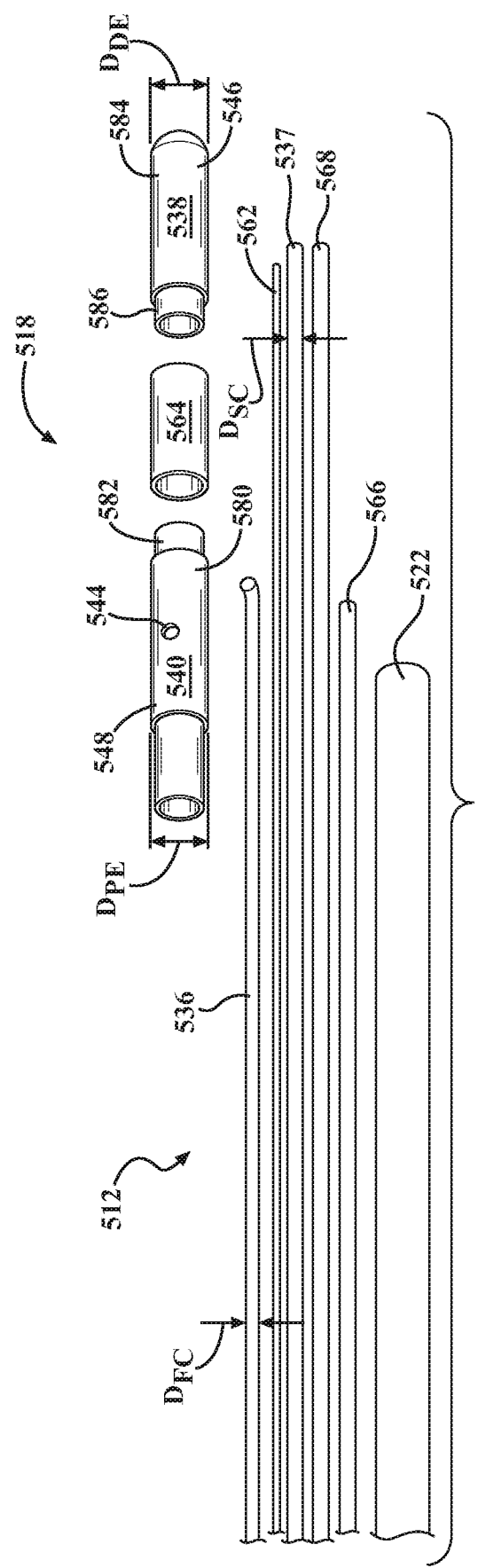
FIG. 13 is an exploded view of the exemplary irrigated electrode assembly of FIG. 11.

The construction of the distal portion 518 of the irrigated electrode assembly 512 provides flexibility. In many examples the irrigated electrode assembly 512 is configured to be deployed into tissue at an angle of approach relative to the tissue. In the example of FIGS. 11-17, as is best illustrated in FIGS. 13 and 17, the proximal emitter 548 comprising a proximal emitter annular body 580 that has an outer diameter complementary to an outer diameter of the insulative body 522 and the insulative spacer 564. A distal shoulder 582 extends from the proximal emitter annular body 580 and has an outer diameter less than the outer diameter of the proximal emitter annular body 580. The distal emitter 546 comprises a distal emitter annular body 584 that has an outer diameter complementary to the insulative spacer 564, and a proximal shoulder 586 extending from the distal emitter annular body 584 and having an outer diameter less than the outer diameter of the distal emitter annular body 584. In some such examples, a length of the proximal shoulder 586 is less than a length of the distal shoulder 582, which provides a tip portion of the irrigated electrode assembly 512 with increased flexibility. In this example, the proximal and distal emitters 548, 546 can be coupled with the insulative spacer 564 via a friction fit and, optionally, an adhesive can be used to couple the insulative spacer 564 to each of the proximal and distal emitters 548, 546 along respective lengths of the friction fit. In this example, the proximal emitter 548 may also comprise a threaded fitting configured to engage a complementary threaded fitting on the insulative body 522 (not shown in FIGS. 11-17).

Figure 18:
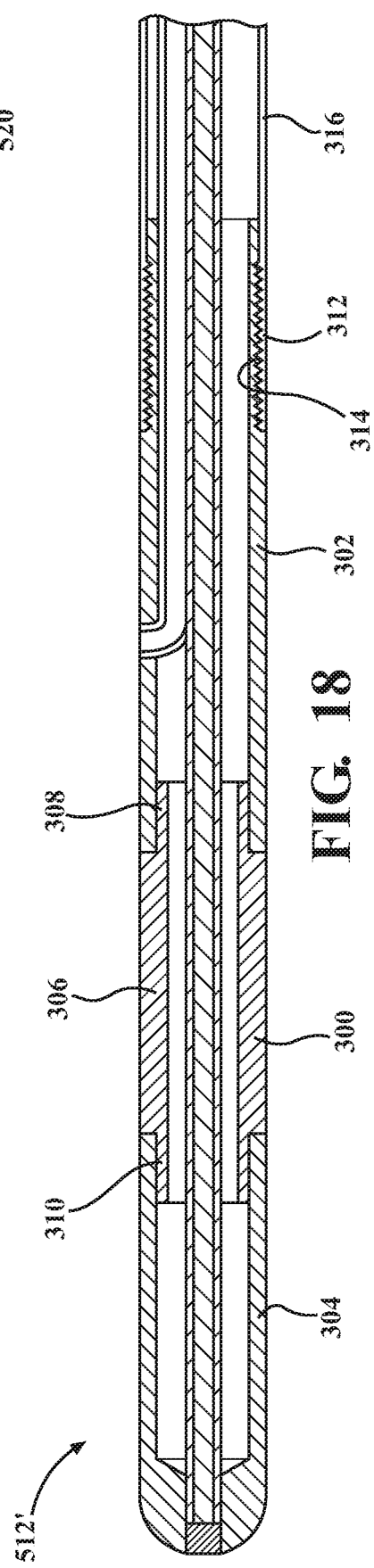
FIG. 18 is a cross-sectional view of a distal portion of an exemplary irrigated electrode assembly.

Referring now to FIG. 18, the irrigated electrode assembly 512' includes the insulative spacer 300 that extends between the proximal emitter 302 and the distal emitter 304 and comprises a spacer annular body 306 that has an outer diameter complementary to the proximal and distal emitters 302, 304. A proximal shoulder 308 extending from the spacer annular body 306 and having an outer diameter less than the outer diameter of the spacer annular body 306 so as to be coupled to the proximal emitter 302 via a friction fit. Further, a distal shoulder 310 extends from the spacer annular body 306 in a direction opposite the proximal shoulder 308, the distal shoulder 310 having an outer diameter less than the outer diameter of the spacer annular body 306 so as to be coupled to the distal emitter 304 via friction fit. In the example of FIG. 18 illustrated, a length of the distal shoulder 310 is the same as a length of the proximal shoulder 308. However, in some examples, a length of the distal shoulder 310 is less than a length of the proximal shoulder 308. In other examples, a length of the distal shoulder 310 is greater than a length of the proximal shoulder 308. That is, in various examples, a length of the insulative spacer 300 and its shoulders 308, 310, a length of the proximal emitter 302, and/or a length of the distal emitter 304, can be modified to adjust the flexibility of the distal portion of the irrigated electrode assembly 512'. For example, in the insulative spacer 300 of FIG. 18 could be modified such that a length of the distal shoulder 310 is less than a length of the proximal shoulder 308 to create more flexibility at a distal tip of the irrigated electrode assembly 512'. In this example, the proximal emitter 302 comprises a threaded fitting 312 configured to engage a complementary threaded fitting 314 on the insulative body 316. An adhesive can be utilized to further couple the insulative spacer 300 to each of the proximal and distal emitters 302, 304 along respective lengths of the friction fit.

Figure 19:
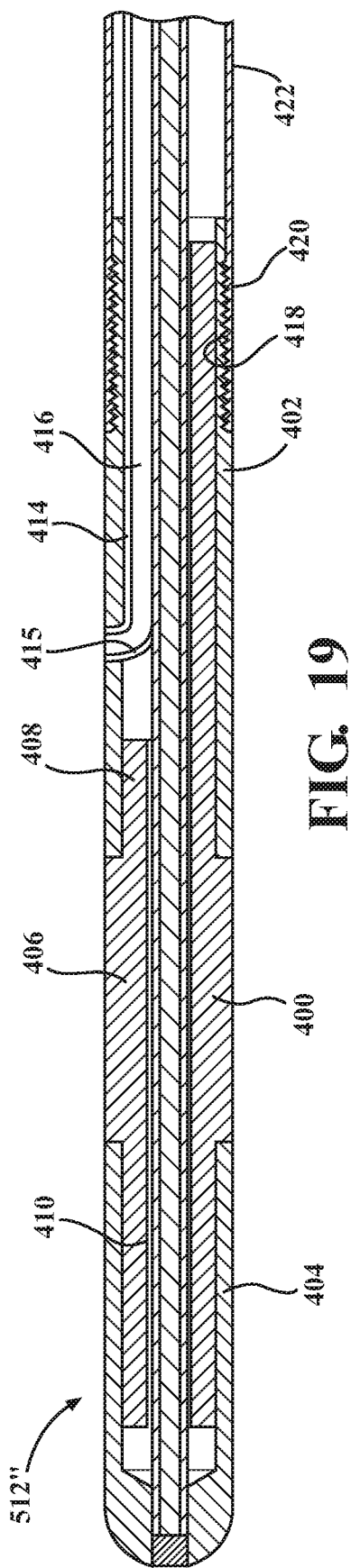
FIG. 19 is a cross-sectional view of a distal portion of an exemplary irrigated electrode assembly.
Figure 20:
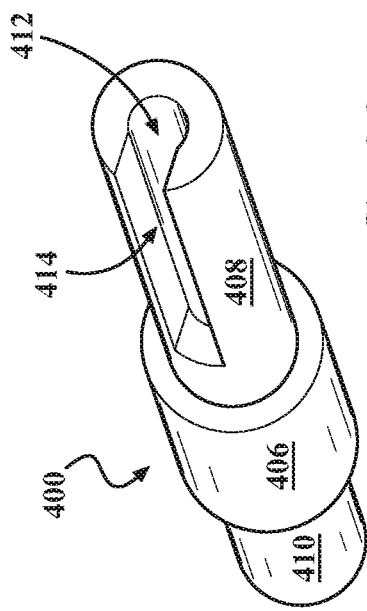
FIG. 20 is an enlarged, isolated view of an insulative spacer of the distal portion of FIG. 19.

Referring now to FIGS. 19 and 20, the irrigated electrode assembly 512" includes an insulative spacer 400 that extends between a proximal emitter 402 and a distal emitter 404. The insulative spacer 400 comprises (i) a spacer body 406, (ii) a proximal shoulder 408 having an outer diameter less than an outer diameter of the spacer body 406, and (iii) a distal shoulder 410 having an outer diameter less than the outer diameter of the spacer body 406, and (iv) a bore 412 extending through the insulative spacer 400, (v) a slot 414 extends longitudinally within the proximal shoulder 408 and is in communication with the bore 412. In this example, the first conduit 416 extends through a lumen of an insulative body 422 and comprises a bend 415 disposed within the slot 414. In this example, the proximal emitter 402 comprises a threaded fitting 418 configured to engage a complementary threaded fitting 420 on the insulative body 422.

Figure 21:
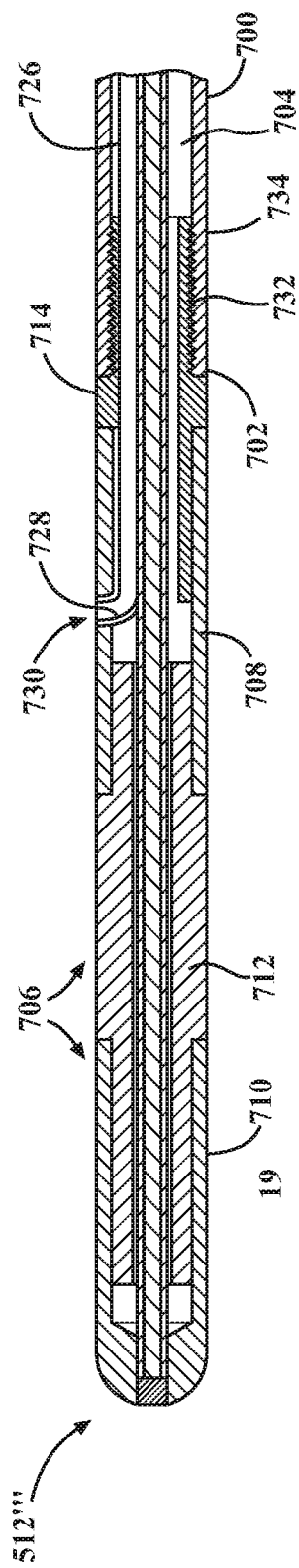
FIG. 21 is a cross-sectional view of a distal portion of an exemplary irrigated electrode.
Figure 22:
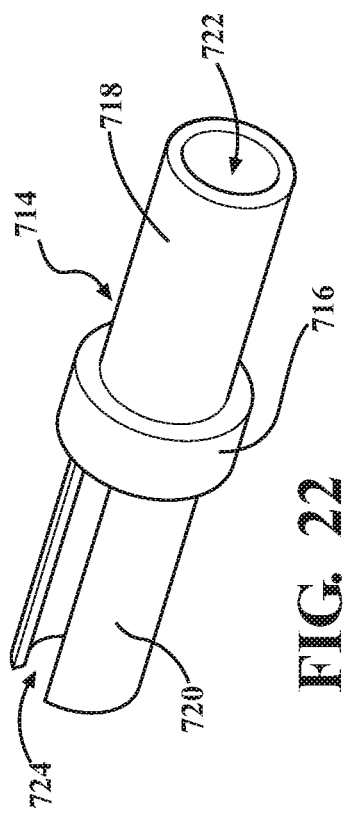
FIG. 22 is an enlarged, perspective view of an adapter of the distal portion of FIG. 21.

Referring now to FIGS. 21 and 22, the irrigated electrode assembly 512''' comprises an insulative body 700 having a proximal end opposite a distal end 702 and defines a lumen 704 there between. A bipolar electrode 706 is coupled to the distal end 702 of the insulative body 700. The bipolar electrode 706 comprises: a proximal emitter 708; a distal emitter 710; an insulative spacer 712 extending between the proximal emitter 708 and the distal emitter 710; and an adapter 714. The adapter 714 comprises (i) an adapter body 716, (ii) a proximal shoulder 718 having an outer diameter less than an outer diameter of the adapter body 716, and (iii) a distal shoulder 720 having an outer diameter less than the outer diameter of the adapter body 716 and coupled with the insulative body 700, and (iv) a bore 722 extending through the adapter 714, (v) an adapter slot 724 extending longitudinally within the distal shoulder 720 and in communication with the bore 722. A first conduit 726 extends through the lumen 704 of the insulative body 700 and the at least a portion of the bore 722. The first conduit 726 comprises a bend 728 disposed within the adapter slot 724, the first conduit 726 also comprises a discharge port 730 within the proximal emitter 708, wherein the first conduit 726 is configured to be arranged in fluid communication with an irrigation source (such as the micro infusion modules described below) to deliver fluid adjacent to the proximal emitter 708. In this example, the proximal emitter 708 comprises a threaded fitting 732 configured to engage a complementary threaded fitting 734 on the insulative body 700.

In some examples such as those of FIGS. 18-22, the proximal emitter 548 comprises a threaded fitting configured to engage a complementary threaded fitting on the insulative body 522. In such examples, an adhesive coupling can be used to thread the fitting and the complementary threaded fitting together.

Referring now to FIGS. 23A-23C, the irrigated electrode assembly 512" includes an insulative spacer 800 that extends between a proximal emitter 802 and a distal emitter 804. FIG. 23A is a first cross-sectional view of a distal portion of the irrigated electrode assembly 512"''', while FIG. 23B is a second cross-sectional view (rotated 180° relative to the view of FIG. 8A) and FIG. 23C is an isolated view of the insulated spacer 800 of the irrigated electrode assembly 512"''. The insulative spacer 800 comprises (i) a spacer body 806, (ii) a proximal shoulder 808 having an outer diameter less than an outer diameter of the spacer body 806, and (iii) a distal shoulder 810 having an outer diameter less than the outer diameter of the spacer body 806, and (iv) a bore 812 extending through the insulative spacer 800, (v) a slot 814 extends longitudinally within the proximal shoulder 808 and is in communication with the bore 812. In this example, the first conduit 816 extends through a lumen of an insulative body 822 and comprises a bend 815 disposed within the slot 814. In this example, the insulative spacer 800 is configured to engage the insulative body 822 directly via a friction fit and/or adhesive. That is, the proximal emitter 802 defines a proximal channel 824 with the proximal shoulder 808 disposed within the proximal channel 824 and extending proximally to a distal end 826 of the proximal emitter 802, wherein the proximal shoulder 808 is coupled directly to the insulative body 822.

Still referring now to FIGS. 23A-23C, this example insulative spacer 800 design is advantageous because when the irrigated electrode assembly 512 is in use and the proximal end of the proximal transfer surface of the proximal emitter 802 extends past a distal end of an access cannula, the proximal transfer surface 540 is immediately distinctly visible in tissue with electromagnetic imaging techniques since a proximal shoulder to mount the insulative body 822 to the proximal emitter 802 is not required and the length of the proximal emitter 802 is reduced.

The irrigated electrode assembly 512 comprises the insulative body 522 that defines a lumen 524, the proximal emitter 548 defines a proximal channel, the insulative spacer 564 defines and intermediate channel, and the distal emitter 546 defines a distal channel. These components together form an assembly lumen that extends from a proximal end of the irrigated electrode assembly 512 to a distal end of the irrigated electrode assembly 512. A distal end of the assembly lumen can be partially or completely filled with a polymeric filler or potting compound that can function to adhere the components of the assembly together, to isolate the components of the assembly from one another, and to prevent the uptake of water, moisture, and corrosive agents materials into the irrigated electrode assembly 512. The polymeric filler can be selected to be durable and flexible to maintain the flexibility of the irrigated electrode assembly 512.

Referring back to FIG. 11, the fluid intake port 532 is mounted on the pistol grip 570. The fluid source (e.g. the microfluidic module described herein) is connected to the fluid intake port 532. In the example irrigated electrode assembly 512 of FIGS. 11-17, fluid supplied to the irrigated ablation assembly by the fluid source travels through a conduit in the pistol grip 570, into the first conduit 536 and through the irrigation channel 534, out of the fluid irrigation port 544 defined by the proximal emitter 548 and into the flesh that is to be ablated or is being ablated. To this end, the fluid source, the fluid intake port 532, the first conduit 536 (or the irrigation channel 534 defined thereby), and the fluid irrigation port 544 are in fluid communication.

Also, during ablation, the temperature of the biological tissue being ablated can be monitored with the irrigated electrode assembly 512. The temperature of the biological tissue can be used to adjust the energy input into the irrigated assembly during ablation, adjust the fluidic irrigation during the ablation, determine if the ablation is complete, and for other purposes. To this end, temperature of the biological tissue can be collected, tracked, and/or monitored with the thermocouple 562 before, during, and after use of the irrigated electrode assembly 512. Referring back to FIG. 11, the thermocouple 562 is insulated and housed in the second conduit 537, which protects and isolates the thermocouple 562 that terminates at the distal end of the irrigated electrode assembly 512. Since, in many examples, the distal portion of the irrigated electrode assembly 512 is flexible, the second conduit 537 physically and electrically protects the thermocouple 562. In some examples, the thermocouple 562 is exposed on the distal portion 518 of the irrigated electrode assembly 512. In the example of FIGS. 11-17, the thermocouple 562 is exposed at the distal end 520 of the irrigated electrode assembly 512.

In many of the examples described above, a length $L_{DP}$ of the distal portion 18, 518 can be measured from the distal end 20, 520 of the irrigated electrode assembly 12, 512 to a proximal end 16, 516 of the proximal emitter 48. Measured as such, the length $L_{DP}$ of the distal portion 18, 518 is typically from about 5 to about 30, from about 10 to about 25, or from about 13 to about 22, mm. In most examples, a cumulative length $L_C$ of the distal and proximal emitters 46, 546, 48, 548 is shorter than a length of the distal portion 18, 518 of the irrigated electrode assembly 12, 512. The cumulative length $L_C$ of the distal and proximal emitters 46, 546, 48, 548 is defined as a length $L_{DE}$ of the distal emitter 46, 546 plus a length $L_{PE}$ of the proximal emitter 48, 548. In some examples, $0.50 \ L_{DP} \geq L_{DE} \geq 0.25 \ L_{DP}$ or $0.50 \ L_{DP} \geq L_{DE} \geq 0.33 \ L_{DE}$, and $0.50 \ L_{DP} \geq L_{PD} \geq 0.25 \ L_{DP}$ or $0.50 \ L_{DP} \geq L_{PD} \geq 0.33 \ L_{DP}$. Alternatively, in some examples a length $L_I$ of the irrigated electrode assembly 12, 512 in between the distal and proximal emitters 46, 546, 48, 548 is less than the length $L_{PE}$ of length $L_{DE}$ of the distal emitter 46 ($L_I < L_{DE}$) and/or the length $L_I$ of the irrigated electrode assembly 12, 512 in between the distal and proximal emitters 46, 546, 48, 548 is less than a length $L_{PE}$ of the proximal emitter 48, 548 ($L_I < L_{PE}$). $L_{DE}$ and $L_{PE}$ can be the same or different. In various non-limiting embodiments, all values and ranges of values including and between those described above are hereby expressly contemplated for use herein.

The irrigated electrode assembly 12, 512 can be used with a fluid source or a micro infusion source such as a micro infusion module 100, 600 an example of which is generally shown in FIGS. 24-35. In some examples, the micro infusion module 100, 600 is sized to be held by a single hand.

Figure 24:
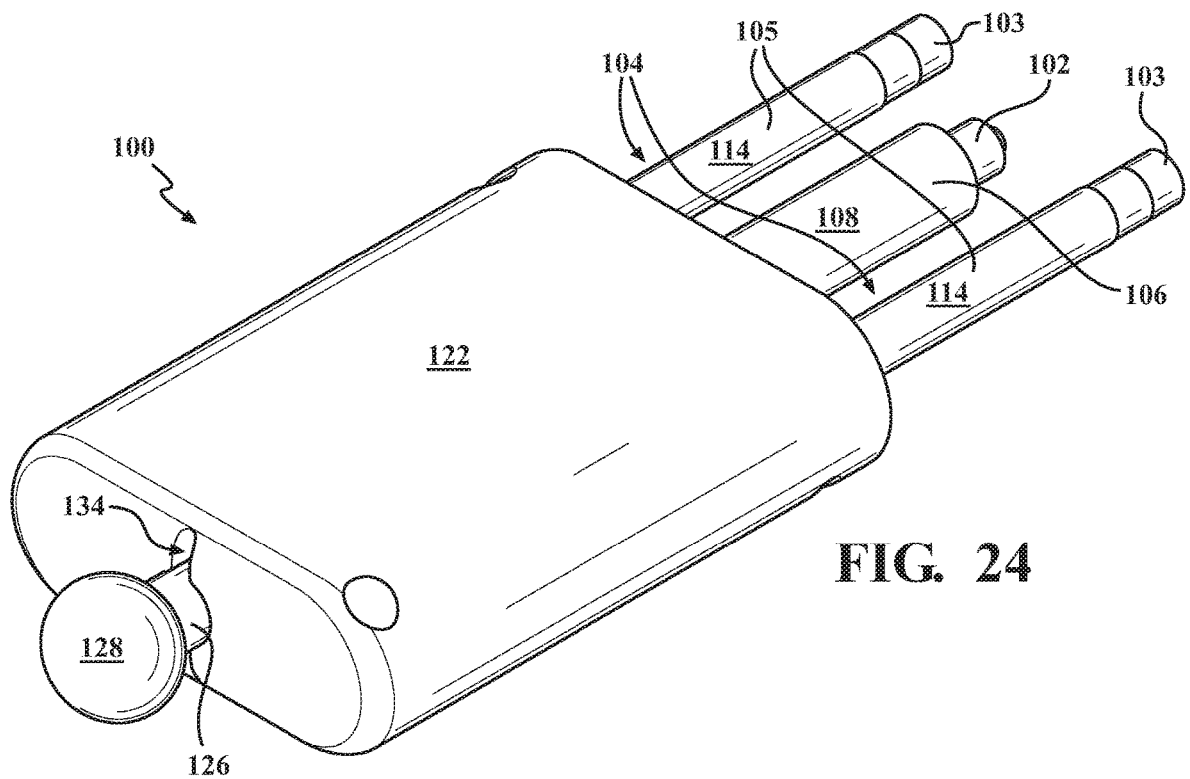
FIG. 24 is a perspective view of an exemplary micro infusion module.
Figure 25:
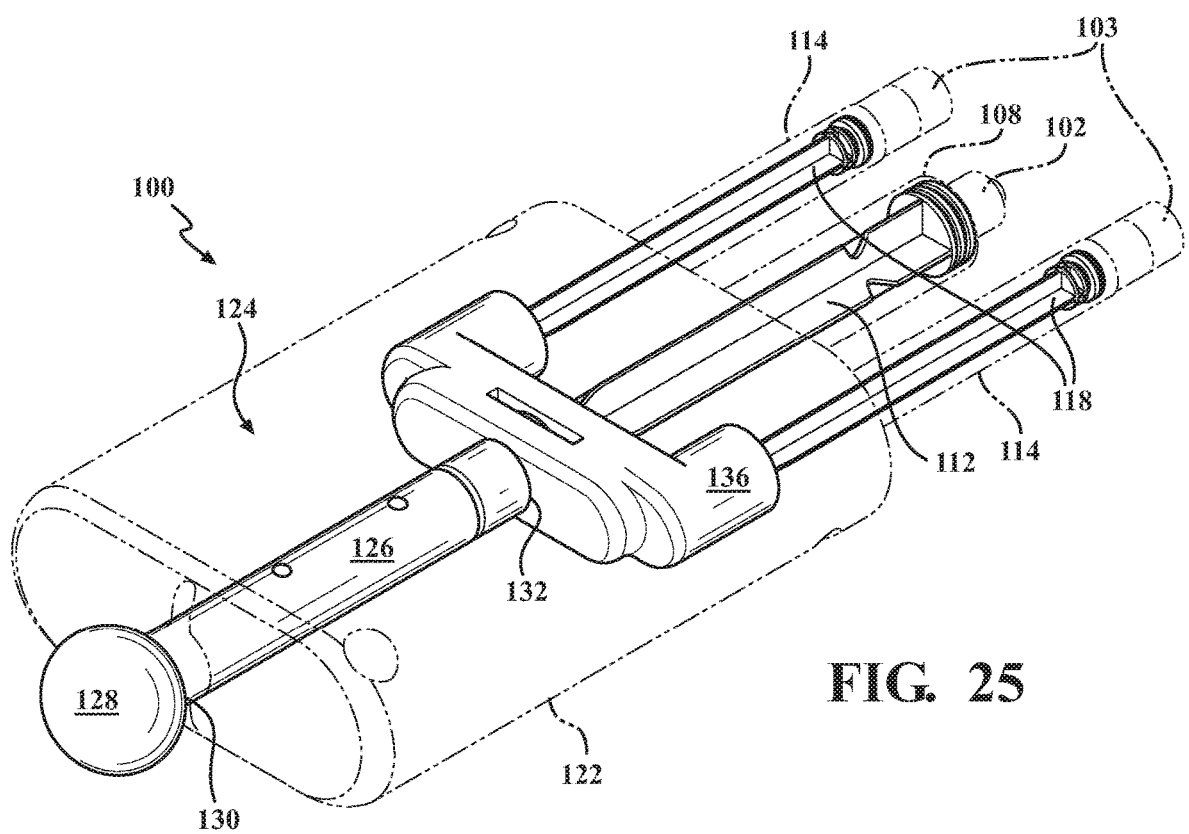
FIG. 25 is a perspective view of the micro infusion module of FIG. 22 with a shell made transparent to illustrate an actuation shaft and an actuation lever movably disposed therein, a fluid delivery actuator having a fluid body made transparent to illustrate a fluid reservoir with a fluid piston moveably disposed therein, and the two vacuum accumulators having vacuum bodies made transparent to illustrate vacuum chambers having a vacuum pistons moveably disposed therein.

Referring now to FIG. 24, the micro infusion module 100 is shaped or configured to be releasably coupled to the irrigated electrode assembly 12, 512. The micro infusion module 100 can be releasably coupled to the irrigated electrode assembly 12 with a fluid coupling 102, such as a luer lock fitting. More particularly, the micro infusion module is configured to be placed in fluid communication with the irrigated electrode assembly 12, 512 described above such that fluid provided from the micro infusion module 100 exits the irrigated electrode assembly through the proximal and/or distal outlet openings.

Although FIG. 1 shows the irrigated electrode assembly 12 having two of the fluid intake port 32, and the micro infusion module 100 illustrated in FIG. 24 includes one of the fluid coupling 102, it should be appreciated that various examples of the irrigated electrode assembly 12 may include one port which can be split into the two conduits 36. Of course, the two conduits can have the same or different flow rate (e.g. flow rate within the channels can be engineered at the split, by the design of the components of the irrigated electrode assembly 12, via flow restrictors 33, etc.). In other examples, two micro infusion modules 100 can be used with the irrigated electrode assembly 12.

The micro infusion module 100 includes at least one potential energy accumulator 104, e.g. at least one vacuum accumulator 105 or a biasing element such as a spring, and at least one fluid delivery actuator 106. The potential energy accumulator 104 is configured to accumulate and store potential energy, while the at least one fluid delivery actuator 106 cooperates with the vacuum accumulator 105 and is configured to accumulate, hold, and controllably release fluid. In the illustrated configuration, the micro infusion module 100 includes the at least one vacuum accumulator 105. In the example of FIGS. 24-27, the micro infusion module 100 is sized to be held by a single hand and includes two vacuum accumulators 105 and one fluid delivery actuator 106.

The micro infusion module 100 can include multiple potential energy accumulators 104 (vacuum accumulators) and/or multiple fluid delivery actuators 106. The exemplary micro infusion modules 100, 100' of FIGS. 24 and 28 include dual potential energy accumulators 104, 104' a single fluid delivery actuator 106, 106'.

Figure 29:
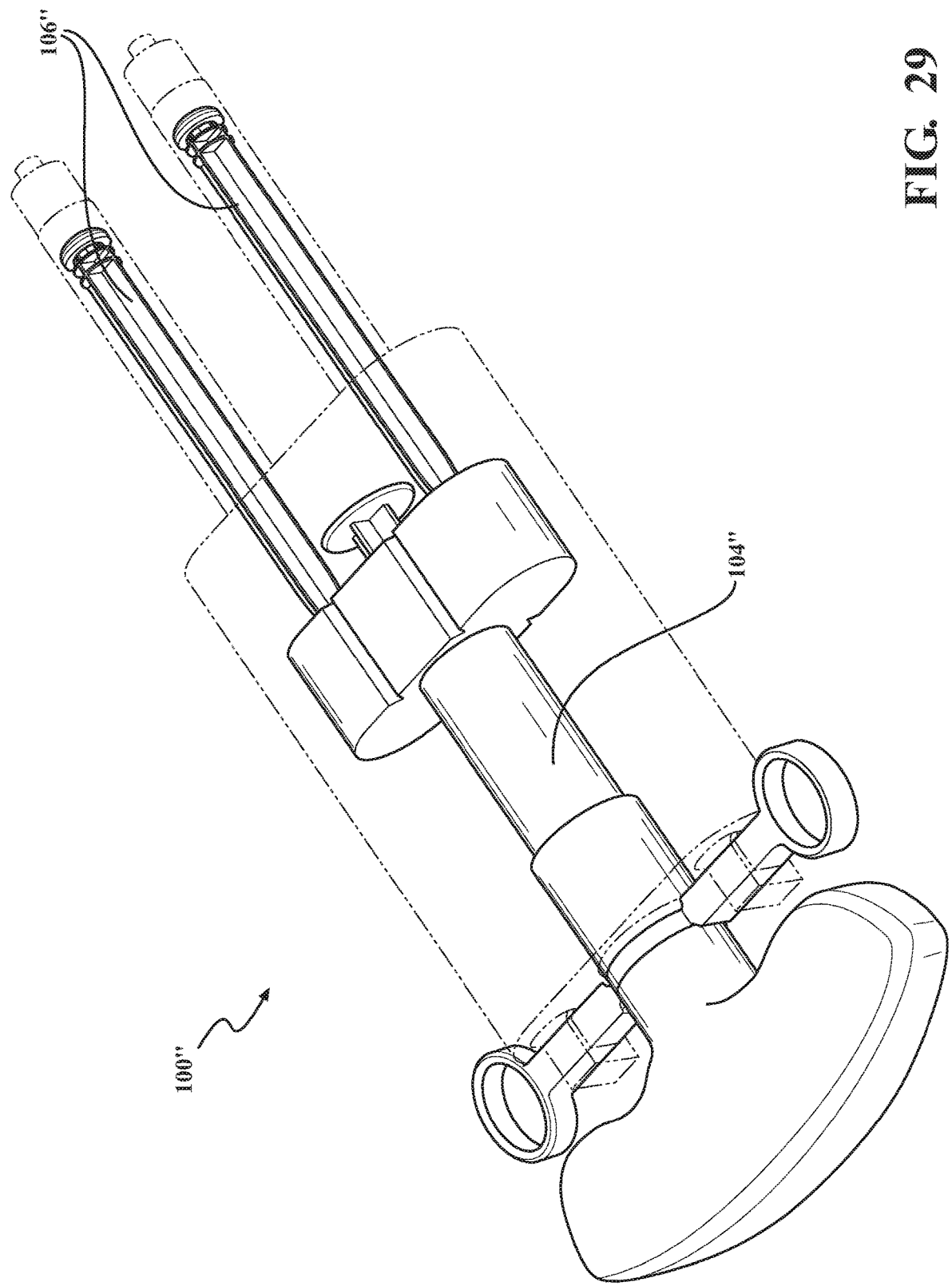
FIG. 29 is a perspective view of yet another example of a micro infusion module with a shell made transparent to illustrate an actuation shaft and an actuation linkage movably disposed therein.

The exemplary micro infusion module 100" of FIG. 29 includes a single potential energy accumulator 104" (vacuum accumulator) and dual fluid delivery actuators 106". This example micro infusion module 100' can be used to supply each of a first and a second fluid intake ports 32a, 32b, which respectively feed the distal and the proximal fluid irrigation ports 44, 42 of the exemplary irrigated electrode assembly 12 of FIG. 1. In such a configuration, the two fluid delivery actuators 106" should be electrically isolated from one another. This can be achieved by constructing the fluid delivery actuators 106" out of an insulative material. Alternatively, the fluid delivery actuators 106" may be mounted in such a way that they are electrically isolated from each other.

The fluid delivery actuator 106 comprises a fluid body 108 defining a fluid reservoir 110 and a fluid piston 112 moveably disposed in the fluid reservoir 110. The fluid coupling 102 may be located at a distal end of the fluid delivery actuator 106. In some examples, the fluid delivery actuator feeds into a flexible infusion line on which any of the following may be included: a stop clamp, a flow restrictor, a gas vent, and the fluid coupling. The vacuum accumulator 105 comprises a vacuum body 114 defining a vacuum chamber 116 and a vacuum piston 118 moveably disposed in the vacuum chamber 116. Typically, a cap 103 is located at a distal end of the vacuum accumulator 105. When uncoupled from the irrigated electrode assembly 12, the fluid delivery actuator 106 is configured to be releasably coupled to a fluid supply (not illustrated), e.g. an I.V. fluid bag, a sterilized fluid vial, etc. In this example, the fluid delivery actuator 106 includes the fluid coupling 102 (e.g. a luer lock coupling, a slip tip coupling, an eccentric tip coupling, a catheter tip coupling, etc.) which releasably connects to a corresponding connector on the fluid supply and also releasably connects one or more of the fluid intake port 32 the fluid delivery actuator 106. That is, the micro infusion module 100 which is shaped or configured to be releasably coupled the fluid supply (to load fluid) or coupled to the fluid intake port 32.

When the micro infusion module 100 is coupled to the fluid supply, the micro infusion module is configured to simultaneously fill the fluid reservoir 110 within the fluid delivery actuator 106 and store potential energy in the vacuum accumulators 105 via the application of force.

When the micro infusion module 100 is coupled to the irrigated electrode assembly 12, 512, the vacuum accumulator 105 and the fluid delivery actuator 106 are in fluidic communication with the at least one irrigation channel 34 and the fluid irrigation ports 42, 44, and the vacuum accumulator 105 and the fluid delivery actuator 106 are configured to release potential energy and in turn to actuate the fluid piston 112 and discharge fluid from the fluid reservoir 110 and into the one or more irrigation channels 34 and out of the proximal and a distal fluid irrigation port 44, 42.

Referring now to FIGS. 24-27, the exemplary micro infusion module 100 also includes a shell 122 defining a void 124 and an actuation shaft 126 having a proximal end 130 and a distal end 132 and movably disposed in the shell 122. A handle 128 is located on the proximal end 130 of the actuation shaft 126. The handle 128 is located past a proximal end of the shell, i.e., the handle 128 is exterior the shell (is not within the void 124 of the shell 122). A proximal portion of the actuation shaft 126 is disposed in an opening 134 in the distal end of the shell 122 and an actuation linkage 136 is coupled to the actuation shaft 126. The actuation linkage 136 is operably connected to the fluid piston 112 of the at least one fluid delivery actuator 106 while a proximal end of the fluid body 108 of the at least one fluid delivery actuator 106 is connected to the shell 122. The actuation linkage 136 is also operably connected to the vacuum piston 118 of the vacuum accumulator 105 and the vacuum body 114 of the at least one vacuum accumulator 105 is connected to the shell 122. In this example, the actuation linkage 136, which is substantially perpendicular to the actuation shaft 126, is operably connected to a single centrally located fluid delivery actuator 106 and two vacuum accumulators 105 spaced equidistant from a side of the single fluid delivery actuator 106. However, other spacing of the fluid delivery actuator 106 and the vacuum accumulators 105 are also contemplated.

Figure 26:
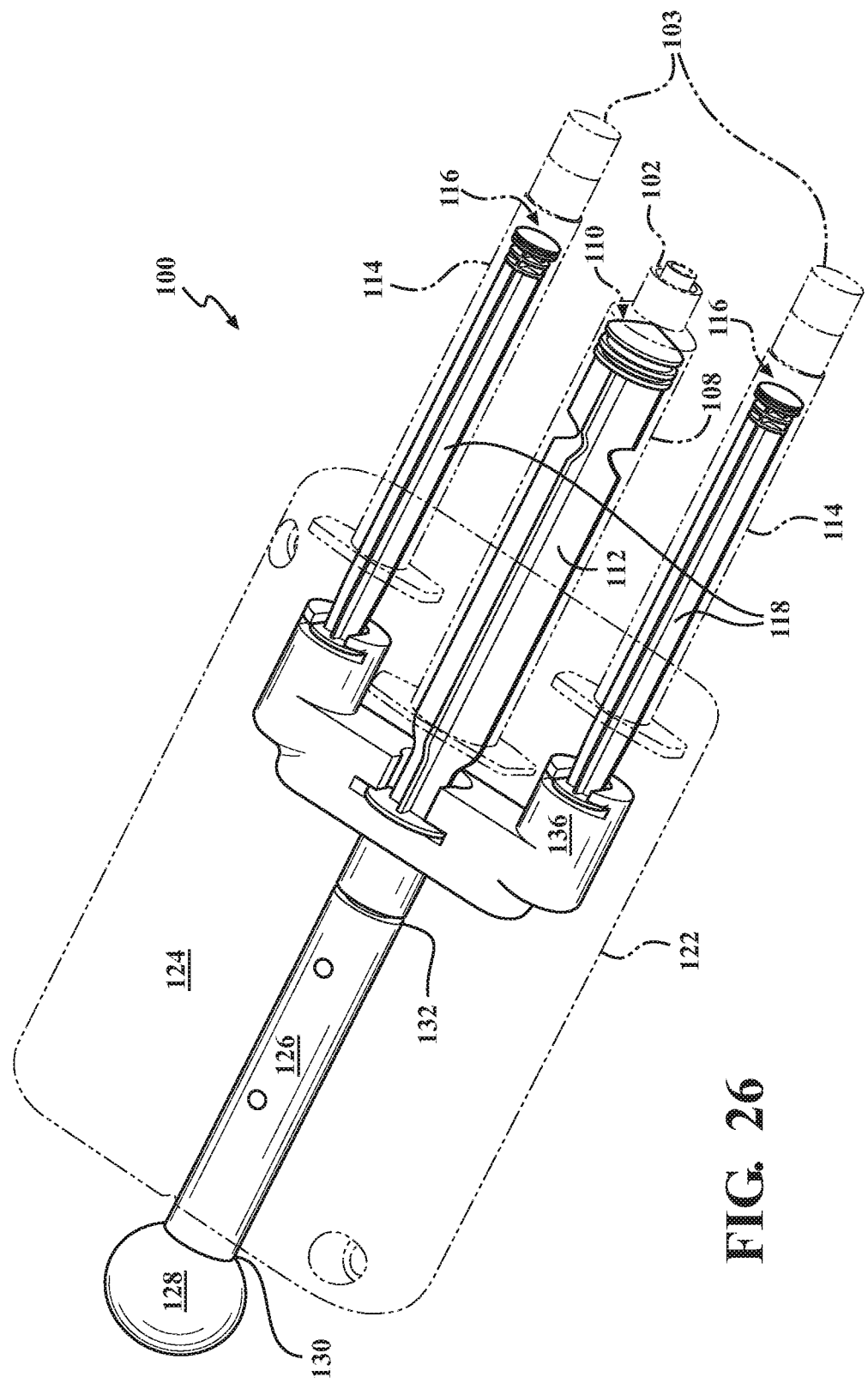
FIG. 26 is a perspective view of the micro infusion module of FIG. 22 which illustrates the micro infusion module in an unloaded position wherein a fluid reservoir and vacuum chambers are empty.

As such, the handle 128, the actuation shaft 126, the actuation linkage 136, the fluid piston(s) 112, and the vacuum piston(s) 118 are all moveably mounted to the shell 122. FIG. 26 illustrates the handle 128, the actuation shaft 126, the actuation linkage 136, the fluid piston(s) 112, and the vacuum piston(s) 118 relative to the shell 122 in an unloaded position. In the unloaded position, the fluid reservoir 110 and the vacuum chambers 116 are empty and are at ambient pressure.

Figure 27:
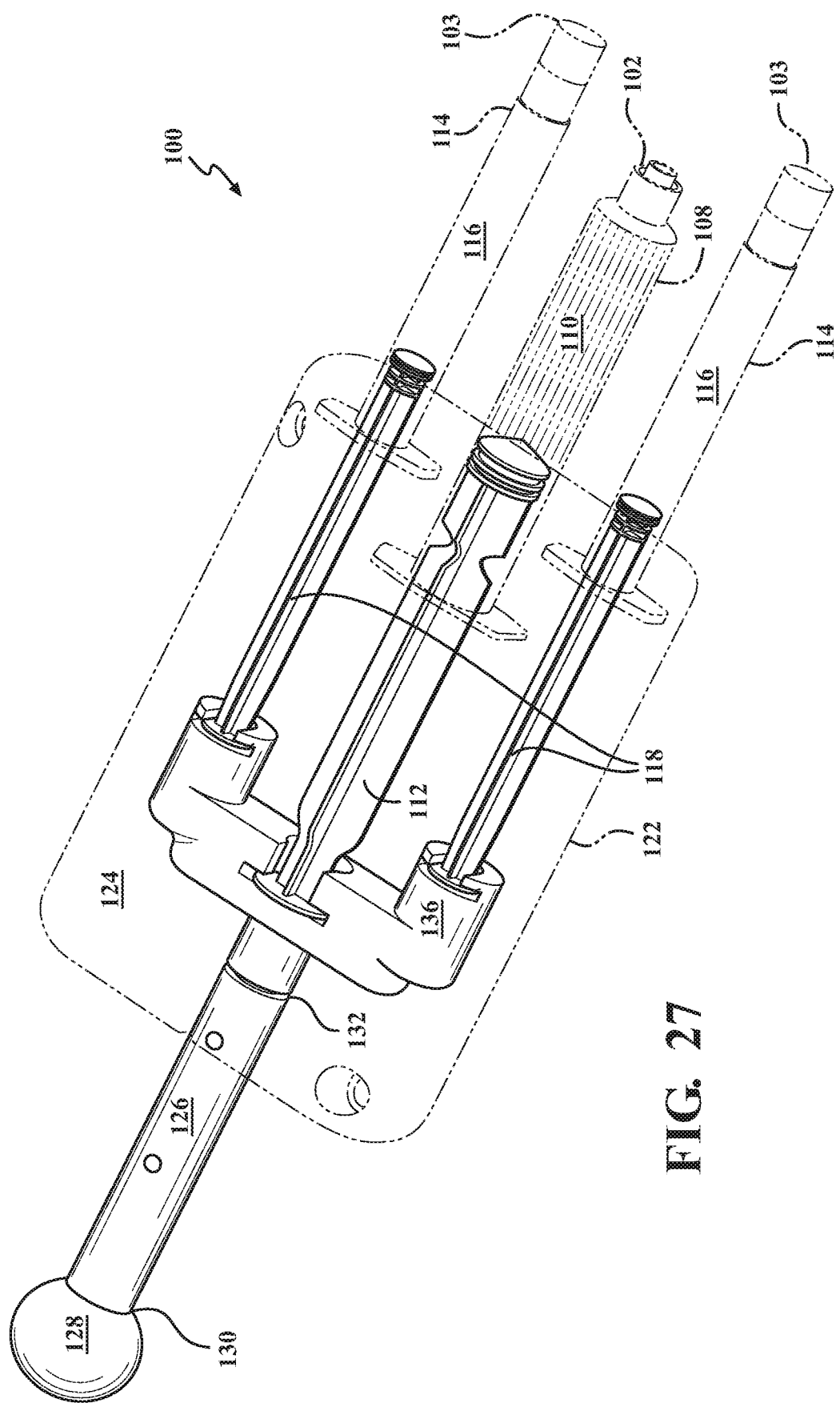
FIG. 27 is a perspective view of the micro infusion module of FIG. 22 which illustrates the micro infusion module in a loaded position wherein the fluid reservoir has accumulated fluid and the vacuum chambers have accumulated a vacuum.
Figure 28:
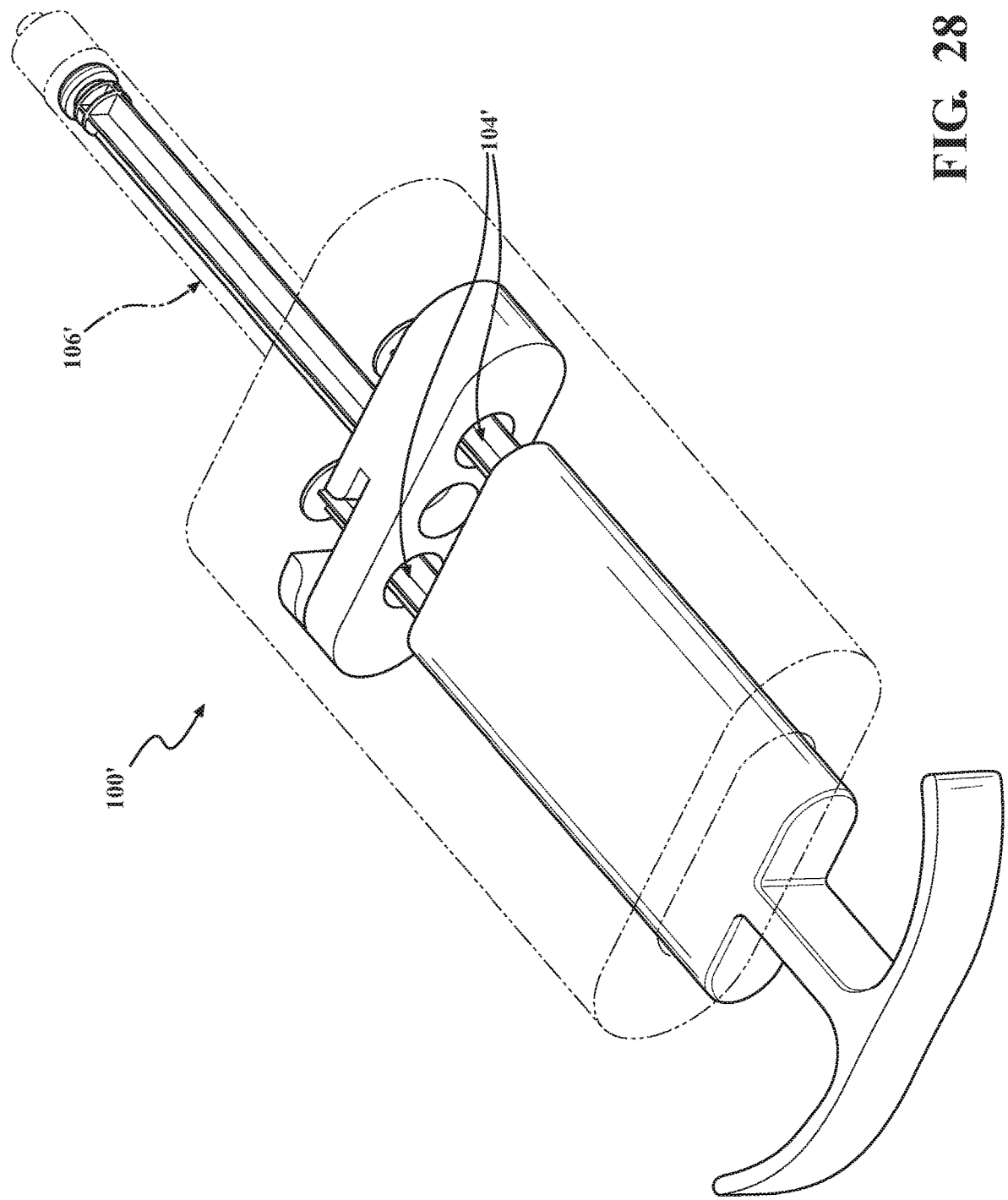
FIG. 28 is a perspective view of another example of a micro infusion module with a shell made transparent.

FIG. 27 illustrates the handle 128, the actuation shaft 126, the actuation linkage 136, the fluid piston(s) 112, and the vacuum piston(s) 118 relative to the shell in a loaded position. In the loaded position, the fluid reservoir 110 includes a volume of conductive fluid and the vacuum chambers 116 have accumulated a vacuum.

Once force is applied to the handle 128 of the micro infusion module 100 in a proximal direction, the vacuum pistons 118, which are moveably disposed in the vacuum body 114, move to create a vacuum in the vacuum chamber 116, and the fluid piston 112, which is moveably disposed in the fluid body 108, moves to load fluid into the fluid reservoir 110 (via vacuum like a syringe). In certain examples, the vacuum accumulator 105 comprises a syringe and a cap 103, while the fluid delivery actuator 106 comprises a syringe with a fluid coupling 102. In such examples, a proximal end (piston) of the vacuum accumulator(s) 105 and a proximal end (piston) of the fluid delivery actuator 106 is connected to the actuation linkage 136.

Once the micro infusion module 100 is loaded a latch (not shown) located on the handle 128, the actuation linkage 136, or the shell can be used to prevent the vacuum accumulators 105 from actuation the fluid delivery actuator 106 and discharging the fluid loaded in the fluid reservoir 110 in the interim between loading and connecting the micro infusion module 100 to the irrigated electrode assembly 12, 512. Alternatively, a cap (not shown) can be applied to the fluid coupling 102 to prevent fluid discharge in the interim between loading and connecting the micro infusion module 100 to the irrigated electrode assembly 12, 512.

Figure 30:
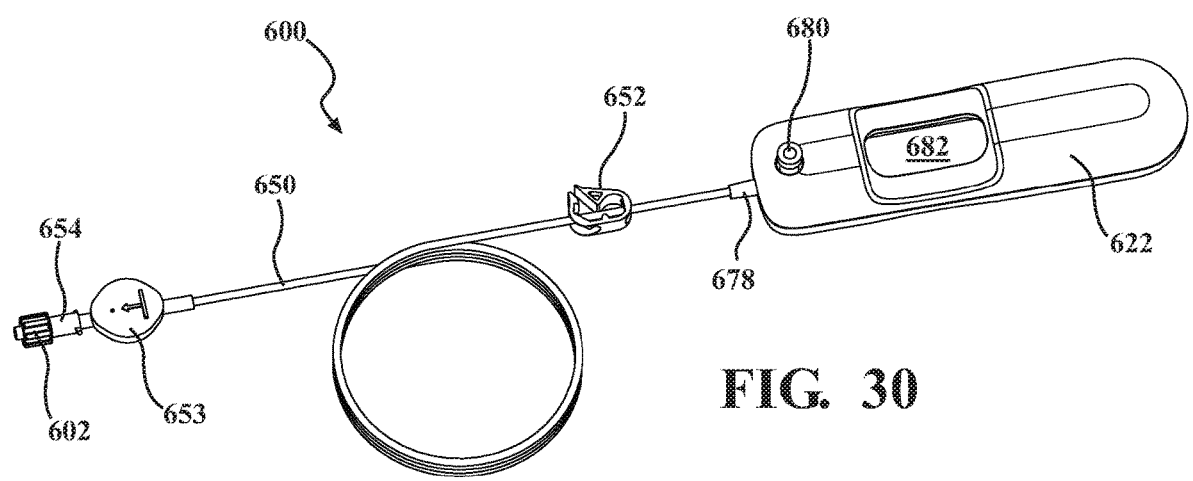
FIG. 30 is a perspective view of an exemplary micro infusion module.
Figure 31:
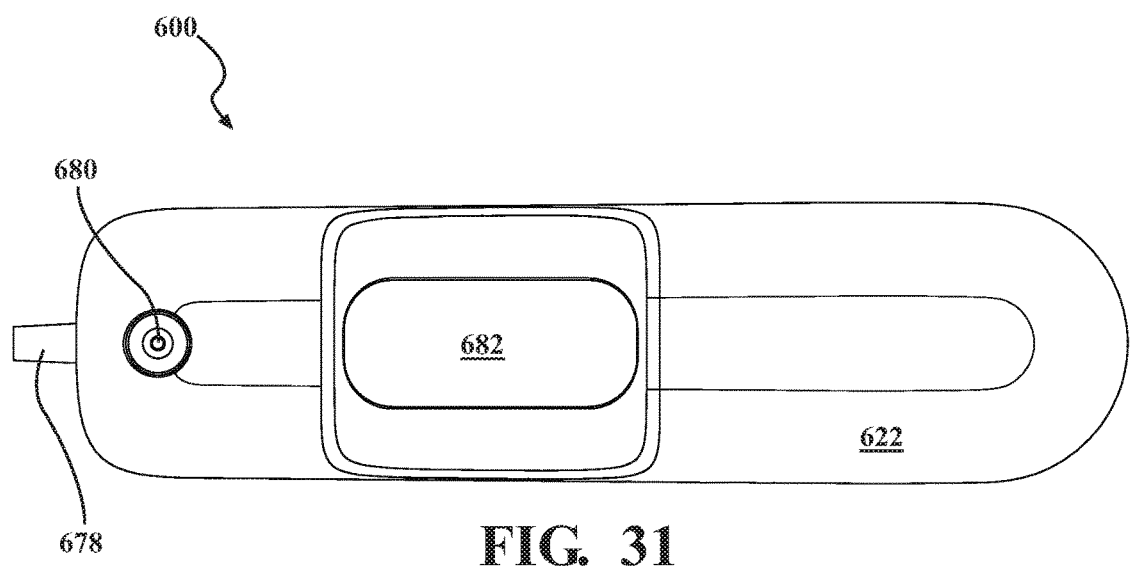
FIG. 31 is a top view of the body of the micro infusion module of FIG. 30.

Referring now to FIGS. 30-35, another example of the micro infusion module 600, shaped or configured to be releasably coupled to the irrigated electrode assembly, is illustrated. Like the example micro infusion module 100 of FIGS. 24-27, the example micro infusion module 600 of FIGS. 30-35 is sized to be held by a single hand. Referring now to FIG. 30, the micro infusion module 600 can be releasably coupled to the irrigated electrode assembly 12, 512, with a fluid coupling 602, such as a luer lock fitting. The micro infusion module 600 is configured to be placed in fluid communication with any of the exemplary irrigated electrode assemblies 12, 512 described herein.

Although the micro infusion module 600 illustrated in FIG. 30 includes a one of the fluid coupling 602, it should be appreciated that the fluid coupling 602 can feed into a split line to supply multiple irrigation channels. Alternatively, two or more of the micro infusion module 600 can be used to supply irrigated electrode assemblies having multiple irrigation channels such as the irrigated electrode assembly 12, 512 described herein.

Referring now to FIG. 30, the micro infusion module 600 includes a flexible infusion line 650, a stop clamp 652, a filter and vent assembly 653, a flow restrictor 654, and the fluid coupling 602. The micro infusion module may also include a vent assembly to make sure that that the supply of fluid to the irrigated electrode assembly 12, 512 is free of gas. The vent can be located on the flexible infusion line 650. Once the micro infusion module 600 is filled with fluid, the stop clamp 652 is can be used to start and stop the output of fluid from the micro infusion module 600.

Flow rate of fluid output of the micro infusion module 600 is set with the flow restrictor 654. The flow restrictor 654 can be configured to constrict fluid flow to a rates between about 0.5 to about 15 mL/hour. It should be appreciated that flow rate of fluid output of the micro infusion module 600 can be modified by using specific examples of the flow restrictor 654 to produce a desired flow rate. Various flow restrictors or flow limiters known to those of skill in the art can be used and for purposes of the present disclosure can be described as any component that is shaped to restrict the flow of fluid to a set flow rate. Some non-limiting examples of such flow restrictors are capillary (e.g. tubing with a predetermined restriction in cross-section to control the flow rate therethrough), while other such flow restrictors use single stage or multi-stage orifice plates to handle high and low flow rates. In many examples, the flow restrictor 654 restricts fluid output to a rate of from about 0.5 to about 15 mL/hour, or about 1 to about 12, mL/hour.

Figure 34:
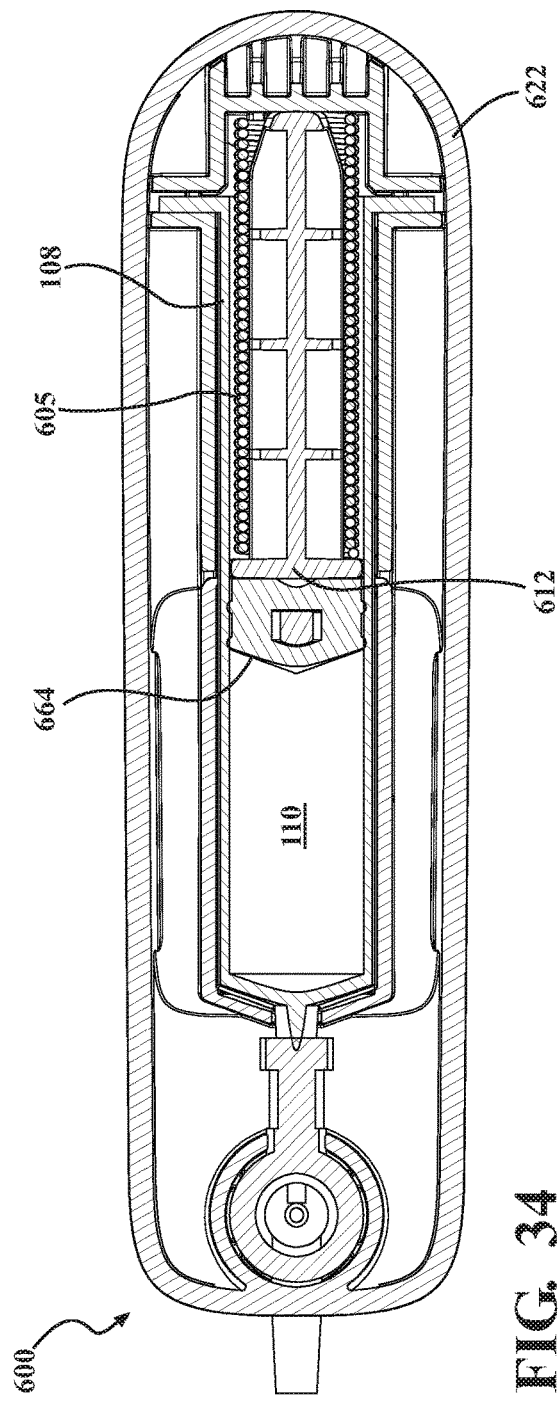
FIG. 34 is an exploded view of the micro infusion module of FIG. 30.
Figure 35:
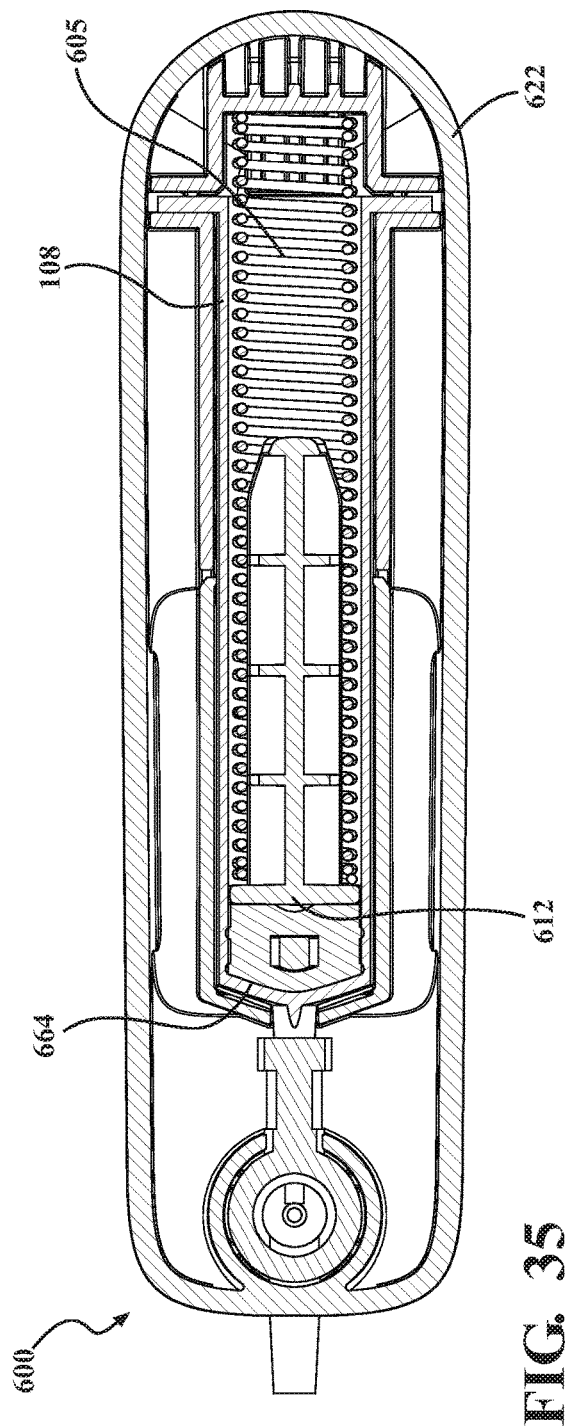
FIG. 35 is a perspective, exploded view of the micro infusion module of FIG. 30.

Referring now to FIGS. 34 and 35, the micro infusion module 600 also includes a shell 622 having an exterior surface 638 and an interior surface 640. The shell 622 includes a first part 642 and a second part 644 that are configured to be coupled or releasably coupled to one another. The interior surface 640 of the shell 622 defines a void 624. In many examples the shell 622 comprises the first and second parts 642, 644 formed from molded polymer and having interior features (which can be considered part of the inner surface 640 of the shell 622) to create a void to "hold" or "secure" the specifically shaped components housed within the shell 622.

Still referring now to FIGS. 34 and 35, the void 624 is shaped to house the at least one potential energy accumulator 604 comprising a biasing element 605 (e.g. a spring), a fluid delivery actuator 606, and a port assembly 674. The potential energy accumulator 604 is configured to store and release potential energy and the fluid delivery actuator 606 is configured to cooperate with the potential energy accumulator 604 to discharge fluid from the micro infusion module 600. The potential energy accumulator 604 and the fluid delivery actuator 606 are configured to simultaneously fill a fluid reservoir 610 within the fluid delivery actuator 606 and store potential energy in the potential energy accumulator 104 via application of force when uncoupled from the irrigated electrode assembly 12, 512, and also configured to simultaneously discharge fluid from the fluid reservoir 610 via the release of kinetic energy. In other words, the potential energy accumulator 604 powers the fluid delivery actuator 606.

Figure 32:
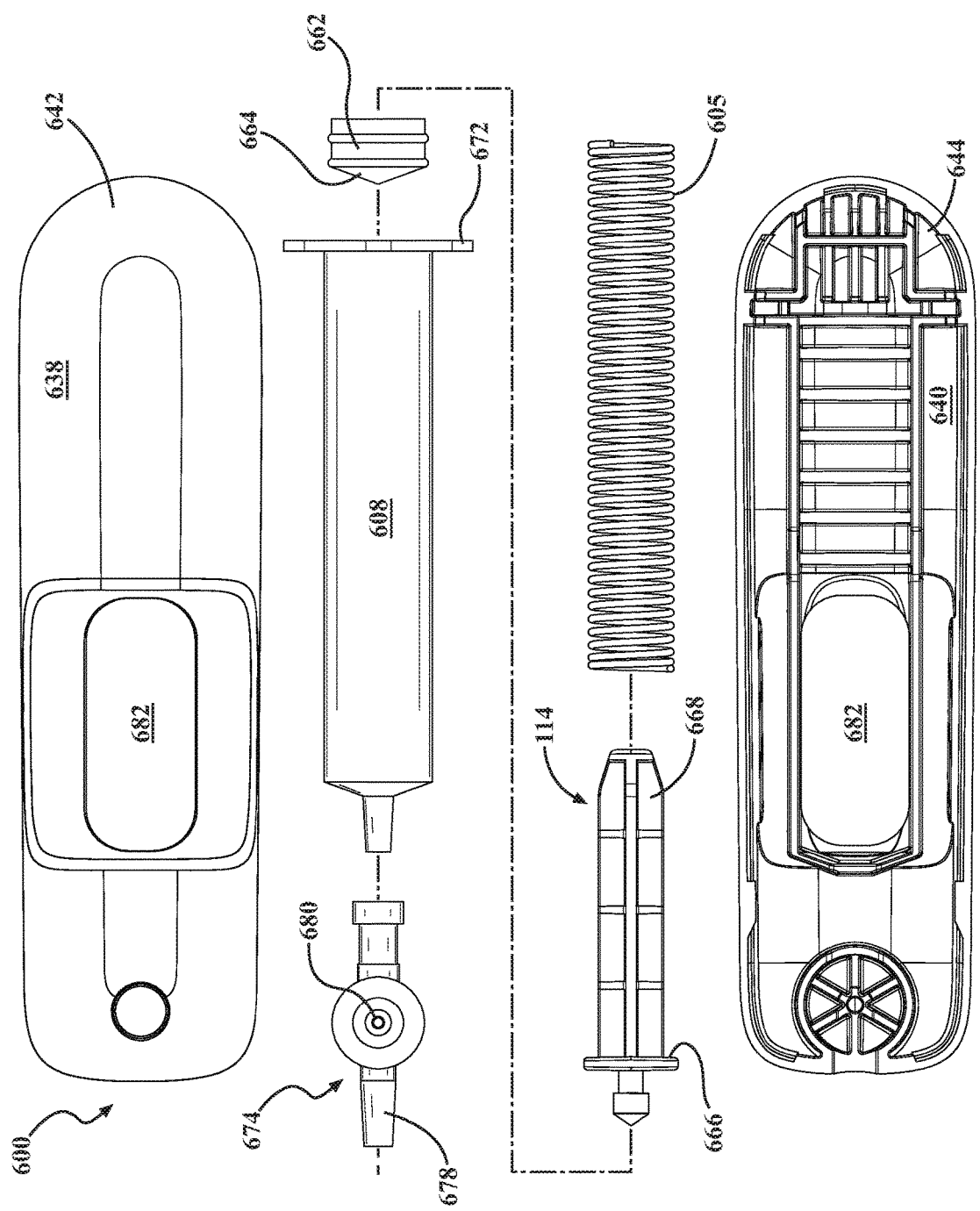
FIG. 32 is an isolated view of the fluid piston of the micro infusion module of FIG. 30 in a first position in which a potential energy accumulator has accumulated and stored potential energy and the volume of the fluid reservoir is maximized.
Figure 33:
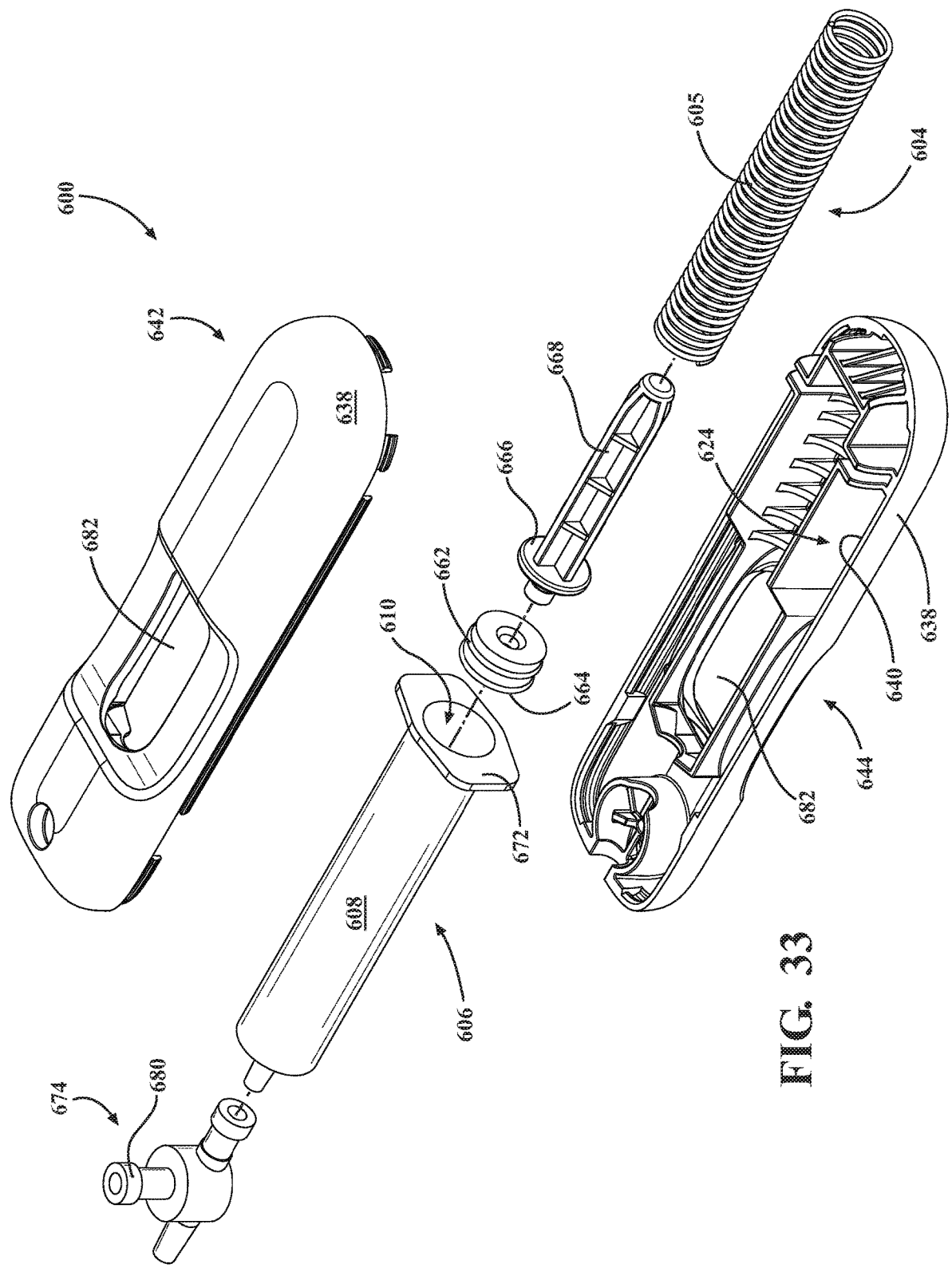
FIG. 33 is an isolated view of the fluid piston of the micro infusion module of FIG. 30 in a second position in which the potential energy accumulator has released its potential energy and the volume of the fluid reservoir is minimized.

Referring now to FIGS. 32 and 33, the fluid delivery actuator 606 comprises a fluid body 608 defining the fluid reservoir 610 and a fluid piston 612 moveably disposed in the fluid reservoir 610. In many examples, the fluid body 608 comprises a clear or transparent polymer so that the fluid reservoir 610 (including its contents and size) as well as the fluid piston 612 are visible within the fluid body 608. In some examples, the fluid body 608 defines the fluid reservoir 610 having a 10 mL capacity. The fluid body can have a luer slip tip a distal end thereof proximal said fluid reservoir 610. The fluid piston 612 comprises a head 662 having a front face 664 which partially defines the fluid reservoir 610 and a back surface 666 facing opposite the front face 664 and having a shaft 668 extending therefrom. The biasing element 605, a spring that is helical in shape, is carried by the shaft 668 and compressible against the inner surface of the shell 622. The proximal end of the fluid body 608 has a collar 672 located thereon that cooperates with the shell to fit in the and shaped be secured in the void 624 defined by the shell 622. The back surface 666, the fluid body 608, and the collar 672 at least partially define a back cavity in which the shaft 668 having the biasing element 605 carried thereabout is at least partially contained.

The fluid piston 612 is moveably disposed in the fluid reservoir 610 between a first position in which the biasing element 605 has accumulated and stored potential energy and is in the compressed state and a volumetric fluid capacity of the fluid reservoir 610 is maximized, and a second position in which the biasing element 605 has released its potential energy and is in an uncompressed state and the volumetric fluid capacity of the fluid reservoir 610 is minimized. In FIG. 33, the fluid piston 612 is in the first position and in FIG. 32, the fluid piston 612 is in the second position. As the fluid piston 612 moves from the first position to the second position, fluid contained within the fluid reservoir 610 is discharged and a volume of the back cavity increases. Fluid discharge occurs as the fluid piston 612 moves from the first to the second position. Of course, the discharge can be stopped by clamping the flexible infusion line 650 with the stop clamp 652 and started by unclamping the flexible infusion line 650. When the micro infusion module 600 is loaded (i.e., filled with fluid and potential energy), and the flexible infusion line 650 is unclamped, fluid is discharged at a set by the flow restrictor 654.

The port assembly 674 is partially housed within the shell 622 and located at a distal end of the fluid reservoir 610. The port assembly 674 includes a port coupling 678 and a fill port 680. As is best illustrated in FIG. 30, the port coupling 678 extends past the exterior surface 638 of the shell 622 and is connected or releasably connected to the flexible infusion line 650. As is also illustrated in FIG. 30, the fill port 680 also extends past the exterior surface 638 of the shell 622. The port assembly 674 is particularly advantageous because it allows for the loading of the micro infusion module 600 while the micro infusion module 600 is coupled to the irrigated electrode assembly 12, 512. Further, the micro infusion module 600 can be reloaded during use if fluid is running low. Nonetheless, the port assembly 674 also allows the loading of the micro infusion module 600 when it is not coupled to the irrigated electrode assembly 12, 512.

The micro infusion module 600 is configured to be releasably connected to a fill source, e.g. a syringe filled (filled with fluid such as saline). Some non-limiting examples of suitable fill source are 5, 6, 7, 8, 9, or 10 mL syringes having a luer lock tip. The fill source can be filled with a fluid previously drawn from the fluid supply, e.g. an I.V. fluid bag, a sterilized fluid vial, etc. The micro infusion module 600 of this example can have a total volumetric fluid capacity from about 1 to about 20, from about 2 to about 10, or from about 2 to about 8, mL in a maximized state. In some examples, fluid reservoir 610 has a 10 mL capacity. In this example, the port assembly 674 includes the fill port 680 (e.g. a luer lock coupling, a slip tip coupling, an eccentric tip coupling, a catheter tip coupling, etc.) which releasably connects to a corresponding connector on the fill source and also a port coupling 678 that connects or in some examples releasably connects to the flexible infusion line 650.

The micro infusion module 600 is in many examples, assembled and provided with a minimal amount of compression on the biasing element 605 and minimal to no volumetric fluid capacity. To load the micro infusion module 600, the fill source is connected to the fill port 680 via luer lock or a similar connection mechanism and fluid is injected into the micro infusion module 600. During injection, the fluid reservoir 610 is filled with fluid and the biasing element compresses further as the volumetric fluid capacity of the fluid reservoir 610 increases to accommodate fluid injected. Of course, as the volumetric fluid capacity of the fluid reservoir 610 increases, the volume of the back cavity decreases. Further, as the volumetric fluid capacity of the fluid reservoir 610 increases, biasing element 605 is further compressed. Stated simply, loading the micro infusion module 600 simultaneously fills the fluid reservoir 610 and stores potential energy in the potential energy accumulator 604.

Once the micro infusion module 600 is loaded and connected to the fluid intake port 32 on the irrigated electrode assembly 512, the fluid delivery actuator 606 is in fluidic communication with the irrigation channel 534 and the fluid irrigation port 544, and the potential energy accumulator 604 and the fluid delivery actuator 606 are configured to release the potential energy and actuate the fluid piston 612 to discharge fluid from the fluid reservoir 610 into the irrigation channel 534 and through the fluid irrigation port 544.

Referring back to FIG. 31, the micro infusion module 600 also includes a window portion 682 positioned on the exterior surface 638 of the shell 622. The window portion 682 allows light to pass therethrough. Typically, the window portion 682 is an opening in the shell 622 or comprises a polymer that is transparent to offer a user visibility of the fluid reservoir 610 (and fluid/amount of fluid therein). However, various examples of the micro infusion module 600 may utilize the window portion 682, which is translucent, e.g. offers limited visibility. The fluid reservoir 610 and the fluid piston 612 moveably disposed in the fluid reservoir 610 are at least partially visible through the window portion 682. As such, the window portion 682 is typically located closer to a distal end of the shell 622.

In examples where the fluid body 608 comprises a clear or transparent polymer, the window portion 682 allows a user to determine how much fluid is in the fluid reservoir 610. The window portion 682 can be formed from a distinct part or window, all or a portion of the shell 622 can comprise a transparent material, all or a portion of the entire shell 622 can comprise a transparent material and other portions can be selectively coated or frosted to create the window portion 682, etc. In the embodiment shown in FIGS. 30-35, the window portion 682 is simply an opening in the shell 622. Accordingly, the shell 622 can be constructed in various configurations to achieve the window portion 682.

In some examples, shell 622 includes an activation button on the exterior surface 638 to initiate fluidic output, and corresponding activation elements configured to hold and release the at least one potential energy accumulator 604 in a loaded position within the micro infusion module 600.

From an infusion rate or fluid discharge perspective, the rate of discharge of the micro infusion module 100, 600 can be controlled by the design of the micro infusion module 100, e.g. vacuum capacity, fluid capacity and the various sizes of the components (e.g. the potential energy accumulator 104, 604 the fluid delivery actuator 106, 606 etc.). Alternatively, the micro infusion module 100, 600 can be designed to discharge fluid at a rate which exceeds the rate of irrigation needed for a particular procedure, and the rate can be throttled or controlled with the flow restrictor 33, 654.

The micro infusion module 100, 600 is referred to as "micro" because it is: (1) micro sized (handheld); and (2) infuses micro amounts (e.g. mL of fluid) at relatively low infusion rates. Specifically, regarding capacity, some examples of the micro infusion module 100, 600 include one or more of the fluid delivery actuator 106, 606 having a total volumetric capacity of less than about 15, less than about 10, from about 1 to about 15, or from about 2 to about 8, mL. In examples where the micro infusion module 100, 600 includes a single fluid delivery actuator 106, 606 this would mean that the volumetric capacity of the fluid reservoir 110, 610 of the fluid delivery actuator 106, 606 is less than about 15, less than about 10, from about 1 to about 15, or from about 2 to about 8, mL. Specifically, regarding rate, some examples of the micro infusion module 100, 600 are configured to discharge fluid at a rate of from about 0.5 to about 15, or from about 1 to about 12, mL/hour. In various non-limiting embodiments, all values and ranges of values including and between those described above are hereby expressly contemplated for use herein.

The micro infusion module 100, 600 can be designed and/or supplied for different procedures and/or surgical situations with different volumetric capacities ranging from about 0.5 to about 20 mL, e.g. an 8 mL version, a 13 mL version, so on and so forth. Further, the micro infusion module 100 can be supplied for different procedures with different discharge rates for different procedures and/or surgical situations, e.g. a 6 mL/hr. version, a 9 mL/hr. version, so on and so forth. Further, in many examples, the micro infusion module 100, 600 can be designed to withstand various sterilization procedures and/or supplied sterilized (e.g. subsequent sterilization and packaged in sterile packaging. Furthermore, the micro infusion module 100, 600 can be designed and/or supplied use with the irrigated electrode assembly 12, 512 as "reusable" (e.g. autoclavable) or "disposable" (e.g. supplied sterilized in a package and is used and discarded after a single use).

In addition, many examples of the micro infusion module 100, 600 are designed to be loaded by hand. That is, the micro infusion module 100, 600 can be loaded and operated without a power source (wired source or battery source) and thus is not connected to a power source. In some examples, the micro infusion module 100 is powered via vacuum, e.g. with the vacuum accumulator 105 and is free of a spring. In other examples, the micro infusion module 600 is powered by a spring, e.g. spring loaded. In other words, in various examples, the micro infusion module 100, 600 is free of a spring, a battery, and an electrical power source or a connection thereto.

A method of ablating biological tissue with an ablation system 10, 510 including the irrigated electrode assembly and the micro infusion module sized to be held by a single hand is also disclosed. Any combination of the exemplary irrigated ablation assemblies and the exemplary micro infusion modules described above can be utilized in the ablation system 10, 510 disclosed herein. That is, the ablation system 10 the components thereof (e.g., the irrigated electrode assembly 12, 512 and the micro infusion module 100) are just as described above.

Figure 36:
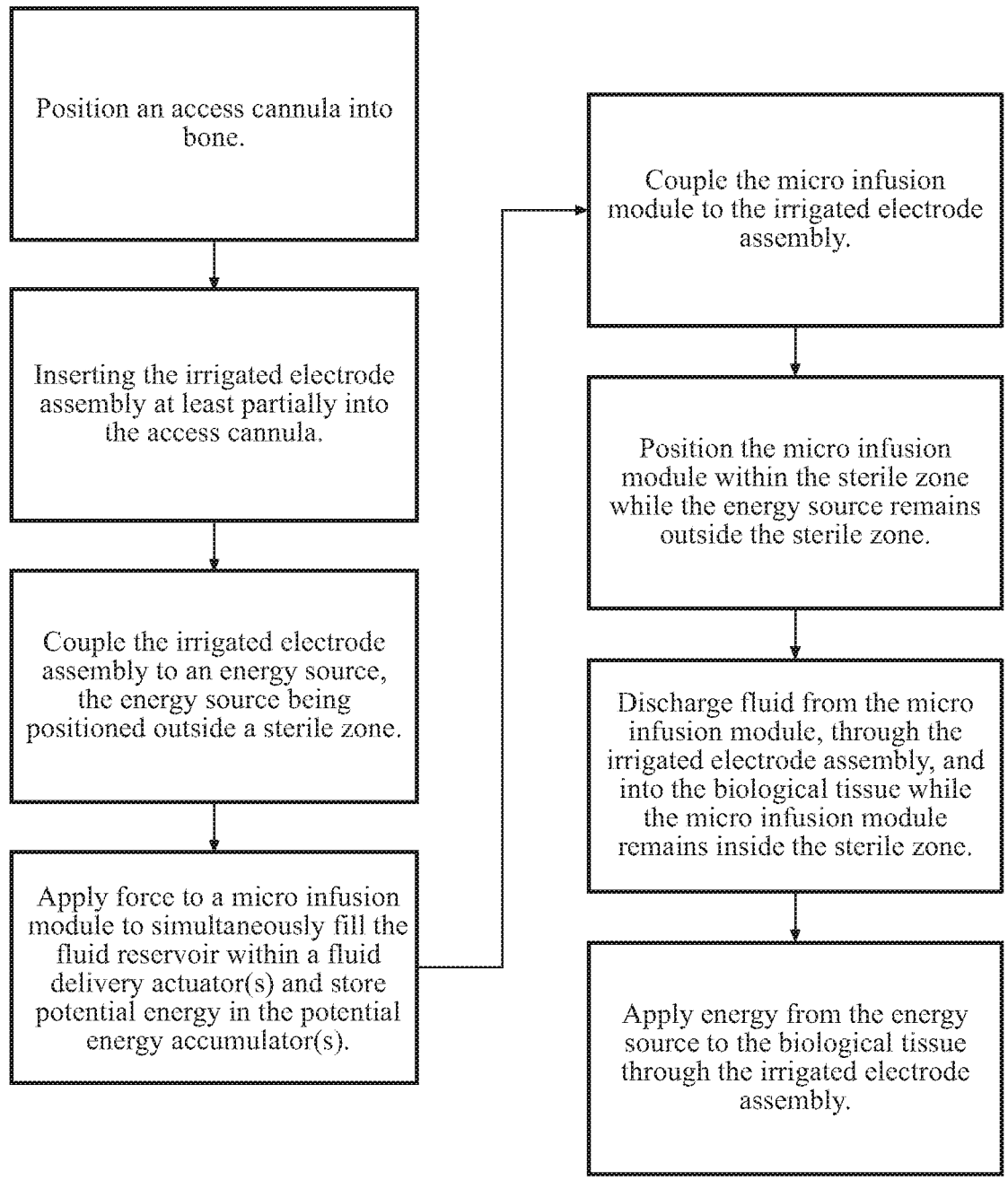
FIG. 36 is a flow diagram illustrating one example of a method of ablating biological tissue with the ablation system comprising the irrigated electrode assembly and micro infusion module.

The method includes the steps of: positioning an access cannula 56 into bone; inserting the irrigated electrode assembly 12, 512 at least partially into the access cannula 56; coupling the irrigated electrode assembly 12, 512 to an energy source 54, the energy source being positioned outside a sterile zone (SZ); filling the fluid reservoir 110, 610 of the micro infusion module 100, 600 with fluid; applying force to the micro infusion module 100, 600 to store potential energy therein; coupling the micro infusion module 100, 600 to the irrigated electrode assembly 12, 512; positioning the micro infusion module 100, 600 within the sterile zone (SZ) while the energy source 54 remains outside the sterile zone (SZ); discharging fluid from the micro infusion module 100, 600 through the irrigated electrode assembly 12, 512 and into the biological tissue while the micro infusion module 100, 600 remains inside the sterile zone (SZ); and applying energy from the energy source 54 to the biological tissue through the irrigated electrode assembly 12, 512. FIG. 36 is a flow diagram illustrating an example of the preceding method of ablating biological tissue with the irrigated electrode assembly 12, 512 and the micro infusion module 100, 600.

The method may also include the step of providing the components which can be included in the ablation system, e.g. the access cannula 56, the irrigated electrode assembly 12, 512, the micro infusion module 100, 600, the fluid supply, etc. In some examples, the components are provided in a kit. In other examples, the components are provided separately.

In some examples, the various components are provided sterilized and/or sterilized packaging. In one example, the irrigated electrode assembly 12, 512 is supplied sterilized in packaging. In another example, the micro infusion module 100, 600 is supplied sterilized in packaging. In yet another example, the fluid supply is supplied sterilized in packaging. In many embodiments of this ablation system and method, the fluid comprises saline.

The various methods contemplated herein may include the step of positioning an access cannula 56 into bone, e.g. a vertebral body. In many examples, the access cannula 56 comprises metal. However, it should be appreciated that a vertebral body is just one example of bone into which the access cannula 56 can be positioned and that the ablation system 10, 510 is not limited to use in vertebral bodies/spinal procedures.

Some examples of the method further comprise the step of generating an image with an electromagnetic imaging technique to determine the location of the distal end of the irrigated ablation assembly. The image or images taken can be used to confirm that the distal end of the irrigated electrode assembly is adjacent a tumor, that the distal end of the irrigated electrode assembly is adjacent a facet nerve proximate a vertebral body, or even that the proximal transfer surface and a distal transfer surface of the irrigated electrode assembly are positioned on opposite sides of a basivertebral nerve. In addition, image or images taken can be used to confirm that the proximal end of the proximal transfer surface extends past a distal end of the access cannula 56 an into a desired position within the vertebral body. The micro infusion module disclosed herein is visible, without a radio opaque marker, once the proximal end of the proximal transfer surface extends past the distal end of the access cannula 56.

The access cannula 56 comprises a cannula shaft 58. The cannula shaft 58 includes a proximal end (not shown), and a distal end 59. The cannula shaft 58 may be straight and define a lumen (not identified) extending between the proximal and the distal end 60 such that the cannula shaft 58 is tubular in shape. The cannula shaft 58 is formed with sufficient mechanical properties to maintain integrity as the cannula shaft 58 is driven through the pedicle of the vertebra. The ablation system 10, 510 may include a trocar (not shown) removably positioned within the cannula shaft 58 during the step of positioning an access cannula 56 into bone, e.g. placement of the distal end 59 of the cannula shaft 58 into the vertebral body. The trocar may include a length slightly greater than a length of the cannula shaft 58 such that a sharp tip of the trocar pierces the cortical bone of the cortical rim, and the trocar prevents coring of tissue within the lumen of the cannula shaft 58. Once the distal end 59 of the cannula shaft 58 is positioned within the vertebral body, the trocar is removed. The access cannula 56 provides a working channel to within the interior region of the vertebral body along a longitudinal axis defined by the cannula shaft 58.

The distal portion 18, 518 of the irrigated electrode assembly 12, 512 may be flexible. To this end, the method disclosed herein may also include the step of using a device that creates a lumen and facilitates positioning of the distal portion 18, 518 of the irrigated electrode assembly 12, 512 within the vertebral body that is offset from a longitudinal axis of the access cannula 56.

Figure 37:
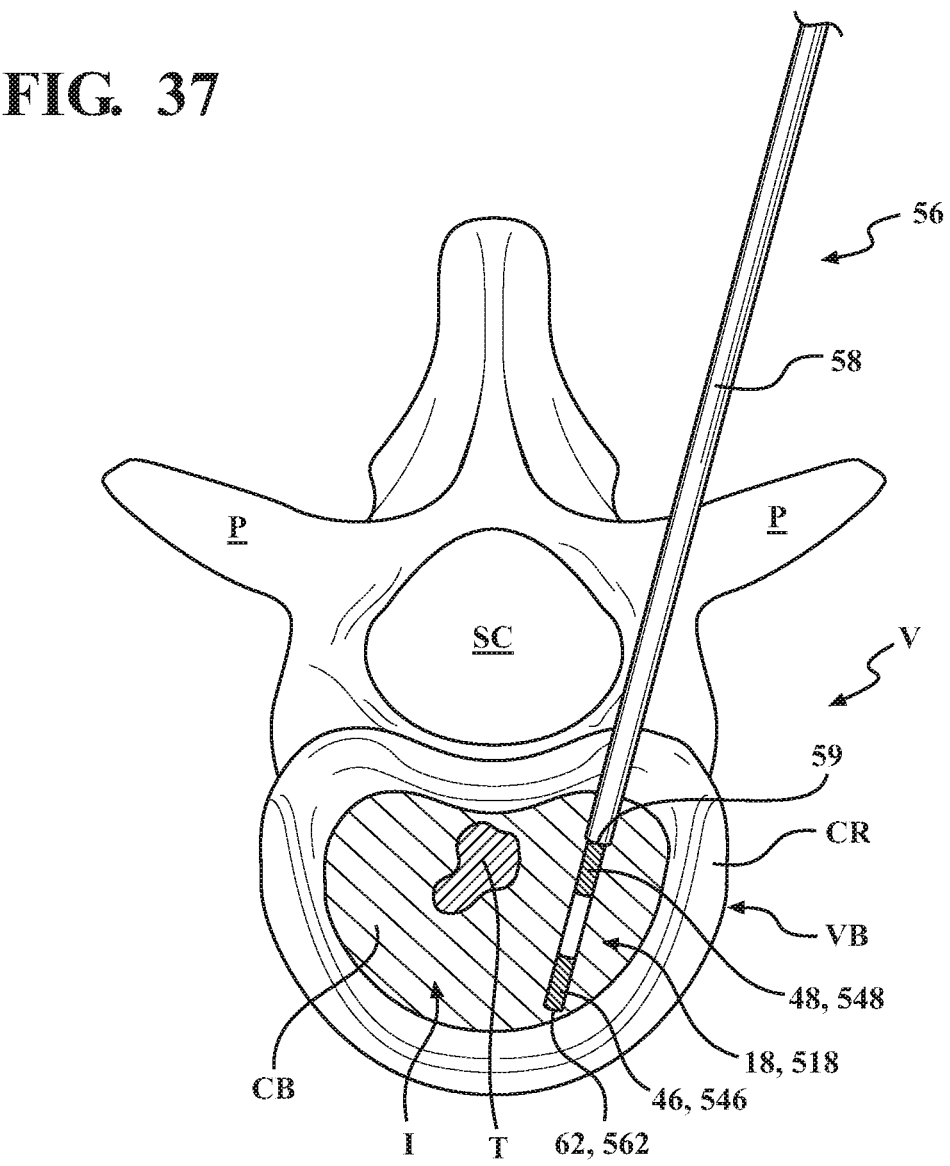
FIG. 37 is a perspective view of an axial section of a vertebra (V) with an access cannula and the irrigated electrode assembly positioned therein.

Referring now to FIG. 37, an illustration of an axial section of a vertebra (V) is shown with the access cannula 56 and the irrigated electrode assembly 12, 512 positioned therein. The vertebra (V) includes pedicles (P) on opposing lateral sides of a spinal canal (SC) that provide a generally linear path from a posterior approach to an interior (I) region of the vertebral body (VB). The vertebral body (VB) includes a cortical rim (CR) formed from cortical bone that at least partially defines the interior (I) region. A volume of cancellous bone (CB) and a tumor (T) is within the interior (I) region.

Prior to the ablation procedure, the fluid reservoir 110, 610 of the micro infusion module 100, 600 can be filled with fluid and potential energy can also be stored therein. The steps of filling the fluid reservoir 110, 610 of the micro infusion module 100, 600 with fluid and applying force to the micro infusion module 100, 600 to store potential energy therein can be conducted simultaneously.

In one specific example, the micro infusion module 100, can be held in one hand and while force is applied in a proximal direction to the handle 128 on the micro infusion module 100 with the other hand to simultaneously fill the fluid reservoir 110 within one or more fluid delivery actuators 106 and store potential energy in one or more vacuum accumulators 105.

In another specific example, the micro infusion module 100 can be held in one hand while force is applied to the handle 128 on the micro infusion module 100 with the other hand to simultaneously fill the fluid reservoir 110 in one fluid delivery actuator 106 and store potential energy in two vacuum accumulators 105. These steps are described above and can be singularly referred to as "loading" the micro infusion module 100.

In a another more specific example, the micro infusion module 600 can be held in one hand while a fill source is attached and force is applied with the other hand to inject liquid into the fluid reservoir 610 of the micro infusion module 600 to simultaneously fill the fluid reservoir 610 in the fluid delivery actuator 606 and store potential energy in the biasing element 605. These steps are described above and can be singularly referred to as "loading" the micro infusion module 600.

The steps of filling the fluid reservoir 610 of the micro infusion module 600 with fluid and applying force to the micro infusion module 600 to store potential energy therein can conducted when the micro infusion module 600 is uncoupled from the irrigated electrode assembly 12, 512 assembly or can be conducted when the micro infusion module 600 is coupled to the irrigated electrode assembly 12, 512. Advantageously, the micro infusion module 600 is coupled to the irrigated electrode assembly 12, 512. This allows for the steps of filling the fluid reservoir 610 of the micro infusion module 600 with fluid (typically with the fill source) and applying force to the micro infusion module 600 to store potential energy therein (the step of loading the micro infusion module 600) to be repeated one or more times during surgery. Of course, in either scenario, the steps of filling the reservoir 610 of the micro infusion module 600 with fluid and applying force to the micro infusion module 600 to store potential energy therein can be conducted simultaneously.

Figure 38:
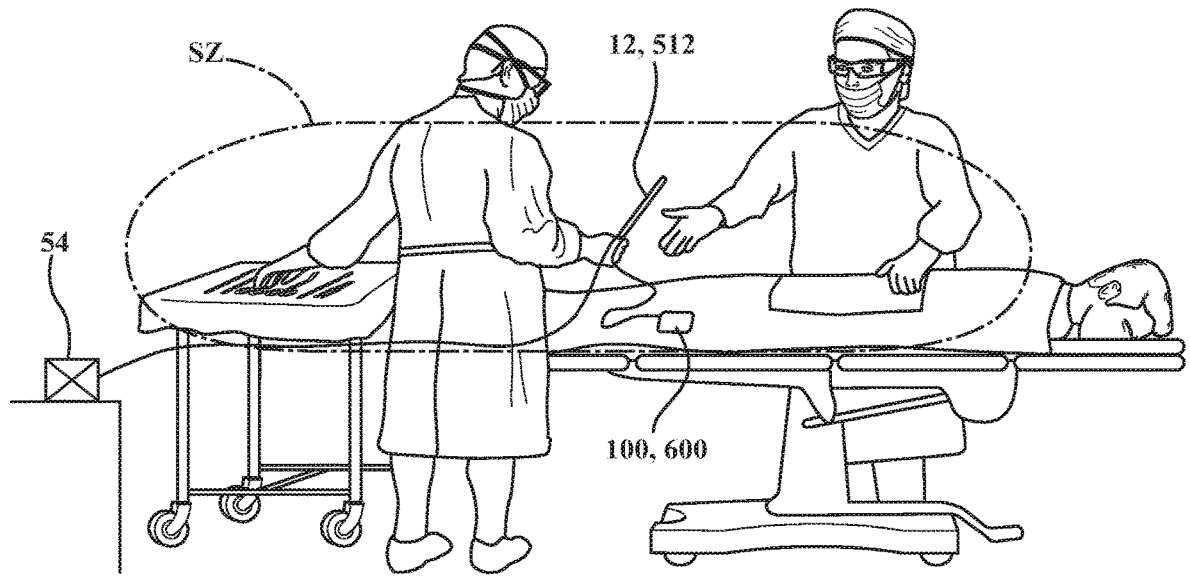
FIG. 38 is a side view of a sterile zone in an operating room.
Figure 39:
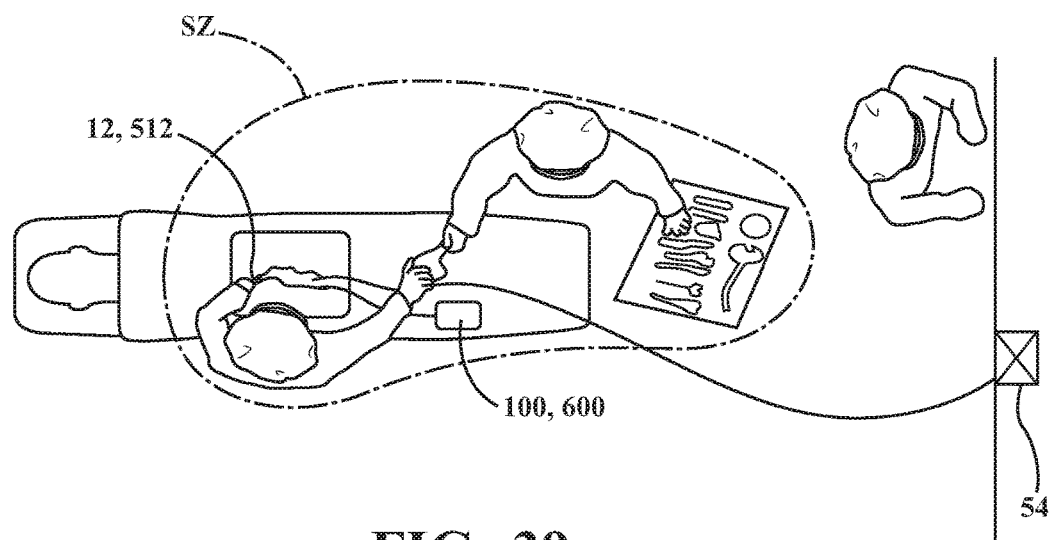
FIG. 39 is a top view of a sterile zone in an operating room.

The size of the micro infusion module makes it convenient and easy to use in the operating room. Further, many exemplary examples of the micro-infusion module are sterile. FIGS. 38 and 39 show an operating room including a sterile zone. The sterile zone (SZ), an example of which indicated via the hashing in FIGS. 38 and 39, is a specific area that is considered sterile and free of microorganisms. Maintaining a sterile zone (SZ) is not an easy task because there are many chances for a breach in sterility during set-up, operation, and post-operation. In this method, the micro infusion module 100, 600 can be: loaded, coupled to the irrigated electrode assembly 12, 512; and/or positioned within the sterile zone (SZ). In fact, in some methods, the micro infusion module 100, 600 can be conveniently positioned in the sterile zone (SZ) on the patient or patient support apparatus before or during the step of discharging.

Once the access cannula 56 is positioned into bone, the irrigated electrode assembly 12, 512 is at least partially inserted into the access cannula 56, the irrigated electrode assembly 12, 512 is coupled to an energy source 54 outside the sterile zone (SZ), the micro infusion module 100 is loaded and coupled to the irrigated electrode assembly 12, 512, the micro infusion module 100, 600 is positioned within the sterile zone (SZ) while the energy source 54 remains outside the sterile zone (SZ) and ablation of biological tissue, e.g. tumors, nerves, can begin.

In one non-limiting example, the method is directed to ablation of biological tissue comprising nerve(s) and/or tumorous tissue (e.g. a tumor (T)). As one example, the distal portion 18 of the irrigated electrode assembly 12, 512 can be positioned within a vertebral body adjacent a tumor. As another example, the distal end 20 of the irrigated electrode assembly 12, 512 can be positioned adjacent a facet nerve proximate a vertebral body (V). In yet another example, the method would include the step of positioning the irrigated electrode assembly 12, 512 within vertebral body (V) such that the proximal transfer surface 40 and a distal transfer surface 38 are positioned on opposite sides of a basivertebral nerve.

The step of discharging fluid from the micro infusion module 100, can occur before, during, and/or after the step of applying energy from the energy source 54 to the biological tissue through the irrigated electrode assembly 12, 512. In some examples, at least 2 but no more than about 6, about 7, about 8, about 9, about 10, about 11, about 12, about 13, about 14, or about 15, mL of fluid is discharged into the biological tissue. The step of discharging can be further described as discharging fluid into biological tissue at a rate of from about 0.5 to about 15, or about 1 to about 12, mL/hour. In various non-limiting embodiments, all values and ranges of values including and between those described above are hereby expressly contemplated for use herein.

In one example, the step of discharging is further defined as discharging a rate of from about 6 to about 12 mL/hour for a period of from about 2 to about 25 minutes. In another example, the step of discharging is further defined as discharging a rate of 9 mL/hour for a period of from about 5 to about 25 minutes. In various non-limiting embodiments, all values and ranges of values including and between those described above are hereby expressly contemplated for use herein.

Ablation (e.g. RF ablation) creates an electrical circuit through the biological tissue, typically using an oscillating electrical current to produce resistive heating within the tissues surrounding the irrigated electrode assembly 12, 512. Because biological tissue is a poor conductor of electricity, current flowing through tissues leads to ionic agitation and production of frictional heat. The step of discharging (or the micro infusion) of fluid, e.g. saline, helps control the temperature of the biological tissue to ensure effective ablation of the biological tissue. In some examples, the method also includes the step of collecting, tracking, and/or monitoring tissue temperature of the biological tissue with the thermocouple 62, 562 of the irrigated electrode assembly 12, 512.

Certain implementations may be described with reference to the following exemplary clauses:

Clause 1—An electrode assembly comprising: an insulative body comprising a proximal end opposite a distal end, and defining a lumen between said proximal and distal ends; a proximal emitter coupled to the insulative body and defining a proximal channel in communication with said lumen; a distal emitter defining a distal channel in communication with said proximal channel and said lumen; an insulative spacer extending between said proximal emitter and said distal emitter; a first conduit extending through said lumen and at least a portion of said proximal channel, said first conduit defining a discharge port within said proximal emitter, wherein said first conduit is configured to be arranged in fluid communication with an irrigation source to deliver irrigation adjacent to said proximal emitter; a second conduit extending through said lumen and said proximal channel, and further through at least a portion of said distal channel; and a thermocouple comprising a distal end positioned within said second conduit near a distal tip of said electrode assembly.

Clause 2—An electrode assembly comprising: an insulative body comprising a proximal end opposite a distal end, and defining a lumen between said proximal and distal ends; a proximal emitter coupled to the insulative body and defining a proximal channel in communication with said lumen; a distal emitter defining a distal channel in communication with said proximal channel and said lumen; an insulative spacer extending between said proximal emitter and said distal emitter; a first conduit extending through said lumen and at least a portion of said proximal channel, wherein said first conduit is formed from conductive material and in electrical communication with said proximal emitter; and a second conduit extending through said lumen and said proximal channel, and further through at least a portion of said distal channel, wherein said second conduit is formed from conductive material and in electrical communication with said distal emitter.

Clause 3—An electrode assembly comprising: an insulative body comprising a proximal end opposite a distal end, and defining a lumen between said proximal and distal ends; a proximal emitter coupled to the insulative body and defining a proximal channel in communication with said lumen; a distal emitter defining a distal channel in communication with said proximal channel and said lumen; an insulative spacer extending between said proximal emitter and said distal emitter; a first conduit extending through said lumen and at least a portion of said proximal channel, said first conduit comprising a discharge port on said proximal emitter, wherein said first conduit is configured to be arranged in fluid communication with an irrigation source to deliver irrigation adjacent to said proximal emitter, wherein said first conduit is formed from conductive material and in electrical communication with said proximal emitter; a second conduit extending through said lumen and said proximal channel, and further through at least a portion of said distal channel, wherein said second conduit is formed from conductive material and in electrical communication with said distal emitter; and a thermocouple comprising a distal end positioned within said second conduit near a distal tip of said electrode assembly.

Clause 4—An electrode assembly configured to be deployed into tissue at an angle of approach relative to the tissue, said electrode assembly comprising: an insulative body comprising a proximal end opposite a distal end, and defining a lumen between said proximal and distal ends; a bipolar electrode coupled to said distal end of said insulative body, said bipolar electrode comprising: a proximal emitter defining a proximal channel in communication with said lumen, said proximal emitter comprising a distal end opposite a proximal end; a distal emitter; an insulative spacer extending between said proximal emitter and said distal emitter; and a first conduit formed from conductive material and in electrical communication with said proximal emitter, said first conduit extending through said lumen and at least a portion of said proximal channel, wherein said first conduit defines a discharge port on said proximal emitter between said proximal and distal ends and spaced apart from said distal end of said proximal emitter such that, as said electrode assembly is deployed into the tissue at the angle of approach, irrigation delivered through said discharge port flows along a portion of said proximal emitter distal to said discharge port under influence of gravity.

Clause 5—The electrode assembly of clause 4, wherein said first conduit comprises an elbow disposed within said proximal channel such that said discharge port is oriented at a right angle relative to a longitudinal axis of said electrode assembly.

Clause 6—An electrode assembly comprising: an insulative body comprising a proximal end opposite a distal end, and defining a lumen between said proximal and distal ends; a proximal emitter coupled to the insulative body and defining a proximal channel in communication with said lumen; a distal emitter defining a distal channel in communication with said proximal channel and said lumen; an insulative spacer extending between said proximal emitter and said distal emitter; a first conduit extending through said lumen and at least a portion of said proximal channel, said first conduit formed from conductive material and in electrical communication with said proximal emitter; and a second conduit extending through said lumen and said proximal channel, and through at least a portion of said distal channel, said second conduit formed from conductive material and in electrical communication with said distal emitter, wherein said proximal emitter has an outer diameter that is at least 33% greater than an outer diameter of each of said first and second conduits such that said outer diameter of said proximal emitter being larger than said outer diameters of said conductive materials of said first and second conduits facilitates improved visualization with electromagnetic imaging techniques.

Clause 7—An electrode assembly configured to be deployed into tissue at an angle of approach relative to the tissue, said electrode assembly comprising: an insulative body comprising a proximal end opposite a distal end, and defining a lumen between said proximal and distal ends; a proximal emitter coupled to the insulative body; a distal emitter; an insulative spacer extending between said proximal emitter and said distal emitter, said insulative spacer comprising (i) a spacer body, (ii) a proximal shoulder having an outer diameter less than an outer diameter of said spacer body, and (iii) a distal shoulder having an outer diameter less than said outer diameter of said spacer body, and (iv) a bore extending through said insulative spacer, (v) a slot extending longitudinally within said proximal shoulder and in communication with said bore; and a first conduit extending through said lumen of said insulative body and comprising a bend disposed within said slot, said first conduit comprising an irrigation port within said proximal emitter, wherein said first conduit is configured to be arranged in fluid communication with an irrigation source to deliver irrigation adjacent to said proximal emitter.

Clause 8—The electrode assembly of clause 7, further comprising: a second conduit extending through said lumen of said insulative body and said bore of said insulative spacer; and a thermocouple extending through said second conduit and comprising a distal end positioned near a distal tip of said electrode assembly.

Clause 9—The electrode assembly of clauses 7 or 8, wherein said proximal emitter defines a proximal channel and comprises a threaded fitting coupled to said insulative body, wherein said proximal shoulder of said insulative spacer is within said proximal channel and extends within said threaded fitting.

Clause 10—The electrode assembly of any one of clauses 7-9, wherein said proximal emitter defines a proximal channel with said proximal shoulder disposed within said proximal channel and extending proximally to a distal end of said proximal emitter, wherein said proximal shoulder is coupled directly to said insulative body.

Clause 11—The electrode assembly of clause 10, wherein said insulative body is formed from polymeric material and said insulative spacer is formed from polymeric material, said electrode assembly further comprising adhesive coupling said insulative body and said insulative spacer.

Clause 12—An electrode assembly configured to be deployed into tissue at an angle of approach relative to the tissue, said electrode assembly comprising: an insulative body comprising a proximal end opposite a distal end, and defining a lumen between said proximal and distal ends; a proximal emitter; a distal emitter; an insulative spacer extending between said proximal emitter and said distal emitter; an adapter comprising (i) an adapter body, (ii) a proximal shoulder having an outer diameter less than an outer diameter of said adapter body, and (iii) a distal shoulder having an outer diameter less than said outer diameter of said adapter body, said distal shoulder coupled with said insulative body, and (iv) a bore extending through said adapter, (v) an adapter slot extending longitudinally within said distal shoulder and in communication with said bore; and a first conduit extending through said lumen of said insulative body and said at least a portion of said bore, said first conduit comprising a bend disposed within said adapter slot, said first conduit comprising an irrigation port within said proximal emitter, wherein said first conduit is configured to be arranged in fluid communication with an irrigation source to deliver irrigation adjacent to said proximal emitter.

Clause 13—The electrode assembly of clause 12, further comprising: a second conduit extending through an entirety said bore; and a thermocouple extending through said second conduit and comprising a distal end positioned near a distal tip of said electrode assembly.

Clause 14—The electrode assembly of clause 13, wherein said insulative body is formed from polymeric material and said adapter is formed from polymeric material, said electrode assembly further comprising adhesive coupling said insulative body and said adapter.

Clause 15—The electrode assembly of any one of clauses 12-14, wherein said adapter is machined from a single piece of polyether ether ketone (PEEK).

Clause 16—The electrode assembly of clauses 2 or 7, wherein said first and second conduits are formed from conductive material and in electrical communication with said proximal and distal emitters, respectively.

Clause 17—The electrode assembly of any one of clauses 1-10, wherein said insulative spacer is machined from a single piece of polyether ether ketone (PEEK).

Clause 18—An electrode assembly configured to be deployed into tissue at an angle of approach relative to the tissue, said electrode assembly comprising: an insulative body comprising a proximal end opposite a distal end, and defining a lumen between said proximal and distal ends; a proximal emitter comprising a proximal annular body that defines a proximal channel in communication with said lumen, said proximal emitter comprising a distal end opposite a proximal end; a distal emitter comprising a distal annular body that defines a distal channel in communication with said lumen; an insulative spacer extending between said proximal emitter and said distal emitter, said insulative spacer comprising (i) a spacer annular body that has an outer diameter complementary to said proximal and distal annular bodies, (ii) a proximal shoulder extending from said spacer annular body and having an outer diameter less than said outer diameter of said spacer annular body so as to be coupled to said spacer annular body via friction fit, and (iii) a distal shoulder extending from said spacer annular body in a direction opposite said proximal shoulder, said distal shoulder having an outer diameter less than said outer diameter of said spacer annular body so as to be coupled to said spacer annular body via friction fit, and (iv) a lumen extending through said insulative spacer, wherein said insulative spacer is formed of unitary construction; and optionally, an adhesive coupling said insulative spacer to each of said proximal and distal emitters along respective lengths of said friction fit.

Clause 19—The electrode assembly of clause 18, wherein said insulative spacer is machined from a single piece of polyether ether ketone (PEEK).

Clause 20—The electrode assembly of clauses 18 or 19, wherein said length of said distal shoulder is greater than said length of said proximal shoulder so as to extend within said distal emitter to a position near a distal tip of said electrode assembly.

Clause 21—The electrode assembly of any one of clauses 18-20, wherein said proximal emitter comprises a threaded fitting configured to engage a complementary threaded fitting of said insulative body.

Clause 22—The electrode assembly of clause 21 further comprising optionally, additional adhesive coupling said threaded fittings.

Clause 23—The electrode assembly of any one of clauses 18-22, further comprising: a first conduit extending through said lumen and at least a portion of said proximal channel, said first conduit defining an irrigation port within said proximal emitter, wherein said first conduit is configured to be arranged in fluid communication with an irrigation source to deliver irrigation adjacent to said proximal emitter; and a second conduit extending through said lumen and said proximal channel, and further through at least a portion of said distal channel.

Clause 24—The electrode assembly of clause 23, further comprising a thermocouple positioned within said second conduit.

Clause 25—An ablation system, said ablation system comprising: an irrigated electrode assembly having a proximal portion with a proximal end, a distal portion with a distal end, and an insulative body, said irrigated electrode assembly defining at least one irrigation channel that extends from said proximal portion of said irrigated electrode assembly to said distal portion of said irrigated electrode assembly, wherein said irrigated electrode assembly includes one or more fluid intake ports at said proximal portion of said irrigated electrode assembly and one or more fluid irrigation ports at said distal portion of said irrigated electrode assembly, wherein said one or more fluid intake ports and said one or more fluid irrigation ports are in fluid communication with said at least one irrigation channel; a micro infusion module releasably coupled to said irrigated electrode assembly and sized to be held by a single hand, said micro infusion module comprising: a vacuum accumulator which is configured to store potential energy; and a fluid delivery actuator configured to cooperate with said vacuum accumulator, said fluid delivery actuator comprising a body defining a fluid reservoir and a piston moveably disposed in said fluid reservoir, wherein said vacuum accumulator and said fluid delivery actuator are configured to simultaneously fill a fluid reservoir within said fluid delivery actuator and store potential energy in said vacuum accumulator via said application of force when uncoupled from said irrigated electrode assembly, and wherein said vacuum accumulator and said fluid delivery actuator are in fluidic communication with said at least one irrigation channel and said one or more fluid irrigation ports, and said vacuum accumulator and said fluid delivery actuator are configured to release said potential energy and actuate said piston to discharge fluid from said fluid reservoir and into said at least one irrigation channel and out of said one or more fluid irrigation ports.

Clause 26—The ablation system as set forth in clause 25, wherein said one or more fluid delivery actuators have a total volumetric capacity from about 2 to about 8 mL.

Clause 27—The ablation system as set forth in clauses 25 or 26, further comprising a first and second conduit, said first conduit defining a first irrigation channel and said second conduit defining a second irrigation channel.

Clause 28—The ablation system as set forth in clause 27, wherein said first and second conduits comprise a conductive material.

Clause 29—The ablation system as set forth in clause 27 or 28, wherein said first and second conduits are isolated from one another by said insulative body.

Clause 30—The ablation system as set forth in any one of clauses 27-29, wherein said insulative body has a central web that electrically isolates said first and second irrigation channels.

Clause 31—The ablation system as set forth in any one of clauses 25-30, wherein said insulative body comprises a polymeric material.

Clause 32—The ablation system as set forth in in any one of clauses 25-31 comprising a flow restrictor configured to constrict fluid flow to a rate of from about 0.5 to about 15 mL/hour.

Clause 33—The ablation system as set forth in clause 32, wherein said distal portion includes a distal fluid irrigation port defined by said distal transfer surface and a proximal fluid irrigation port defined by said proximal transfer surface.

Clause 34—The ablation system as set forth in any one of clauses 25-33, wherein said micro infusion module comprises one of said one or more fluid delivery actuators and two of said one or more vacuum accumulators, said vacuum accumulators spaced equidistant from a side of said fluid delivery actuator.

Clause 35—The ablation system as set forth in any one of clauses 25-34, wherein said micro infusion module is sterilized.

Clause 36—The ablation system as set forth in any one of clauses 25-35, wherein said micro infusion module is free of a spring, a battery, and an electrical power source or a connection thereto.

Clause 37—An ablation system, said ablation system comprising: an irrigated electrode assembly having a proximal portion with a proximal end, a distal portion with a distal end, said irrigated electrode assembly comprising: an insulative body; one or more fluid intake ports at said proximal portion of said irrigated electrode assembly; a first conduit defining a first irrigation channel and a second conduit defining a second irrigation channel, said first and second conduits: extending from said proximal portion of said irrigated electrode assembly to said distal portion of said irrigated electrode assembly; comprising an electrically conductive material; and isolated from one another by said insulative body; a distal transfer surface on said distal portion of said irrigated electrode assembly and a proximal transfer surface located on said distal portion of said irrigated transfer surface assembly and positioned proximally relative to said distal transfer surface; a distal fluid irrigation port defined by said distal transfer surface and a proximal fluid irrigation port defined by said proximal transfer surface, said fluid irrigation ports in fluid communication with said first and second irrigation channels; and a micro infusion source releasably coupled to said irrigated electrode assembly and having a total volumetric fluid capacity of less than about 10 mL, wherein said micro infusion source is in fluidic communication with said first and second irrigation channels and said distal and proximal fluid irrigation ports, and is configured to discharge fluid from said fluid reservoir and into said first and second irrigation channels and out of said distal and proximal fluid irrigation ports.

Clause 38—The ablation system as set forth in clause 37, wherein said micro infusion module is sterilized.

Clause 39—The ablation system as set forth in clause 37 or 38, wherein said micro infusion source has a total volumetric fluid capacity from about 2 to about 8 mL.

Clause 40—The ablation system as set forth in any one of clauses 37-39, wherein said insulative body has a central web that electrically isolates said first and second irrigation channels.

Clause 41—The ablation system as set forth in any one of clauses 37-40 comprising a flow restrictor that restricts fluid flow to a rate of from about 0.5 to about 15 mL/hour through said one or more irrigation channels.

Clause 42—The ablation system as set forth in any one of clauses 37-41, wherein said micro infusion module comprises a body defining a fluid reservoir and a piston moveably disposed in said fluid reservoir, wherein said micro infusion module is configured to store potential energy and release said potential energy and actuate said piston to discharge fluid from said fluid reservoir and into said first and second irrigation channels and out of said distal and proximal fluid irrigation ports.

Clause 43—The ablation system as set forth in any one of clauses 37-42, wherein said micro infusion module comprises: a vacuum accumulator which is configured to store potential energy; and a fluid delivery actuator configured to cooperate with said vacuum accumulator, wherein said vacuum accumulator and said fluid delivery actuator are configured to simultaneously fill a fluid reservoir within said fluid delivery actuator and store potential energy in said vacuum accumulator via said application of force when uncoupled from said irrigated electrode assembly, wherein said vacuum accumulator and said fluid delivery actuator are in fluidic communication with said first and second irrigation channels and said distal and proximal fluid irrigation ports, and said vacuum accumulator and said fluid delivery actuator are configured to release said potential energy and actuate said piston to discharge fluid from said fluid reservoir and into said first and second irrigation channels and out of said one or more fluid irrigation ports.

Clause 44—The ablation system as set forth in clause 43, wherein said micro infusion module comprises two of said vacuum accumulator.

Clause 45—The ablation system as set forth in clause 43 or 44, wherein said micro infusion module comprises two of said fluid delivery actuator.

Clause 46—The ablation system as set forth in any one of clauses 37-45, wherein said micro infusion module is free of a battery and an electrical power source or a connection thereto.

Clause 47—A method of ablating biological tissue with an ablation system comprising an irrigated electrode assembly and a micro infusion module sized to be held by a single hand, said method comprising the steps of: positioning an access cannula into bone; inserting the irrigated electrode assembly at least partially into the access cannula; coupling the irrigated electrode assembly to an energy source, the energy source being positioned outside a sterile zone; filling a fluid reservoir of the micro infusion module with fluid; applying force to the micro infusion module to store potential energy therein; coupling the micro infusion module to the irrigated electrode assembly positioning the micro infusion module within the sterile zone while the energy source remains outside the sterile zone; discharging fluid from the micro infusion module, through the irrigated electrode assembly, and into the biological tissue while the micro infusion module remains inside the sterile zone; and applying energy from the energy source to the biological tissue through the irrigated electrode assembly.

Clause 48—The method of ablating biological tissue as set forth in clause 47, wherein no more than about 8 mL of fluid is discharged.

Clause 49—The method of ablating biological tissue as set forth in clause 47 or 48, wherein the step of discharging is further defined as discharging fluid into biological tissue at a rate of from about 0.5 to about 15 mL/hour.

Clause 50—The method of ablating biological tissue as set forth in any one of clauses 47-49, wherein the step of discharging is further defined as discharging fluid into biological tissue at a rate of from about 2 to about 8 mL/hour.

Clause 51—The method of ablating biological tissue as set forth in any one of clauses 47-50, wherein the step of discharging is further defined as discharging at a rate of about 9 mL/hour for a period of from about 5 to about 25 minutes.

Clause 52—The method of ablating biological tissue as set forth in any one of clauses 47-51 further comprising the step of positioning the micro infusion module on the patient or patient support apparatus before or during the step of discharging.

Clause 53—The method of ablating biological tissue as set forth in any one of clauses 47-52, wherein the fluid comprises saline.

Clause 54—The method of ablating biological tissue as set forth in any one of clauses 47-53, wherein the biological tissue comprises nerve(s) or tumorous tissue.

Clause 55—The method of ablating biological tissue as set forth in any one of clauses 47-54 further comprising the step of positioning the distal end of the irrigated electrode assembly within a vertebral body adjacent a tumor.

Clause 56—The method of ablating biological tissue as set forth in any one of clauses 47-54 further comprising the step of positioning the distal end of the irrigated electrode assembly adjacent a facet nerve proximate a vertebral body.

Clause 57—The method of ablating biological tissue as set forth in any one of clauses 47-54 further comprising the step of positioning the irrigated electrode assembly within a vertebral body such that a proximal transfer surface and a distal transfer surface are positioned on opposite sides of a basivertebral nerve.

Clause 58—The method of ablating biological tissue as set forth in any one of clauses 47-57 further comprising the step of collecting temperature measurements from a thermocouple disposed within the irrigated electrode assembly.

Clause 59—The method of ablating biological tissue as set forth in any one of clauses 47-58 further comprising the step of holding the micro infusion module in one hand and applying force to a handle on the micro infusion module with the other hand to simultaneously fill a fluid reservoir within one or more fluid delivery actuators and store potential energy in one or more vacuum accumulators.

Clause 60—The method of ablating biological tissue as set forth in any one of clauses 47-59 further comprising the step of holding the micro infusion module in one hand and applying force to a handle on the micro infusion module with the other hand to simultaneously fill a single fluid reservoir within a fluid delivery actuator and store potential energy in two vacuum accumulators.

Clause 61—The method of ablating biological tissue as set forth in any one of clauses 47-60 further comprising the step of unpackaging a sterilized micro infusion module prior to the step of coupling the micro infusion module to the irrigated electrode assembly.

Clause 62—An ablation system, said ablation system comprising: an irrigated electrode assembly having a proximal portion with a proximal end, a distal portion with a distal end, and an insulative body, said irrigated electrode assembly defining at least one irrigation channel that extends from said proximal portion of said irrigated electrode assembly to said distal portion of said irrigated electrode assembly, wherein said irrigated electrode assembly includes one or more fluid intake ports at said proximal portion of said irrigated electrode assembly and one or more fluid irrigation ports at said distal portion of said irrigated electrode assembly, wherein said one or more fluid intake ports and said one or more fluid irrigation ports are in fluid communication with said at least one irrigation channel; a micro infusion module releasably coupled to said irrigated electrode assembly and sized to be held by a single hand, said micro infusion module a micro infusion source releasably coupled to said irrigated electrode assembly and configured to discharge fluid at a rate of from about 0.5 to about 15 mL/hour; wherein said micro infusion module is in fluidic communication with said at least one irrigation channel and said one or more fluid irrigation ports, and is configured to discharge fluid from said fluid reservoir and into said at least one irrigation channel and out of said one or more fluid irrigation ports.

Clause 63—An ablation system, said ablation system comprising: an irrigated electrode assembly having a proximal portion with a proximal end, a distal portion with a distal end, said irrigated electrode assembly comprising: an insulative body; one or more fluid intake ports on said proximal portion of said irrigated electrode assembly; a first conduit defining a first irrigation channel and a second conduit defining a second irrigation channel, said first and second conduits: extending from said proximal portion of said irrigated electrode assembly to said distal portion of said irrigated electrode assembly; comprising an electrically conductive material; and isolated from one another by said insulative body; a distal transfer surface located on said distal portion of said irrigated electrode assembly and a proximal transfer surface located on said distal portion of said irrigated electrode assembly and positioned proximally relative to said distal transfer surface; a distal fluid irrigation port defined by said distal transfer surface and a proximal fluid irrigation port defined by said proximal transfer surface, said distal and proximal fluid irrigation ports in fluid communication with said first and second irrigation channels and configured to discharge fluid into biological tissue.

Clause 64—An ablation system, said ablation system comprising: an irrigated electrode assembly having a proximal portion with a proximal end, a distal portion with a distal end, said irrigated electrode assembly comprising: one or more fluid intake ports on said proximal portion of said irrigated electrode assembly; a flexible insulative body; a first conduit defining a first irrigation channel and a second conduit defining a second irrigation channel, said first and second conduits comprising an electrically conductive material and located on opposite sides of said insulative body; a distal emitter defining a distal transfer surface and mounted to said distal portion of said irrigated electrode assembly and a proximal emitter defining a proximal transfer surface and mounted to said distal portion of said irrigated electrode assembly and positioned proximally relative to said distal emitter, wherein a cumulative length of said first and second emitters is shorter than a length of said distal portion of said irrigated electrode assembly; a distal fluid irrigation port defined by said distal transfer surface and a proximal fluid irrigation port defined by said proximal transfer surface, said distal and proximal fluid irrigation ports in fluid communication with said first and second irrigation channels and configured to discharge fluid into biological tissue.

Clause 65—An ablation system includes an irrigated electrode assembly having a proximal portion with a proximal end, a distal portion with a distal end. The irrigated comprises an insulative body defining a cavity. A fluid intake port is located on said proximal portion of said irrigated electrode assembly. A first conduit comprises an electrically conductive material and defining an irrigation channel extends from said proximal portion of said irrigated electrode assembly to said distal portion of said irrigated electrode assembly. A second conduit comprises an electrically conductive material and defines a channel extending from said proximal portion of said irrigated electrode assembly to said distal portion of said irrigated electrode assembly. A thermocouple is housed within and insulated from said second conduit. A proximal transfer surface is defined by a proximal emitter located on said distal portion of said irrigated electrode assembly and defining a fluid irrigation port configured to discharge fluid into tissue, wherein said first conduit is in electrical communication with said proximal transfer surface and said irrigation channel is in fluid communication with said fluid irrigation port. A distal transfer surface is defined by a distal emitter located on said distal portion of said irrigated electrode assembly and positioned distally relative to said proximal transfer surface, wherein said second conduit is in electrical communication with said distal transfer surface.

Clause 66—An ablation system includes an irrigated electrode assembly having a proximal portion with a proximal end and a distal portion with a distal end. The irrigated electrode assembly includes an insulative body, one or more fluid intake ports on the proximal portion of the irrigated electrode assembly, a first conduit defining a first irrigation channel, and a second conduit defining a second irrigation channel. The first and second conduits extend from the proximal portion of the irrigated electrode assembly to the distal portion of the irrigated electrode assembly, comprise an electrically conductive material, and are isolated from one another by the insulative body. The electrode assembly includes a distal transfer surface located on the distal portion of the irrigated electrode assembly, and a proximal transfer surface located on the distal portion of the irrigated electrode assembly and positioned proximally relative to the distal transfer surface. Moreover, a distal fluid irrigation port is defined by the distal transfer surface, and a proximal fluid irrigation port is defined by the proximal transfer surface. The distal and proximal fluid irrigation ports are in fluid communication with the first and second irrigation channels and configured to discharge fluid into biological tissue.

Clause 67—An ablation system includes an irrigated electrode assembly having a proximal portion with a proximal end and a distal portion with a distal end. The irrigated electrode assembly includes one or more fluid intake ports on the proximal portion of the irrigated electrode assembly, an insulative body, a first conduit defining a first irrigation channel, and a second conduit defining a second irrigation channel. The first and second conduits comprise an electrically conductive material and are located on opposite sides of the flexible insulative body. A distal emitter defines a distal transfer surface and is mounted to the distal portion of the irrigated electrode assembly, while a proximal emitter defines a proximal transfer surface and is mounted to the distal portion of the irrigated electrode assembly and positioned proximally relative to the distal emitter. A cumulative length of the first and second emitters is shorter than a length of the distal portion of the irrigated electrode assembly. In addition, a distal fluid irrigation port is defined by the distal transfer surface and a proximal fluid irrigation port is defined by the proximal transfer surface. The distal and proximal fluid irrigation ports are in fluid communication with the first and second irrigation channels and are configured to discharge fluid into biological tissue.

Clause 68—An ablation system includes an irrigated electrode assembly and a micro infusion source releasably coupled to the irrigated electrode assembly. The irrigated electrode assembly has a proximal portion with a proximal end, a distal portion with a distal end. Further, the irrigated electrode assembly comprises an insulative body, one or more fluid intake ports at the proximal portion of the irrigated electrode assembly, a first conduit defining a first irrigation channel and a second conduit defining a second irrigation channel. The first and second conduits extend from the proximal portion of the irrigated electrode assembly to the distal portion of the irrigated electrode assembly, comprise an electrically conductive material, and are isolated from one another by the insulative body. The irrigated electrode assembly includes a distal transfer surface on the distal portion, and a proximal transfer surface on the distal portion of the irrigated transfer surface assembly and positioned proximally relative to the distal transfer surface. Moreover, a distal fluid irrigation port is defined by the distal transfer surface and a proximal fluid irrigation port is defined by the proximal transfer surface, with the distal and proximal fluid irrigation ports in fluid communication with the first and second irrigation channels. The micro infusion source is in fluidic communication with the first and second irrigation channels and the distal and proximal fluid irrigation ports and is configured to discharge fluid from the fluid reservoir and into the first and second irrigation channels and out of the distal and proximal fluid irrigation ports. Further, the micro infusion source is configured to discharge fluid at a rate of from about 0.5 to about 15 mL/hour and/or has a fluid capacity of less than about 10 mL.

Clause 69—An ablation assembly includes an irrigated electrode assembly and a micro infusion module releasably coupled to the irrigated electrode assembly and sized to be held by a single hand. The irrigated electrode assembly has a proximal portion with a proximal end, a distal portion with a distal end, and an insulative body. The irrigated electrode assembly defines at least one irrigation channel that extends from the proximal portion of the irrigated electrode assembly to the distal portion of the irrigated electrode assembly. Further, the irrigated electrode assembly includes one or more fluid intake ports at the proximal portion of the irrigated electrode assembly and one or more fluid irrigation ports at the distal portion of the irrigated electrode assembly, both the intake and irrigation ports being in fluid communication with the at least one irrigation channel. The micro infusion module is configured to discharge fluid at a rate of from about 0.5 to about 15 mL/hour and/or has a fluid capacity of less than about 10 mL. The micro infusion module is in fluidic communication with the at least one irrigation channel and the one or more fluid irrigation ports and is configured to discharge fluid from the fluid reservoir and into the at least one irrigation channel and out of the one or more fluid irrigation ports.

Clause 70—An ablation system includes an irrigated electrode assembly and a micro infusion module releasably coupled to the irrigated electrode assembly and sized to be held by a single hand. The irrigated electrode assembly has a proximal portion with a proximal end, a distal portion with a distal end, and an insulative body. The irrigated electrode assembly defines at least one irrigation channel that extends from the proximal portion of the irrigated electrode assembly to the distal portion of the irrigated electrode assembly. Further, the irrigated electrode assembly includes one or more fluid intake ports at the proximal portion of the irrigated electrode assembly and one or more fluid irrigation ports at the distal portion of the irrigated electrode assembly, both the intake and irrigation ports being in fluid communication with the at least one irrigation channel. The micro infusion module includes a vacuum accumulator configured to store potential energy and a fluid delivery actuator configured to cooperate with the vacuum accumulator. The fluid delivery actuator comprises a body defining a fluid reservoir and a piston moveably disposed in the fluid reservoir. When uncoupled from the irrigated electrode assembly, the vacuum accumulator and the fluid delivery actuator are configured to simultaneously fill a fluid reservoir within the fluid delivery actuator and store potential energy in the vacuum accumulator via the application of force. When coupled to the irrigated electrode assembly, the vacuum accumulator and the fluid delivery actuator are in fluidic communication with the at least one irrigation channel and the one or more fluid irrigation ports, and the vacuum accumulator and the fluid delivery actuator are configured to release the potential energy and actuate the piston to discharge fluid from the fluid reservoir and into the at least one irrigation channel and out of the one or more fluid irrigation ports.

Clause 71—Further, a method of ablating biological tissue with the ablation system comprising the irrigated electrode assembly and micro infusion module sized to be held by a single hand is disclosed. An access cannula is positioned into bone and the irrigated electrode assembly is at least partially into the access cannula. The irrigated electrode assembly is coupled to an energy source, the energy source being positioned outside a sterile zone. A fluid reservoir of the micro infusion module is filled with fluid and force is applied to the micro infusion module to store potential energy therein. Once filled with fluid, the micro infusion module is coupled to the irrigated electrode assembly and positioned within the sterile zone while the energy source remains outside the sterile zone. Finally, fluid is discharged from the micro infusion module, through the irrigated electrode assembly, and into the biological tissue while the micro infusion module remains inside the sterile zone, and energy is applied from the energy source to the biological tissue through the irrigated electrode assembly.

Several embodiments have been discussed in the foregoing description. However, the embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

It is to be understood that the appended claims are not limited to express any particular compounds, compositions, or methods described in the detailed description, which may vary between particular embodiments, which fall within the scope of the appended claims. With respect to any Markush groups relied upon herein for describing particular elements or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the instant disclosure independently and collectively fall within the scope of the appended claims, and are understood to describe and contemplate all ranges including whole and/or fractional values therein, even if such values are not expressly written herein.

What is claimed is:

1. An electrode assembly for ablation of tissue, the electrode assembly comprising:
   an insulative body;
   a proximal emitter coupled to the insulative body;
   an insulative spacer coupled to the proximal emitter;
   a distal emitter coupled to the insulative spacer;
   a first conduit extending through the insulative body and comprising an end secured to the proximal emitter, the first conduit comprising electrically conductive material configured to transmit energy from an energy source to the proximal emitter; and
   a second conduit extending through the insulative body and coupled to the distal emitter, the second conduit comprising electrically conductive material configured to transmit energy from the energy source to the distal emitter,
   wherein one of the proximal emitter and the distal emitter defines a fluid irrigation port configured to discharge fluid into the tissue and one of the first conduit and the second conduit defines an irrigation channel in fluid communication with the fluid irrigation port, and wherein a thermocouple is disposed within the other one of the first conduit and the second conduit.

2. The electrode assembly of claim 1, wherein the first conduit extends longitudinally through the insulative body and further comprises a bend configured to facilitate securing an end of the first conduit to the proximal emitter.

3. The electrode assembly of claim 1, wherein the proximal emitter defines the fluid irrigation port and the first conduit is secured to the proximal emitter within the fluid irrigation port to define the irrigation channel.

4. The electrode assembly of claim 1, wherein the proximal emitter further comprises threads threadably engaging complementary threads of the insulative body.

5. The electrode assembly of claim 1, wherein the insulative spacer comprises a distal shoulder disposed within and coupled to the distal emitter, and a proximal shoulder disposed within and coupled to the proximal emitter.

6. The electrode assembly of claim 5, wherein the proximal shoulder defines a slot sized to receive the first conduit.

7. The electrode assembly of claim 1, wherein the thermocouple is electrically insulated from the second conduit.

8. The electrode assembly of claim 1, wherein the electrode assembly defines a distal end, and wherein the second conduit is secured to the distal end in electrical communication with the distal emitter.

9. The electrode assembly of claim 8, wherein the distal end defines an aperture through which the thermocouple is exposed.

10. An electrode assembly for ablation of tissue, the electrode assembly comprising:
    an insulative body;
    a proximal emitter coupled to the insulative body;
    an insulative spacer coupled to the proximal emitter;
    a distal emitter coupled to the insulative spacer;
    a first conduit extending longitudinally through the insulative body, the first conduit comprising an electrically conductive material configured to transmit energy from an energy source to the proximal emitter, and a bend configured to orient an end of the first conduit distal to the bend to be secured to the proximal emitter; and
    a second conduit extending through the insulative body and the proximal emitter,
    wherein one of the proximal emitter and the distal emitter defines a fluid irrigation port configured to discharge fluid into the tissue and one of the first conduit and the second conduit defines an irrigation channel in fluid communication with the fluid irrigation port, and wherein a thermocouple is disposed in the other one of the first conduit and the second conduit.

11. The electrode assembly of claim 10, wherein the proximal emitter defines the fluid irrigation port and the first conduit defines the irrigation channel.

12. The electrode assembly of claim 10, wherein the insulative spacer defines a slot sized to receive the bend of the first conduit.

13. The electrode assembly of claim 12, wherein the insulative spacer comprises a proximal shoulder disposed within and coupled to the proximal emitter, wherein the proximal shoulder defines the slot.

14. The electrode assembly of claim 10, wherein the proximal emitter further comprises threads threadably engaging complementary threads of the insulative body.

15. The electrode assembly of claim 10, wherein the electrode assembly defines a distal end, and wherein the second conduit is secured to the distal end in electrical communication with the distal emitter.

16. The electrode assembly of claim 15, wherein the thermocouple is disposed within the second conduit, and wherein the distal end defines an aperture through which the thermocouple is exposed.

17. An electrode assembly for ablation of tissue, the electrode assembly comprising:
    an insulative body;
    a proximal emitter coupled to the insulative body and being formed from a metal;
    an insulative spacer coupled to the proximal emitter;
    a distal emitter coupled to the insulative spacer and being formed from a metal;
    a first conduit formed from a metal and extending through the insulative body and at least a portion of the proximal emitter, wherein the first conduit comprises an end secured to the proximal emitter and configured to transmit energy from an energy source to the proximal emitter; and
    a second conduit being formed from a metal and extending through the insulative body, the proximal emitter, and at least a portion of the distal emitter, wherein the second conduit is coupled to the distal emitter and configured to transmit energy from the energy source to the distal emitter, and wherein one of the proximal emitter and the distal emitter defines a fluid irrigation port and configured to discharge fluid into the tissue, wherein outer diameter of the proximal emitter is at least 33% greater than outer diameters of each of the first and second conduits such that a proximal end of the proximal emitter is discernable on electromagnetic imaging despite the first and second conduits being at least substantially radiopaque.

18. The electrode assembly of claim 17, further comprising a thermocouple disposed within the second conduit, wherein the proximal emitter defines a fluid irrigation port configured to discharge a fluid to the tissue, and wherein the first conduit is in fluid communication with the fluid irrigation port.

* * * * *